US009663491B2

United States Patent
Loso et al.

(10) Patent No.: US 9,663,491 B2
(45) Date of Patent: May 30, 2017

(54) METALLOENZYME INHIBITOR COMPOUNDS AS FUNGICIDES

(71) Applicant: Dow AgroSciences LLC, Indianapolis, IN (US)

(72) Inventors: Michael R. Loso, Carmel, IN (US); Gary D. Gustafson, Zionsville, IN (US); Asako Kubota, Arlington, VA (US); Maurice C. Yap, Zionsville, IN (US); Zachary A. Buchan, Zionsville, IN (US); Kimberly M. Steward, Zionsville, IN (US); Michael T. Sullenberger, Westfield, IN (US); William J. Hoekstra, Durham, NC (US); Christopher M. Yates, Raleigh, NC (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/683,857

(22) Filed: Apr. 10, 2015

(65) Prior Publication Data

US 2015/0291557 A1    Oct. 15, 2015

Related U.S. Application Data

(60) Provisional application No. 62/047,384, filed on Sep. 8, 2014, provisional application No. 61/979,540, filed on Apr. 15, 2014.

(51) Int. Cl.

| | | |
|---|---|---|
| *C07D 401/10* | (2006.01) | |
| *A01N 43/54* | (2006.01) | |
| *C07D 239/26* | (2006.01) | |
| *A61K 31/505* | (2006.01) | |
| *A61K 31/506* | (2006.01) | |
| *A01N 47/02* | (2006.01) | |
| *C07D 213/30* | (2006.01) | |
| *A61K 31/4406* | (2006.01) | |
| *C07D 213/32* | (2006.01) | |
| *C07D 213/57* | (2006.01) | |
| *C07D 239/34* | (2006.01) | |
| *A61K 45/06* | (2006.01) | |
| *A01N 53/00* | (2006.01) | |

(52) U.S. Cl.
CPC .......... *C07D 401/10* (2013.01); *A01N 43/54* (2013.01); *A01N 47/02* (2013.01); *A01N 53/00* (2013.01); *A61K 31/4406* (2013.01); *A61K 31/505* (2013.01); *A61K 31/506* (2013.01); *A61K 45/06* (2013.01); *C07D 213/30* (2013.01); *C07D 213/32* (2013.01); *C07D 213/57* (2013.01); *C07D 239/26* (2013.01); *C07D 239/34* (2013.01)

(58) Field of Classification Search
CPC .. C07D 213/30; C07D 213/32; C07D 213/57; C07D 239/26; C07D 239/34; C07D 401/10; A01N 43/54; A01N 47/02; A61K 31/4406; A61K 31/505; A61K 31/506
USPC .......... 544/333, 335; 546/339; 514/256, 277
See application file for complete search history.

(56) References Cited

U.S. PATENT DOCUMENTS

| | | | | |
|---|---|---|---|---|
| 4,417,050 A | * | 11/1983 | Cherpeck | ............. C07D 239/26 504/185 |
| 2005/0101639 A1 | | 5/2005 | Ammermann et al. | |
| 2008/0234313 A1 | | 9/2008 | Ramsbeck et al. | |
| 2012/0190639 A1 | | 7/2012 | Everett et al. | |

FOREIGN PATENT DOCUMENTS

| | | |
|---|---|---|
| WO | WO 85/00289 A1 | 1/1985 |
| WO | WO 0196283 A2 | 12/2001 |
| WO | WO 2012/151355 * | 11/2012 |
| WO | WO 2013/110002 A1 | 7/2013 |

OTHER PUBLICATIONS

Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1010, 1996.*

(Continued)

*Primary Examiner* — Deepak Rao
(74) *Attorney, Agent, or Firm* — Charles W. Arnett; Faegre Baker Daniels LLP

(57) ABSTRACT

The instant invention describes compounds of Formula I having metalloenzyme modulating activity, and methods of treating diseases, disorders or symptoms thereof mediated by such metalloenzymes.

17 Claims, No Drawings

(56) References Cited

OTHER PUBLICATIONS

Douglas, Jr., Introduction to Viral Diseases, Cecil Textbook of Medicine, 20th Edition, vol. 2, pp. 1739-1747, 1996.*
Bosseray et al., PubMed Abstract (Pathol Biol (Paris) 50(8):483-92), 2002.*
Goff, PubMed Abstract (J Gene Med. 3(6):517-28), 2001.*
Razonable et al., PubMed Abstract (Herpes 10(3):60-5), 2003.*
Layzer, Degenerative Diseases of the Nervous System, Cecil Textbook of Medicine, 20th Edition, vol. 2, pp. 2050-2057 (1996).*
Damasio, Alzheimer's Disease and Related Dementias, Cecil Textbook of Medicine, 20th Edition, vol. 2, pp. 1992-1996 (1996).*
Hu et al., Isopropylidene Substitution Increases Activity and Selectivity of Biphenylmethylene 4-Pyridine Type CYP17 Inhibitors, J. Med. Chem. vol. 53, No. 13, pp. 5049-5053 (2010).*
Schallner et all., CAPLUS Abstract 133:296445 (2000).*
Zierke et al., CAPLUS Abstract 118:254757 (1993).*
Regel et al., CAPLUS Abstract 92:128926 (1980).*
Cavallini et al., CAPLUS Abstract 55:18020 (1961).*
Pubchem. CID 4200806. Sep. 3, 2005, pp. 1-2 [online], (retrieved on Jun. 5, 2015] Retrieved from the Internet <URL: http://pubchem.ncbi.nlm.nih.gov/summary/summary cgi?from=compound&cid=4200806>; pag.
Pubchem. CID 5665BB04.Mar. 6, 2012, pp. 1-3 lonline), lretrieved on Jun. 5, 2015]. Retrieved from the Internet <URL; http://pubchem.ncbi,nlm,nih,gov/summary/summary cgi?from=compound&cid=56658804>; p. 1.
Pubchem. CID 14249696. Feb. 9, 2007. pp. 1-2 [online], [retrieved on Jun. 5, 2015] Retrieved from the Internet <URL: http://pubchem.ncbi.nlm.nih.gov/summary/summary.cgi?from=compound&cid=14249696>; p. 1.
Pubchem. CID 60924289. Oct. 19, 2012. pp. 1-2 [online], [retrieved on Jun. 5, 2015], Retrieved from the Internet <URL: http://pubchem.ncbi.nlm.nih.gov/summary/summary.cgi?from=compoundScid=60924289>; p. 1.
Powderly. WG et al. A Randomized Trial Comparing Fluconazole with Clolrimazole Troches for the Prevention of Fungal Infections in Patients with Advanced Human Immunodeficiency Virus Infection. The New England Journal of Medicine, vol. 332, No. 11, Mar. 16, 1995, pp. 700-705 [online), [retrieved on Jun. 5, 2015]. Retrieved from the Internet <URL: http://www.nejm.org/doi/pdf/10-1056/NEJM199503163321102>: p. 700, col. 1.
Agrawal, A et al Probing Chelation Motjfs in HIV Integrase Inhib'tors, Proc Natl Acad Sci U S A. vol. 109, No. 7. Feb. 14, 2012, pp. 2251-2256. [online], [retrieved on Jun. 5, 2015], Retrieved from the Internet <URL: http://www.pnas.Org/conlant/109/7/2251 fuil,pdf> <doi;10.1073/pnas.1 112389109>; abstract.
Wu. L. Biology of HIV Mucosal Transm ssion. Curr Opin HIV AIDS, vol. 3, No. 5. Sep. 2008. pp. 534-540. [online], [retrieved on Jun. 5, 2015]. Retrieved from the Internet <URL: http://www.ncbi nlm.nih gQv/pmc/artic[es/PMC2542876/pdf/nihms47772 pdf> <doi:10.1097/COH 0b013e32830634c6>; abstract.
Pubchem.CID 20345636. Dec. 5, 2007, pp. 1-3 [online], [retrieved on Jun. 5, 2015). Retrieved from the Internet <URL: hllp;//pubchem.ncbi.nlm.nih.gov/summaryi,summary.cgi?frQm=compound&cid=20345636>; page.
Pubchem. CID 59161937. Aug. 20, 2012, pp. 1-3 [omine], [retrieved on Jun. 5, 2015], Retrieved from the Internet <URL; http.7/pubchem,ncbi.n'im.nih.gov/summary/summary1cgi?from=compound&cid=59161937>; p. 1.
Dawson. Wajm et al. Sensitivity of Fungi from Cereal Roots to Fluquinconazole and their Suppressiveness towards Take-all on P ants with or without Fluquinconazole Seed Treatment in a Controlled Environment. Plant Pathology. vol. 49. 2000, pp. 477-486 [online], [retrieved on Jun. 5, 2015], Retrieved from the Internet <URL: htlp://onlinelibrary.wiley,CQm/doi/10.1046/j.1365-3059.2000.00479.x/epdf>; abstract.
Ashauer, R et al. A Method to Predict and Understand Fish Survival Under Dynamic Chemical Stress Using Standard Ecotoxicity Data. Environmental Toxicology and Chemistry, vol. 32. No. 4, 2013, pp. 954-965 [online], [retrieved on Jun. 5, 2015), Retrieved from the Internet <URL: http;//onlinelibrary,wiley.com/doi/10.1002/etc.2144/epdf>, p. 955, col. 1. paragraph 3.
Pubchem. CID 56604428. Feb. 22, 2012, pp. 1-2 (online], (retrieved on Jun. 5, 2015] Retrieved from the Internet <URL: http://pubchem.ncbi.nlm,nih.gov/summary/summary.cgi?from=compound&cid=56604428>; p. 1.

* cited by examiner

METALLOENZYME INHIBITOR COMPOUNDS AS FUNGICIDES

CROSS REFERENCE TO RELATED APPLICATIONS

This application claims the benefit of U.S. Provisional Patent Application Ser. Nos. 61/979,540 filed Apr. 15, 2014 and 62/047,384 filed Sep. 8, 2014, which are expressly incorporated by reference herein.

BACKGROUND & SUMMARY

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to metalloenzyme inhibitors and their use as fungicides. The compounds of the present disclosure may offer protection against ascomycetes, basidiomycetes, deuteromycetes and oomycetes.

One embodiment of the present disclosure may include compounds of Formula I:

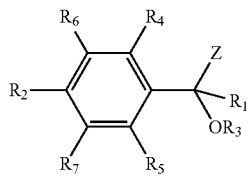

I

Where:

Z is optionally substituted 5-pyrimidinyl, optionally substituted 4-pyrimidinyl, optionally substituted thiazolyl, optionally substituted oxazolyl, or optionally substituted 3-pyridinyl;

$R_1$ is alkyl, haloalkyl, aryl, heteroaryl, each optionally substituted with 0, 1, 2 or 3 independent $R_8$;

$R_2$ is aryl or heteroaryl each optionally substituted with 0, 1, 2 or 3 independent $R_8$;

$R_3$ is independently H, alkyl, aryl, heteroaryl, arylalkyl, or heteroarylalkyl, —C(O)alkyl, or —Si(alkyl)$_3$, each optionally substituted with 0, 1, 2 or 3 independent $R_8$;

$R_4$, $R_5$, $R_6$, and $R_7$ are independently H, alkyl, haloalkyl, alkoxy, halo, or cyano; and $R_8$ is independently aryl, heteroaryl, alkyl, thioalkyl, cyano, haloalkyl, cyanoalkyl, hydroxy, alkoxy, halo, haloalkoxy, —C(O)alkyl, —C(O)OH, —C(O)O-alkyl, —SCF$_3$, —SF$_5$, —SCN, or —SO$_2$-alkyl.

Another embodiment of the present disclosure may include a fungicidal composition for the control or prevention of fungal attack comprising the compounds described above and a phytologically acceptable carrier material.

Yet another embodiment of the present disclosure may include a method for the control or prevention of fungal attack on a plant, the method including the steps of applying a fungicidally effective amount of one or more of the compounds described above to at least one of the fungus, the plant, and an area adjacent to the plant.

It will be understood by those skilled in the art that the following terms may include generic "R"-groups within their definitions, e.g., "the term alkoxy refers to an —OR substituent". It is also understood that within the definitions for the following terms, these "R" groups are included for illustration purposes and should not be construed as limiting or being limited by substitutions about Formula I.

The term "alkyl" refers to a branched, unbranched, or saturated cyclic carbon chain, including, but not limited to, methyl, ethyl, propyl, butyl, isopropyl, isobutyl, tertiary butyl, pentyl, hexyl, cyclopropyl, cyclobutyl, cyclopentyl, cyclohexyl and the like.

The term "alkenyl" refers to a branched, unbranched or cyclic carbon chain containing one or more double bonds including, but not limited to, ethenyl, propenyl, butenyl, isopropenyl, isobutenyl, cyclobutenyl, cyclopentenyl, cyclohexenyl, and the like.

The term "alkynyl" refers to a branched or unbranched carbon chain containing one or more triple bonds including, but not limited to, propynyl, butynyl and the like.

The term "aryl" or "Ar" refers to any aromatic ring, mono- or bi-cyclic, containing 0 heteroatoms.

The term "heterocycle" refers to any aromatic or non-aromatic ring, mono- or bi-cyclic, containing one or more heteroatoms.

The term "heteroaryl" or "Het" refers to any aromatic ring, mono- or bi-cyclic, containing one or more heteroatoms.

The term "alkoxy" refers to an —OR substituent.
The term "aryloxy" refers to an —OAr substituent.
The term "hetaryloxy" refers to an —OHet substituent.
The term "arylalkynyl" refers to an -≡—Ar substituent.
The term "heteroarylalkynyl" refers to an -≡—Het substituent.
The term "cyano" refers to a —C≡N substituent.
The term "hydroxyl" refers to an —OH substituent.
The term "amino" refers to a —NR$_2$ substituent.
The term "arylalkyl" refers to an -alkyl-Ar substituent.
The term "heteroarylalkyl" refers to an -alkyl-Het substituent.
The term "arylalkoxy" refers to —O(CH$_2$)$_n$Ar where n is an integer selected from the list 1, 2, 3, 4, 5, or 6.
The term "heteroarylalkoxy" refers to —O(CH$_2$)$_n$Het where n is an integer selected from the list 1, 2, 3, 4, 5, or 6.
The term "haloalkoxy" refers to an —OR substituent, wherein R is substituted with Cl, F, Br, or I, or any combination of one or more halogen atoms.
The term "haloalkyl" refers to an alkyl, which is substituted with one or more halogen atoms.
The term "cyanoalkyl" refers to an alkyl, which is substituted with a cyano group.
The term "halogen" or "halo" refers to one or more halogen atoms, defined as F, Cl, Br, and I.
The term "nitro" refers to a —NO$_2$ substituent.
The term thioalkyl refers to an —SR substituent.

Throughout the disclosure, reference to the compounds of Formula I is read as also including diastereomers, enantiomers, and mixtures thereof. In another embodiment, Formula (I) is read as also including salts or hydrates thereof. Exemplary salts include, but are not limited to: hydrochloride, hydrobromide, and hydroiodide.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, seeds, and/or roots.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

DETAILED DESCRIPTION

The compounds of the present disclosure may be applied by any of a variety of known techniques, either as the compounds or as formulations comprising the compounds. For example, the compounds may be applied to the seeds, roots or foliage of plants for the control of various fungi, without damaging the commercial value of the plants. The materials may be applied in the form of any of the generally used formulation types, for example, as solutions, dusts, wettable powders, flowable concentrate, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water-suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water-dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 1 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil-soluble salts or sulfated polyglycol ethers and appropriate salts of phosphated polyglycol ether.

Representative organic liquids which may be employed in preparing the emulsifiable concentrates of the compounds of the present disclosure are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 1 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrrate; emulsified methylated seed oil; tridecyl alcohol (synthetic) ethoxylate (8EO); tallow amine ethoxylate (15 EO); PEG (400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present disclosure in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank-mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, *Bacillus subtilis* strain QST713, benalaxyl, benomyl, benthiavalicarb-isopropyl, benzovindiflupyr, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila*, *Fusarium oxysporum*, *Gliocladium* spp., *Phlebiopsis gigantea*, *Streptomyces griseoviridis*, *Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

Additionally, the compounds described herein may be combined with other pesticides, including insecticides, nematocides, miticides, arthropodicides, bactericides or combinations thereof that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank-mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, taufluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof.

Additionally, the compounds described herein may be combined with herbicides that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank-mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, diallate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-P, glyphosate, halauxifen, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac, tritosulfuron, vernolate, and xylachlor.

Another embodiment of the present disclosure is a method for the control or prevention of fungal attack. This method comprises applying to the soil, plant, roots, seeds, foliage, or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those in the art that the efficacy of the compound for the foregoing fungi establishes the general utility of the compounds as fungicides.

The compounds have broad ranges of activity against fungal pathogens. Exemplary pathogens may include, but are not limited to, causing agent of wheat leaf blotch (*Mycosphaerella graminicola*; impect stage: *Septoria tritici*), wheat brown rust (*Puccinia triticina*), wheat stripe rust (*Puccinia striiformis*), scab of apple (*Venturia inaequalis*), powdery mildew of grapevine (*Uncinula necator*), barley scald (*Rhynchosporium secalis*), blast of rice (*Magnaporthe grisea*), rust of soybean (*Phakopsora pachyrhizi*), glume blotch of wheat (*Leptosphaeria nodorum*), powdery mildew of wheat (*Blumeria graminis* f sp. *tritici*), powdery mildew of barley (*Blumeria graminis* f. sp. *hordei*), powdery mildew of cucurbits (*Erysiphe cichoracearum*), anthracnose of cucurbits (*Glomerella lagenarium*), leaf spot of beet (*Cercospora beticola*), early blight of tomato (*Alternaria solani*), and spot blotch of barley (*Cochliobolus sativus*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

General Schemes

The following schemes illustrate approaches to generating metalloenzyme inhibitor compounds of Formula I. The following descriptions and examples are provided for illustrative purposes and should not be construed as limiting in terms of substituents or substitution patterns.

The compound of Formula 1.6, wherein $R_1$, $R_2$, $R_3$, $R_4$, $R_5$, $R_6$, $R_7$, $R_8$, and Z are as originally defined, can be prepared as shown in Scheme 1, steps a-d from the appropriately substituted precursors, such as compounds of Formulae 1.0 and 1.1. The compound of Formula 1.2 can be prepared via metallation chemistry by treating a solution of an appropriately substituted heteroaryl bromide, such as the bromide of Formula 1.0, 5-bromopyrimidine, in a mixture of polar, aprotic solvents, for example diethyl ether ($Et_2O$) and tetrahydrofuran (THF), wherein the ratio of the solvents is about 1:1, with n-butyllithium (n-BuLi) at a reduced temperature of about −107° C., as described by Frissen, A. E. et. al. (Tetrahedron (1989), 45(17), 5611-5620). The resultant aryl lithium or heteroaryl lithium, for example 5-lithiopyrimidine, can be quenched with a solution of an appropriately substituted aldehyde, such as the aldehyde of Formula 1.1, 4-bromobenzaldehyde, in a polar, aprotic solvent like THF at a reduced temperature from about −107° C. to about −67° C., as shown in step a. Ketones like the compound of Formula 1.3 can be prepared via oxidation of an appropriately substituted secondary alcohol, for example the alcohol of Formula 1.2, by treating with an oxidant, such as manganese dioxide ($MnO_2$), in a halogenated hydrocarbon solvent like methylene chloride ($CH_2Cl_2$, DCM) at ambient temperature, as shown in step b. Tertiary alcohols like the compound of Formula 1.4 can be prepared by treating a solution of an appropriately substituted ketone, such as the ketone of Formula 1.3, in a polar aprotic solvent like THF with a nucleophile such as a Grignard reagent, for example tert-butylmagnesium chloride ($^tBuMgCl$), at a reduced temperature of about −78° C., as shown in step c. Compounds like the compound of Formula 1.6, wherein $R_1$, $R_2$, $R_3$, $R_4$, $R_5$, $R_6$, $R_7$, $R_8$, and Z are as originally defined, can be prepared via a Suzuki coupling between an aryl bromide like the bromide of Formula 1.4 and an appropriately substituted boronic acid or boronate ester, for example the boronic acid of Formula 1.5, in the presence of an alkali carbonate base, such as potassium carbonate ($K_2CO_3$), and a palladium catalyst, such as tetrakis(triphenylphosphine)palladium(0) [$Pd(PPh_3)_4$], in a mixed solvent system, such as a polar solvent, for example N,N-dimethylformamide (DMF), dioxane or acetonitrile ($CH_3CN$), mixed with water, wherein the ratio of organic solvent to water in the composition is about 3:1, at an elevated temperature, achieved through conventional heating or microwave irradiation, of about 120° C., as shown in step d.

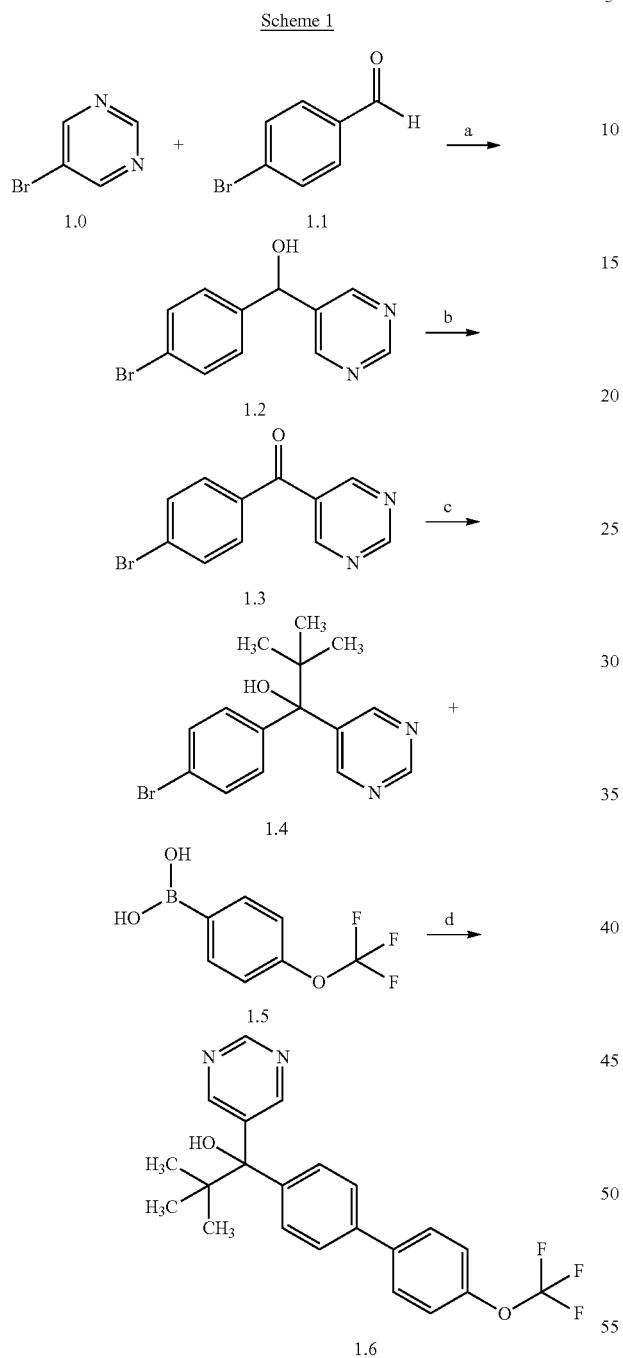

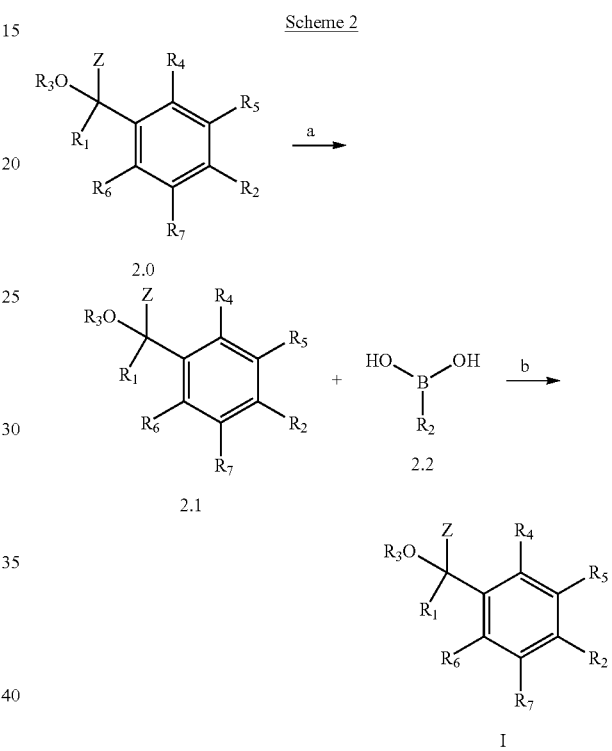

Formula 2.0, wherein $R_1$-$R_8$ and Z are as defined above, in a polar, aprotic solvent like THF with a strong base, for example sodium hydride (NaH), and an alkylating agent, for example iodomethane ($CH_3I$), at a temperature from about 0° C. to about 22° C., as shown in step a. Compounds of Formula I, wherein $R_1$-$R_8$ and Z are as originally defined, can be prepared by reacting compounds of Formula 2.1, wherein $R_1$-$R_8$ and Z are as defined above, with a boronic acid or boronate ester, for example the boronic acid of Formula 2.2, wherein $R_2$ is as originally defined, under the Suzuki cross coupling conditions described in Scheme 1, step d, as shown in step b.

Compounds of Formula I, wherein $R_1$-$R_8$, and Z are as originally defined, can be prepared as shown in Scheme 2, steps a-b from the appropriately substituted precursors, such as compounds of Formula 2.0. Compounds of Formula 2.0, wherein $R_1$, $R_4$-$R_8$, and Z are as originally defined and $R_2$ is halo, for example bromine, and $R_3$ is hydrogen, can be prepared according to the methods outlined in Scheme 1, steps a-c. Compounds of Formula 2.1, wherein $R_1$, $R_4$-$R_8$, and Z are as originally defined and $R_2$ is halo, for example bromine, and $R_3$ is as originally defined, for example alkyl, can be prepared by treating solutions of compounds of

EXAMPLES

Example 1

Preparation of 2,2-dimethyl-1-(pyrimidin-5-yl)-1-(4'-(trifluoromethoxy)-[1,1'-biphenyl]-4-yl)propan-1-ol (1)

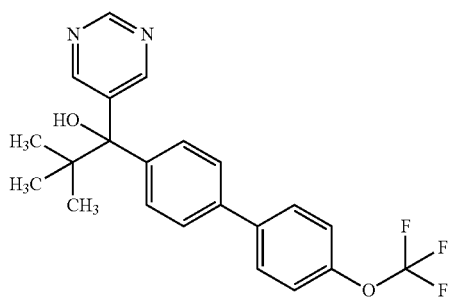 [SMILES: CC(C)(C)C(O)(c1ccc(-c2ccc(OC(F)(F)F)cc2)cc1)c1cncnc1]

Step A: Preparation of (4-bromophenyl)(pyrimidin-5-yl)methanol

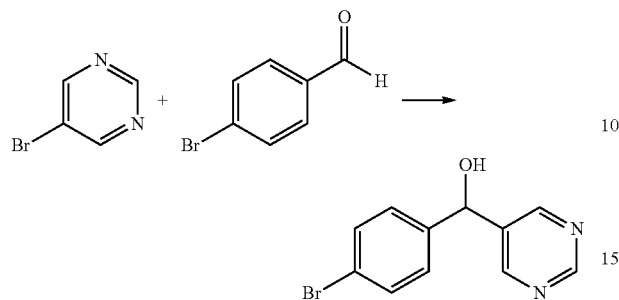

Followed an adapted procedure described by Frissen, A. E. et. al. (Tetrahedron (1989), 45(17), 5611-5620). To a solution of 5-bromopyrimidine (1.00 gram (g), 6.29 millimoles (mmol)) in a mixture of THF and Et$_2$O (1:1, 20 milliliters (mL) total) was added n-BuLi (2.5 Molar (M) solution in hexanes, 2.6 mL, 6.60 mmol) dropwise at −107° C. (ethanol (EtOH)/liquid nitrogen (N$_2$) bath) under an N$_2$ atmosphere, and the reaction mixture was stirred for 15 min (min) and then treated dropwise with a solution of 4-bromobenzaldehyde (1.16 g, 6.29 mmol) in THF (5 mL). The resulting light-yellow solution was slowly warmed to −67° C. over a period of 1.5 h (h), the cooling bath was removed, and the reaction mixture was allowed to warm to rt. The reaction mixture was quenched with saturated aqueous ammonium chloride (NH$_4$Cl), partitioned between ethyl acetate (EtOAc) and water, and the phases were separated. The aqueous phase was extracted with EtOAc (2×) and the combined organics were washed with saturated aqueous sodium chloride soloution (NaCl, brine), dried over sodium sulfate (Na$_2$SO$_4$), filtered, concentrated, and the residue purified by column chromatography (silica gel (SiO$_2$), 0→100% EtOAc in hexanes) to give the title compound (1.522 g, 91%) as a white crystalline solid: $^1$H NMR (400 MHz, CDCl$_3$) δ 9.08 (s, 1H), 8.68 (d, J=0.7 Hz, 2H), 7.56-7.47 (m, 2H), 7.26-7.22 (m, 2H), 5.85 (d, J=3.3 Hz, 1H), 3.15 (d, J=3.4 Hz, 1H); $^{13}$C NMR (126 MHz, CDCl$_3$) δ 157.8, 155.2, 140.9, 136.3, 132.2, 128.2, 122.6, 71.9; ESIMS m/z 266 ([M+H]$^+$).

Step B: Preparation of (4-bromophenyl)(pyrimidin-5-yl)methanone

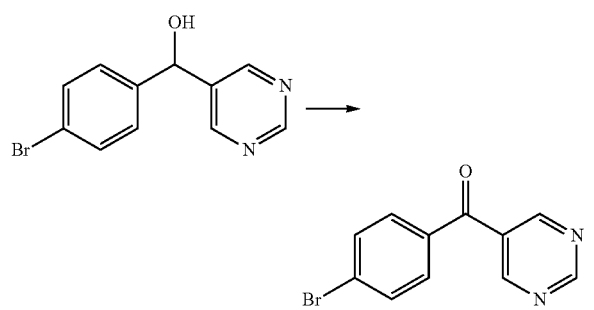

To a solution of (4-bromophenyl)(pyrimidin-5-yl)methanol (0.785 g, 2.96 mmol) in CH$_2$Cl$_2$ (12 mL) was added MnO$_2$ (2.57 g, 29.6 mmol) and the resulting suspension was stirred at rt overnight. The reaction mixture was filtered through a pad of Celite® rinsing with CH$_2$Cl$_2$ (50 mL) and the filtrate was concentrated to afford the title compound (0.770 g, 99%) as a yellow solid: $^1$H NMR (400 MHz, CDCl$_3$) δ 9.41 (s, 1H), 9.09 (s, 2H), 7.70 (s, 4H); $^{13}$C NMR (126 MHz, CDCl$_3$) δ 191.5, 160.9, 157.6, 134.5, 132.3, 131.3, 130.6, 129.3; ESIMS m/z 264 ([M+H]$^+$).

Step C: Preparation of 1-(4-bromophenyl)-2,2-dimethyl-1-(pyrimidin-5-yl)propan-1-ol

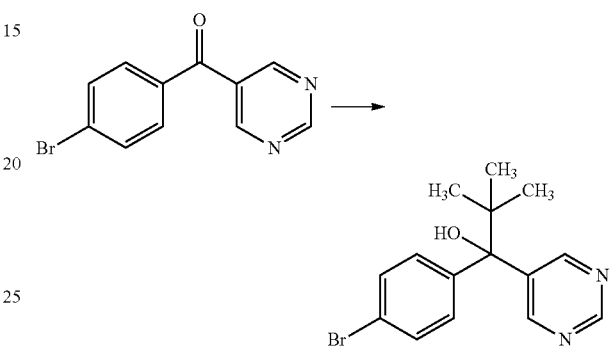

To a solution of (4-bromophenyl)(pyrimidin-5-yl)methanone (0.357 g, 1.36 mmol) in THF (3 mL) was added $^t$BuMgCl (1.0 M solution in THF, 2.7 mL, 2.70 mmol) dropwise at −78° C. and the reaction mixture was stirred at −78° C. for 1.5 h. The reaction mixture was quenched with saturated aqueous NH$_4$Cl, partitioned between EtOAc and water, and the phases separated. The aqueous phase was extracted with additional EtOAc (2×) and the combined organics were washed with brine, dried over Na$_2$SO$_4$, filtered, concentrated, and the residue purified by column chromatography (SiO$_2$, 0→100% EtOAc in hexanes) to give the title compound (0.220 g, 51%) as a white solid: $^1$H NMR (400 MHz, CDCl$_3$) δ 9.05 (s, 1H), 8.88 (s, 2H), 7.50-7.39 (m, 2H), 7.34-7.26 (m, 2H), 2.59 (s, 1H), 1.15 (s, 9H); $^{13}$C NMR (126 MHz, CDCl$_3$) δ 156.8, 156.4, 142.8, 138.5, 130.9, 129.9, 121.7, 80.8, 39.3, 26.9; ESIMS m/z 322 ([M+H]$^+$).

Step D: Preparation of 2,2-dimethyl-1-(pyrimidin-5-yl)-1-(4'-(trifluoromethoxy)-[1,1'-biphenyl]-4-yl)propan-1-ol (1)

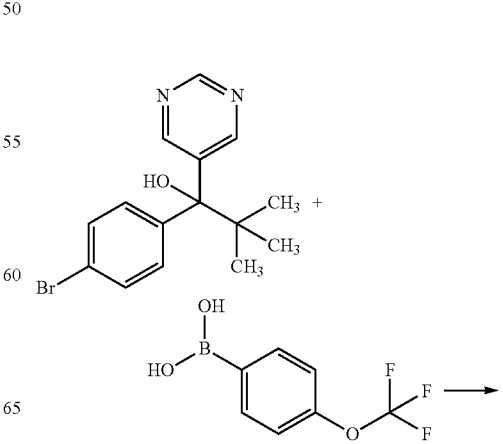

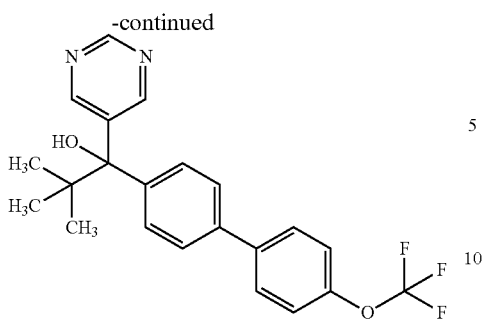

To a 5 mL microwave reactor vial were added 1-(4-bromophenyl)-2,2-dimethyl-1-(pyrimidin-5-yl)propan-1-ol (0.055 g, 0.171 mmol), (4-(trifluoromethoxy)phenyl)boronic acid (0.046 g, 0.223 mmol), K$_2$CO$_3$ (0.083 g, 0.60 mmol), DMF (0.40 mL) and water (0.10 mL), and the mixture was purged with N$_2$ for 5 min. To the mixture was added Pd(PPh$_3$)$_4$ (0.002 g, 0.0002 mmol) and the vessel was capped, placed in a Biotage Initiator microwave reactor for 1 h at 120° C., with external IR-sensor temperature monitoring from the side of the vessel. The reaction mixture was filtered through a pad of Celite® rinsing with EtOAc (30 mL) and the filtrate was washed successively with water (3×) and brine (1×), dried over Na$_2$SO$_4$, filtered, concentrated, and the residue purified by column chromatography (SiO$_2$, 0→60% EtOAc in hexanes) to give the title compound (0.064 g, 93%) as a white solid: See Table 2 for characterization data.

Example 2

Preparation of 5-(1-(3-fluoro-4'-(trifluoromethoxy)-[1,1'-biphenyl]-4-yl)-1-methoxy-2,2-dimethylpropyl)pyrimidine (79)

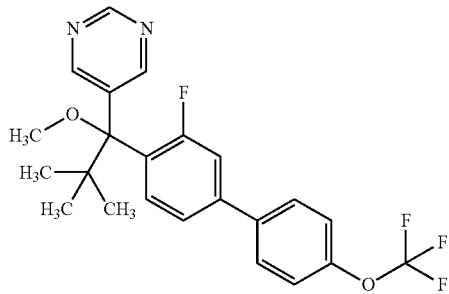 [SMILES: COC(c1cncnc1)(c1ccc(-c2ccc(OC(F)(F)F)cc2)cc1F)C(C)(C)C]

Step A: Preparation of 5-(1-(4-bromo-2-fluorophenyl)-1-methoxy-2,2-dimethylpropyl)-pyrimidine

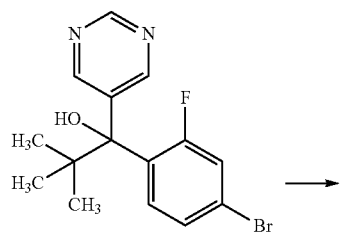

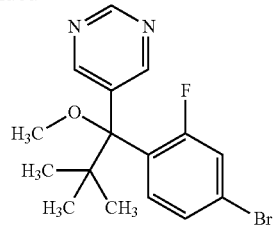

To an oven-dried scintillation vial were added 1-(4-bromo-2-fluorophenyl)-2,2-dimethyl-1-(pyrimidin-5-yl)propan-1-ol (0.300 g, 0.88 mmol) and THF (4.5 mL), and the resulting solution was cooled to 0° C. and treated with NaH (0.071 g, 1.77 mmol, 60% dispersion in mineral oil) followed by iodomethane (CH$_3$I; 0.314 g, 2.21 mmol). The reaction mixture was allowed to slowly warm to rt overnight and was quenched with saturated aqueous NH$_4$Cl, diluted with water and EtOAc, and the phases separated. The aqueous phase was extracted with EtOAc (2×) and the combined organics were washed with brine, dried over sodium sulfate, filtered, concentrated, and the residue purified by column chromatography (SiO$_2$, 0→40% EtOAc in hexanes) to give the title compound (0.274 g, 88%) as an off-white solid: $^1$H NMR (400 MHz, CDCl$_3$) δ 9.10 (s, 1H), 8.80 (d, J=1.1 Hz, 2H), 7.58 (t, J=8.4 Hz, 1H), 7.38 (ddd, J=8.5, 2.0, 0.6 Hz, 1H), 7.20 (dd, J=11.2, 2.0 Hz, 1H), 3.04 (s, 3H), 1.14 (s, 9H); $^{19}$F NMR (376 MHz, CDCl$_3$) δ −96.60; ESIMS m/z 354 ([M+H]$^+$).

Step B: Preparation of 5-(1-(3-fluoro-4'-(trifluoromethoxy)-[1,1'-biphenyl]-4-yl)-1-methoxy-2,2-dimethylpropyl)pyrimidine (79)

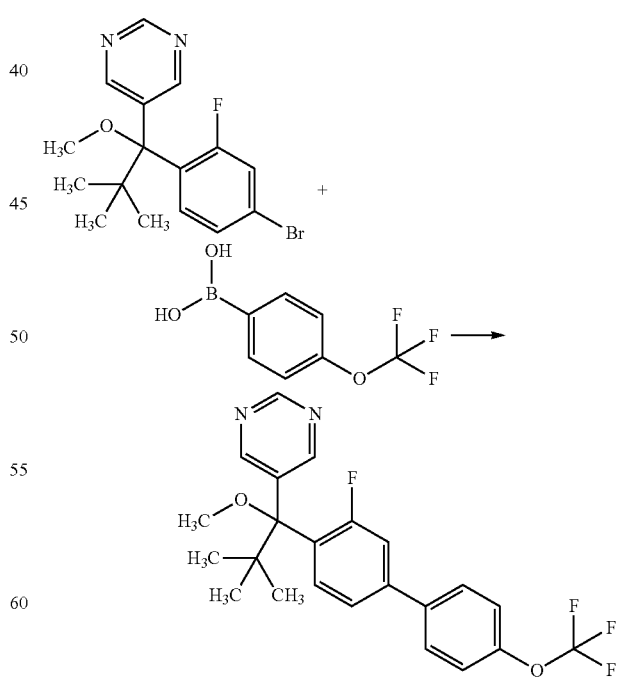

To a 5 mL microwave reactor vial were added 5-(1-(4-bromo-2-fluorophenyl)-1-methoxy-2,2-dimethylpropyl)pyrimidine (0.030 g, 0.085 mmol), (4-(trifluoromethoxy)phenyl)boronic acid (0.035 g, 0.17 mmol), K₂CO₃ (0.041 g, 0.60 mmol), DMF (0.40 mL), and water (0.10 mL), and the mixture was purged with N₂ for 5 min. To the mixture was added Pd(PPh₃)₄ (0.001 g, 0.00008 mmol) and the vessel was capped, placed in a Biotage Initiator microwave reactor for 30 min at 120° C., with external IR-sensor temperature monitoring from the side of the vessel. The cooled reaction mixture was partitioned between water and EtOAc and the phases were separated. The aqueous phase was extracted with ethyl acetate (2×) and the combined organics were washed successively with water (3×) and brine (1x), dried over sodium sulfate, filtered, concentrated, and the residue purified by column chromatography (SiO₂, 040% EtOAc in hexanes) to give the title compound (0.36 g, 98%) as a clear, viscous oil: See Table 2 for characterization data.

Example 3

Preparation of 2,2-dimethyl-1-(2-methyl-4-(5-(trifluoromethoxy)pyridin-2-yl)phenyl)-1-(pyrimidin-5-yl)propan-1-ol (98)

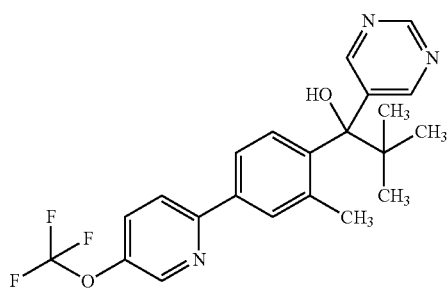 [SMILES: Cc1cc(-c2ccc(OC(F)(F)F)cn2)ccc1C(O)(c1cncnc1)C(C)(C)C]

Step A: Preparation of 2,2-dimethyl-1-(2-methyl-4-(4,4,5,5-tetramethyl-1,3,2-dioxaborolan-2-yl)phenyl)-1-(pyrimidin-5-yl)propan-1-ol

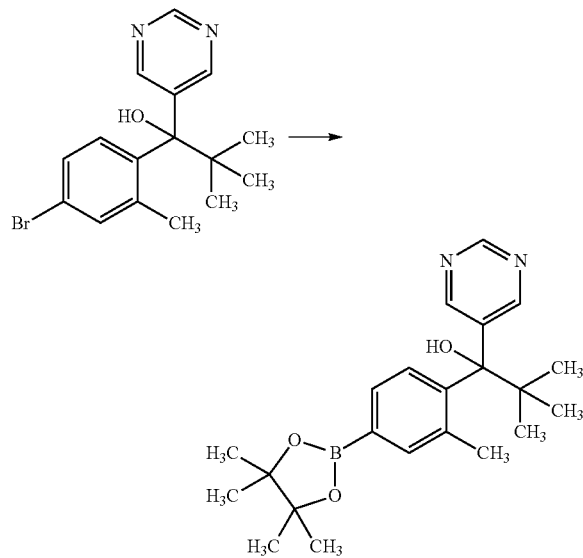

1-(4-Bromo-2-methylphenyl)-2,2-dimethyl-1-(pyrimidin-5-yl)propan-1-ol (0.219 g, 0.653 mmol, 1.0 equiv), 4,4,4',4',5,5,5',5'-octamethyl-2,2'-bi(1,3,2-dioxaborolane) (0.216 g, 0.849 mmol, 1.3 equiv), Pd(dppf)Cl₂ (0.048 g, 0.065 mmol, 0.1 equiv) and potassium acetate (0.128 g, 1.31 mmol, 2.0 equiv) were placed in an oven-dried scintillation vial and purged with nitrogen for five min. 1,4-dioxane (3.3 mL) was added and the reaction was heated at 90° C. overnight. The reaction was cooled to rt and diluted with ethyl acetate and water, then the layers were separated. The aqueous layer was extracted with ethyl acetate (×2) and the combined organics were washed with brine, dried over sodium sulfate, filtered and concentrated. Purification by silica gel chromatography eluting with a 0 to 40% ethyl acetate gradient afforded 0.233 g (0.609 mmol, 93% yield) of the title compound as a white powder. $^1$H NMR (400 MHz, CDCl₃) δ 8.96 (s, 1H), 8.53 (s, 2H), 7.88 (d, J=8.0 Hz, 1H), 7.62 (dd, J=7.9, 1.5 Hz, 1H), 7.54 (d, J=1.4 Hz, 1H), 2.83 (s, 1H), 1.92 (s, 3H), 1.33 (s, 12H), 1.21 (s, 9H); $^{13}$C NMR (101 MHz, CDCl₃) δ 156.3, 156.0, 144.4, 140.5, 138.2, 137.7, 130.9, 127.7, 83.9, 81.3, 39.7, 24.8, 24.6, 22.6; ESIMS m/z 383 [M+H]⁺.

Step B: Preparation of 2,2-dimethyl-1-(2-methyl-4-(5-(trifluoromethoxy)pyridin-2-yl)phenyl)-1-(pyrimidin-5-yl)propan-1-ol (98)

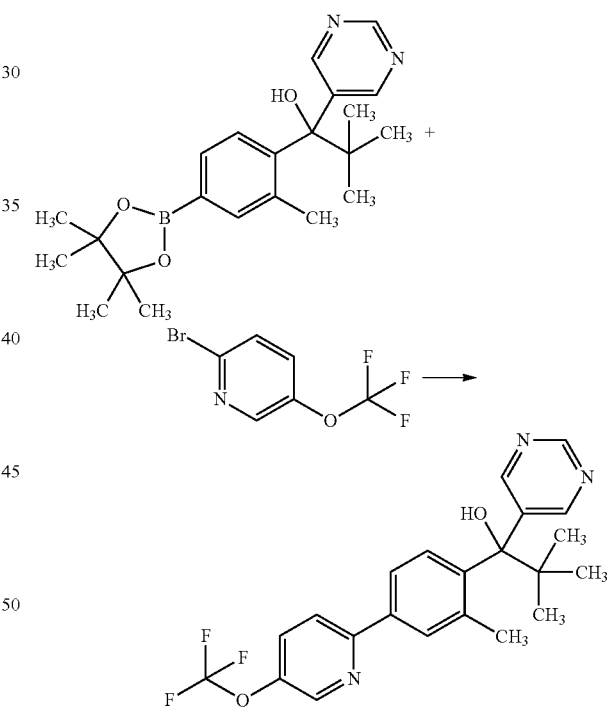

2,2-dimethyl-1-(2-methyl-4-(4,4,5,5-tetramethyl-1,3,2-dioxaborolan-2-yl)phenyl)-1-(pyrimidin-5-yl)propan-1-ol (0.060 g, 0.157 mmol, 1.0 equiv), 2-bromo-5-(trifluoromethoxy)pyridine (0.076 g, 0.314 mmol, 2.0 equiv) and potassium carbonate (0.065 g, 0.471 mmol, 3.0 equiv) were placed in a 2 mL microwave vial and DMF and water (0.400 mU0.100 mL) were added. The vial was purged with nitrogen for 5 min and tetrakis(triphenylphosphine)palladium (0) (1.8 mg, 0.00157 mmol, 0.01 equiv) was added. The reaction was run in a Biotage microwave reactor for 30 min at 120° C. The reaction mixture was transferred to a scintillation vial and solvents were removed in vacuo. Purification by silica gel chromatography eluting with a 50% ethyl acetate/hexane gradient afforded 61 mg (0.146 mmol, 93% yield) of the title compound as a white solid. ¹H NMR (400 MHz, CDCl₃) δ 9.06 (d, J=2.1 Hz, 1H), 8.64 (d, J=1.8 Hz, 2H), 8.60 (d, J=2.7 Hz, 1H), 8.02 (d, J=8.3 Hz, 1H), 7.82-7.72 (m, 3H), 7.65-7.59 (m, 1H), 2.47 (s, 1H), 2.04 (s, 3H), 1.27 (s, 9H); ¹⁹F NMR (376 MHz, CDCl₃) δ −58.1; ESIMS m/z 418 [M+H]⁺.

Example 4

Preparation of 2,2-dimethyl-1-(pyrimidin-5-yl)-1-(4'-(trifluoromethoxy)-3-(trifluoromethyl)-[1,1'-biphenyl]-4-yl)propan-1-ol (109)

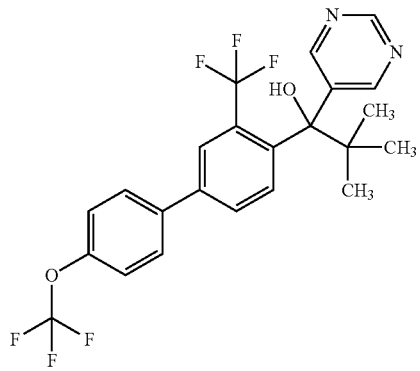 [SMILES: CC(C)(C)C(O)(c1cncnc1)c1ccc(-c2ccc(OC(F)(F)F)cc2)cc1C(F)(F)F]

Step A: Preparation of 1-(4-bromo-2-(trifluoromethyl)phenyl)-2,2-dimethylpropan-1-one

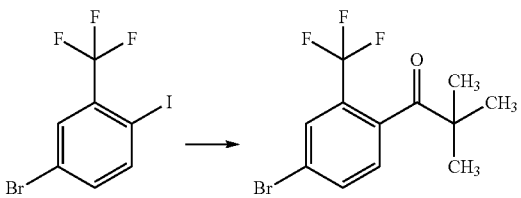 [SMILES: FC(F)(F)c1cc(Br)ccc1I ; CC(C)(C)C(=O)c1ccc(Br)cc1C(F)(F)F]

4-Bromo-1-iodo-2-(trifluoromethyl)benzene(2.0 g, 5.70 mmol, 1.0 equiv) was placed in an oven-dried scintillation vial and dissolved in THF (11.4 mL). Isopropylmagenesium chloride lithium chloride complex (5.7 mL of a 1.3 M solution in ether, 7.41 mmol, 1.3 equiv) was added, and the resultant dark brown solution was stirred at rt for 2 h. The Grignard solution was then added dropwise to a solution of trimethylacetyl chloride (0.893 g, 7.41 mmol, 1.3 equiv in 11 mL THF) and the reaction was stirred overnight. The reaction was quenched carefully with sat. NH₄Cl, diluted with ethyl acetate and water, and the layers were separated. The aqueous layer was extracted with ethylacetate (×1) and the combined organics were washed with brine, dried over sodium sulfate, filtered and concentrated. Purification by silica gel chromatography eluting with a 5% ethyl acetate/hexane gradient afforded 1.05 g (3.40 mmol, 60% yield) of the title compound as a yellow oil. ¹H NMR (400 MHz, CDCl₃) δ 7.83 (d, J=1.9 Hz, 1H), 7.69 (ddd, J=8.3, 1.9, 0.7 Hz, 1H), 7.17 (d, J=8.2 Hz, 1H), 1.25 (s, 9H); ¹³C NMR (126 MHz, CDCl₃) δ 211.1, 138.3, 134.3, 130.1 (q, J=4.5 Hz), 126.9, 123.7, 122.8, 121.5, 44.7, 27.6; ESIMS m/z 310 [M+H]⁺.

Step B: Preparation of 1-(4-bromo-2-(trifluoromethyl)phenyl)-2,2-dimethyl-1-(pyrimidin-5-yl)propan-1-ol

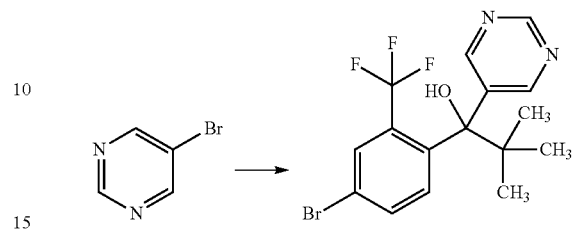

5-Bromopyrimidine (1.17 g, 7.38 mmol, 1.2 equiv) was placed in an oven-dried 50-mL round-bottomed flask and dissolved in THF/Et₂O (15.4 mL/15.4 mL). The solution was cooled to −105° C. (ethanol/liquid N₂ bath) and n-butyllithium (3 mL of 2.5 M solution in hexanes, 7.38 mmol, 1.2 equiv) was added dropwise under N₂. After stirring for 15 min, a solution 1-(4-bromo-2-(trifluoromethyl)phenyl)-2,2-dimethylpropan-1-one (1.9 g, 6.15 mmol, 1.0 equiv in 5 mL THF) is added dropwise. The resultant light yellow solution is allowed to warm slowly for 1.5 h (bath reaches −63° C.) and the bath is removed and the reaction is allowed to warm to rt. The reaction is quenched with saturated ammonium chloride and diluted with ethyl acetate and water, layers separated. The aqueous is extracted with ethyl acetate (×2) and the combined organics are washed with brine, dried over sodium sulfate, filtered and concentrated. Purification by silica gel chromatography eluting with a 0 to 100% ethyl acetate/hexane gradient afforded 1.040 g (2.67 mmol, 44% yield) of the title compound as an off-white solid solid. ¹H NMR (400 MHz, CDCl₃) δ 9.04 (s, 1H), 8.65 (s, 2H), 7.95 (d, J=2.3 Hz, 1H), 7.84 (d, J=8.6 Hz, 1H), 7.68 (dd, J=8.7, 2.3 Hz, 1H), 2.81 (d, J=1.0 Hz, 1H), 1.21 (s, 9H); ¹⁹F NMR (376 MHz, CDCl₃) δ −54.6. ESIMS m/z 390 [M+H]⁺.

Step C: Preparation of 2,2-dimethyl-1-(pyrimidin-5-yl)-1-(4'-(trifluoromethoxy)-3-(trifluoromethyl)-[1,1'-biphenyl]-4-yl)propan-1-ol (109)

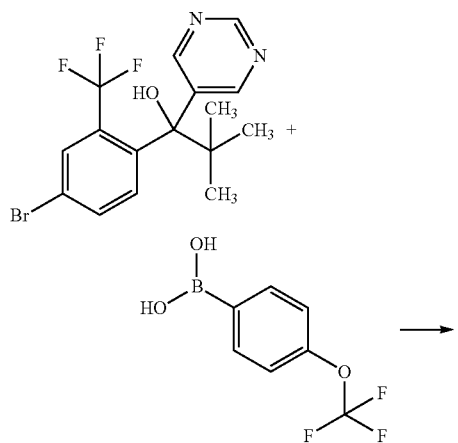

-continued

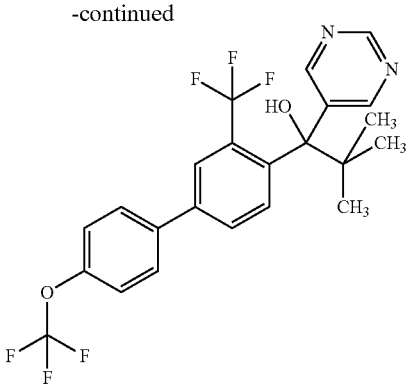

1-(4-Bromo-2-(trifluoromethyl)phenyl)-2,2-dimethyl-1-(pyrimidin-5-yl)propan-1-ol (0.050 g, 0.128 mmol, 1.0 equiv), (4-(trifluoromethoxy)phenyl)boronic acid (0.034 g, 0.167 mmol, 1.3 equiv) and potassium carbonate (0.062 g, 0.450 mmol, 3.5 equiv) were placed in a 2 mL microwave vial and DMF/water (0.400 mL/0.100 mL) were added.

Tetrakis(triphenylphosphine)palladium (0) (1.5 mg, 0.00128 mmol, 0.01 equiv) was added and the reaction was run in a Biotage microwave reactor for 30 min at 120° C. The reaction mixture was transferred to a scintillation vial and solvents were removed in vacuo. Purification by silica gel chromatography eluting with 0 to 50% ethyl acetate/hexane gradient afforded 60 mg (0.128 mmol, 99% yield) of the title compound as an off-white foam. $^1$H NMR (400 MHz, CDCl$_3$) δ 9.08 (s, 1H), 8.73 (s, 2H), 8.08 (d, J=8.4 Hz, 1H), 8.00 (q, J=3.2 Hz, 1H), 7.73 (dd, J=8.4, 2.2 Hz, 1H), 7.64-7.59 (m, 2H), 7.34 (dq, J=8.7, 1.0 Hz, 2H), 2.70 (d, J=1.0 Hz, 1H), 1.26 (s, 9H); $^{19}$F NMR (376 MHz, CDCl$_3$) δ −54.3, −57.8; ESIMS m/z 471 [M+H]$^+$.

Biology Examples

Example A

Evaluation of Fungicidal Activity: Leaf Blotch of Wheat (*Mycosphaerella graminicola*; Anam TABLE 1-continued Structure and Preparation Method.

| Compound Number | Structure | Prepared According to Example |
|---|---|---|
| 2 | 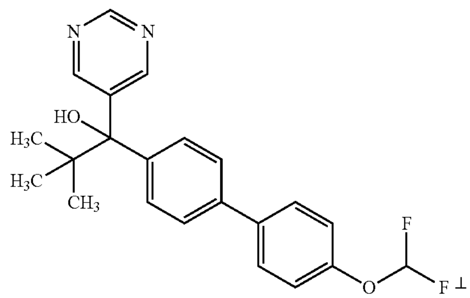 [SMILES: CC(C)(C)C(O)(c1ccc(-c2ccc(OC(F)F)cc2)cc1)c1cncnc1] | Prepared according to Example 1 using 2-(4-(difluoromethoxy)-phenyl)4,4,5,5-tetramethyl-1,3,2-dioxaborolane in D |
| 3 | 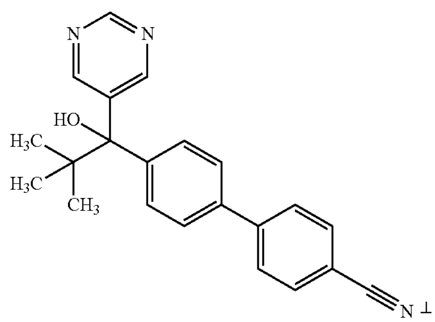 [SMILES: CC(C)(C)C(O)(c1ccc(-c2ccc(C#N)cc2)cc1)c1cncnc1] | Prepared according to Example 1 using (4-cyanophenyl)boronic acid in D |
| 4 | 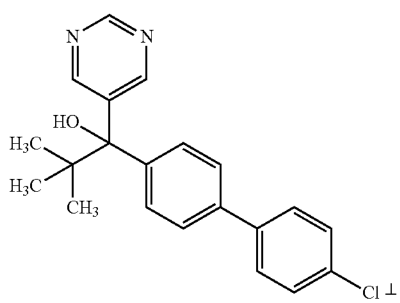 [SMILES: CC(C)(C)C(O)(c1ccc(-c2ccc(Cl)cc2)cc1)c1cncnc1] | Prepared according to Example 1 using (4-chlorophenyl)boronic acid in D |
| 5 | 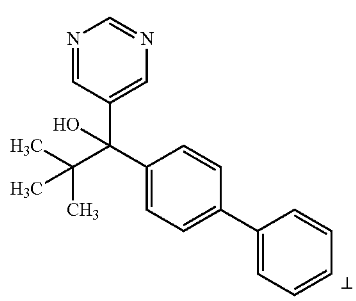 [SMILES: CC(C)(C)C(O)(c1ccc(-c2ccccc2)cc1)c1cncnc1] | Prepared according to Example 1 using phenylboronic acid in D |

TABLE 1-continued

Structure and Preparation Method.

| Compound Number | Structure | Prepared According to Example |
|---|---|---|
| 6 | 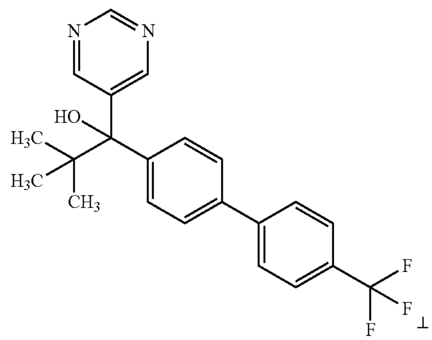 [SMILES: CC(C)(C)C(O)(c1ccc(-c2ccc(C(F)(F)F)cc2)cc1)c1cncnc1] | Prepared according to Example 1 using (4-(trifluoromethyl)-phenyl)boronic acid in D |
| 7 | 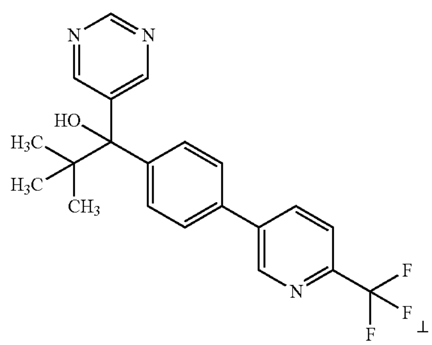 [SMILES: CC(C)(C)C(O)(c1ccc(-c2ccc(C(F)(F)F)nc2)cc1)c1cncnc1] | Prepared according to Example 1 using (6-(trifluoromethyl)-pyridin-3-yl)boronic acid in D |
| 8 | 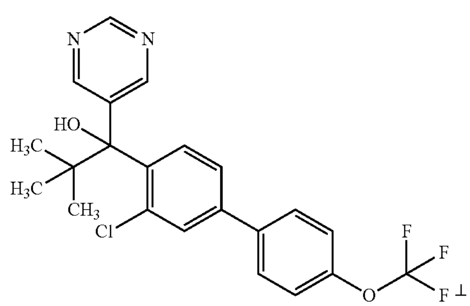 | Prepared according to Example 1 using 4-bromo-2-chlorobenzaldehyde in A |
| 9 | 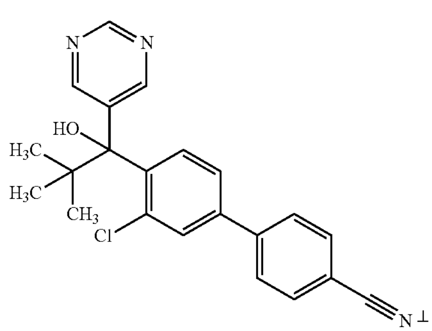 | Prepared according to Example 1 using 4-bromo-2-chloro benzaldehyde in A and (4-cyanophenyl)boronic acid in D |

TABLE 1-continued

Structure and Preparation Method.

| Compound Number | Structure | Prepared According to Example |
|---|---|---|
| 10 | 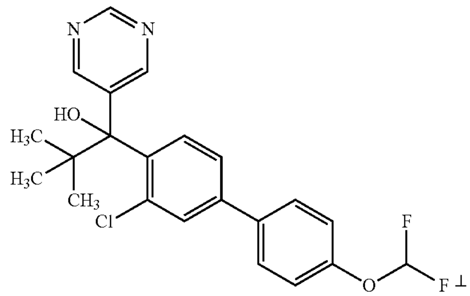 | Prepared according to Example 1 using 4-bromo-2-chlorobenzaldehyde in A and 2-(4-(difluoromethoxy)phenyl)-4,4,5,5-tetramethyl-1,3,2-dioxaborolane in D |
| 11 | 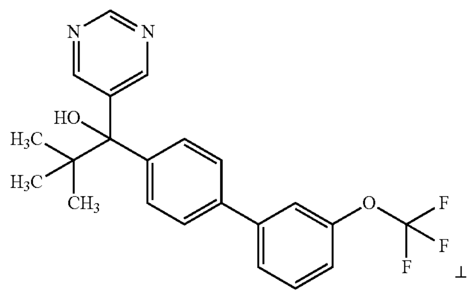 [SMILES: CC(C)(C)C(O)(c1ccc(-c2cccc(OC(F)(F)F)c2)cc1)c1cncnc1] | Prepared according to Example 1 using (3-(trifluoromethoxy)phenyl)boronic acid in D |
| 12 | 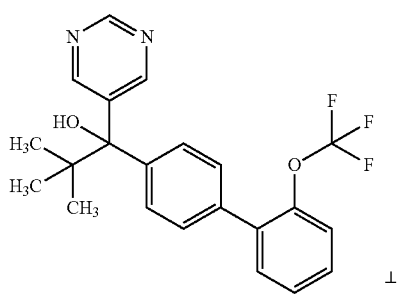 [SMILES: CC(C)(C)C(O)(c1ccc(-c2ccccc2OC(F)(F)F)cc1)c1cncnc1] | Prepared according to Example 1 using ((2-(trifluoromethoxy)phenyl)boronic acid in D |
| 13 | 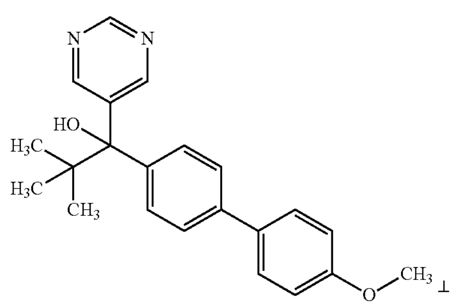 [SMILES: COc1ccc(-c2ccc(C(O)(c3cncnc3)C(C)(C)C)cc2)cc1] | Prepared according to Example 1 using (4-methoxyphenyl)-boronic acid in D |
| 14 | 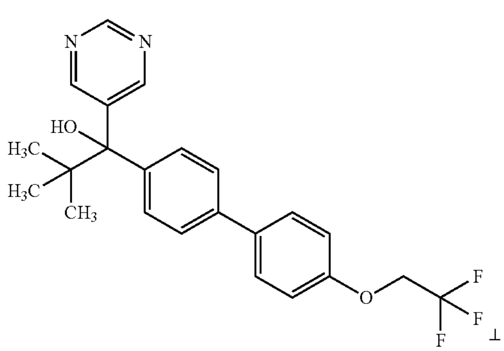 | Prepared according to Example 1 using ((4-(2,2,2-trifluoroethoxy)phenyl)boronic acid in D |

TABLE 1-continued

Structure and Preparation Method.

| Compound Number | Structure | Prepared According to Example |
|---|---|---|
| 15 | 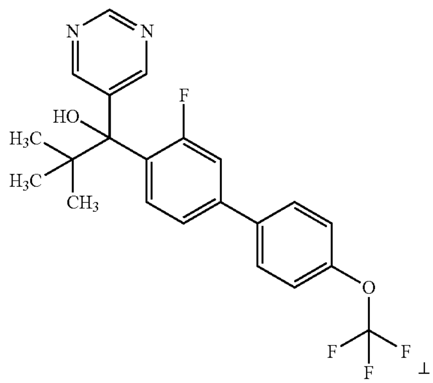 [SMILES: CC(C)(C)C(O)(c1cncnc1)c1ccc(-c2ccc(OC(F)(F)F)cc2)cc1F] | Prepared according to Example 1 using 4-bromo-2-fluorobenzaldehyde in A |
| 16 | 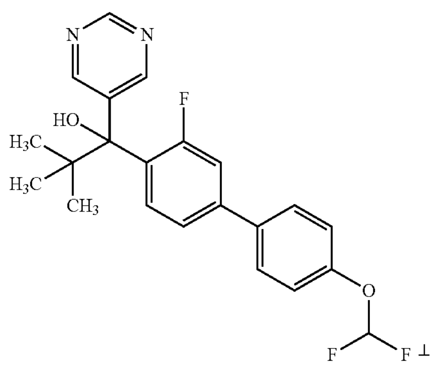 [SMILES: CC(C)(C)C(O)(c1cncnc1)c1ccc(-c2ccc(OC(F)F)cc2)cc1F] | Prepared according to Example 1 using 4-bromo-2-fluorobenzaldehyde in A and 2-(4-(difluoromethoxy)phenyl)-4,4,5,5-tetramethyl-1,3,2-dioxaborolane in D |
| 17 | 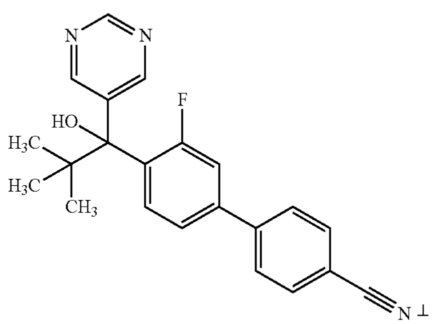 | Prepared according to Example 1 using 4-bromo-2-fluorobenzaldehyde in A and (4-cyanophenyl)boronic acid in D |
| 18 | 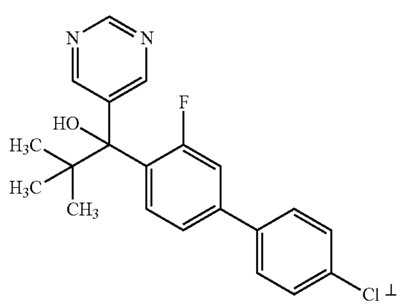 [SMILES: CC(C)(C)C(O)(c1cncnc1)c1ccc(-c2ccc(Cl)cc2)cc1Cl] | Prepared according to Example 1 using 4-bromo-2-fluorobenzaldehyde in (4-chlorophenyl)boronic acid in D |

TABLE 1-continued

Structure and Preparation Method.

| Compound Number | Structure | Prepared According to Example |
|---|---|---|
| 19 | 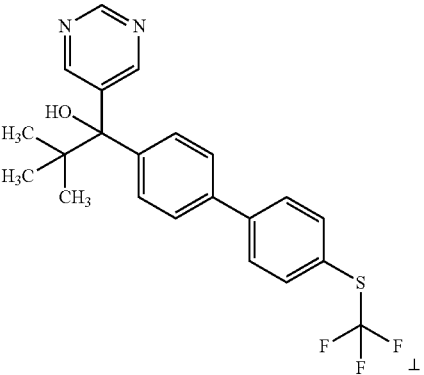 | Prepared according to Example 1 using 4,4,5,5-tetramethyl-2-(4-((trifluoro-methyl)thio)phenyl)-1,3,2-dioxaborolane in D |
| 20 | 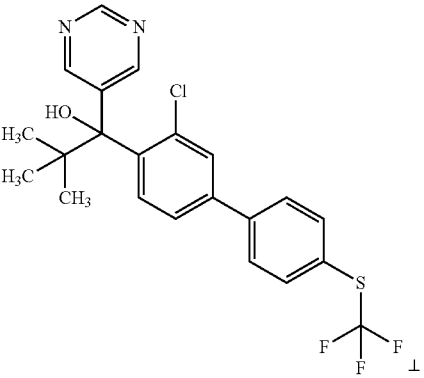 | Prepared according to Example 1 using 4-bromo-2-chlorobenzaldehyde in A and 4,4,5,5-tetramethyl-2-(4-((trifluoromethyl)thio)phenyl)-1,3,2-dioxaborolane in D |
| 21 | 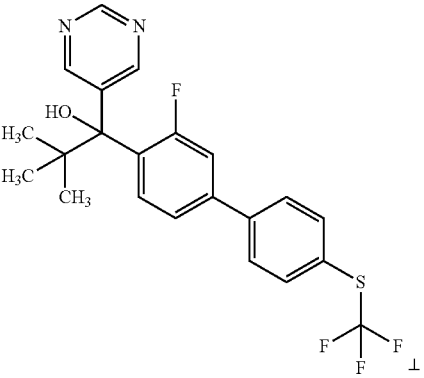 | Prepared according to Example 1 using 4-bromo-2-fluorobenzaldehyde in A and 4,4,5,5-tetramethyl-2-(4-((trifluoromethyl)thio)phenyl)-1,3,2-dioxaborolane in D |
| 22 | 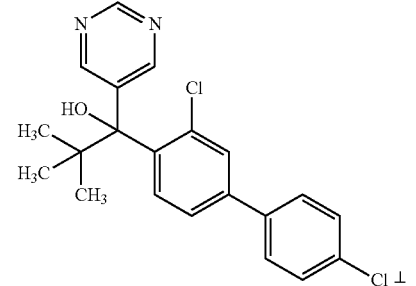 | Prepared according to Example 1 using 4-bromo-2-chlorobenzaldehyde in A and (4-chlorophenyl)boronic acid in D |

TABLE 1-continued

Structure and Preparation Method.

| Compound Number | Structure | Prepared According to Example |
|---|---|---|
| 23 | 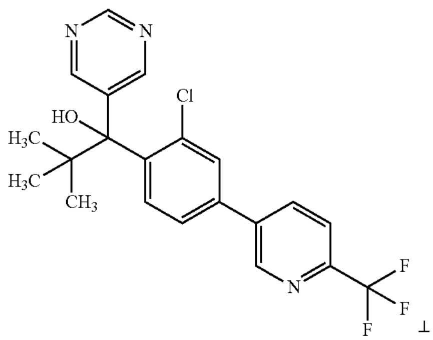 | Prepared according to Example 1 using 4-bromo-2-chlorobenzaldehyde in A and (6-(trifluoromethyl)pyridin-3-yl)boronic acid in D |
| 24 | 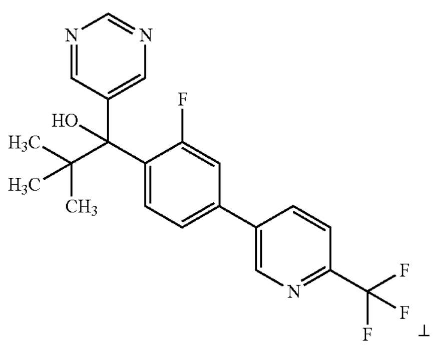 | Prepared according to Example 1 using 4-bromo-2-flurobenzaldehyde in A and (6-(trifluoromethyl)pyridin-3-yl)boronic acid in D |
| 25 | 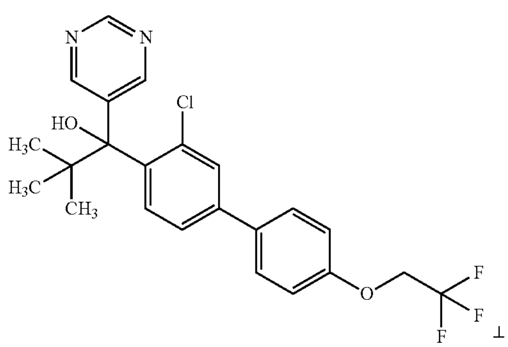 [SMILES: CC(C)(C)C(O)(c1cncnc1)c1ccc(-c2ccc(OCC(F)(F)F)cc2)cc1Cl] | Prepared according to Example 1 using 4-bromo-2-chlorobenzaldehyde in A (4-(2,2,2-trifluoroethoxy)-phenyl)boronic acid in D |
| 26 | 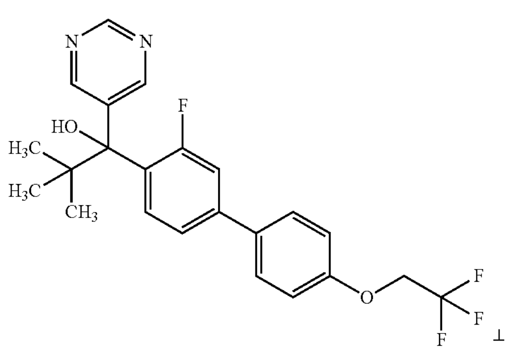 [SMILES: CC(C)(C)C(O)(c1cncnc1)c1ccc(-c2ccc(OCC(F)(F)F)cc2)cc1F] | Prepared according to Example 1 using 4-bromo-2-fluorobenzaldehyde in A and (4-(2,2,2-trifluoroethoxy)-phenyl)boronic acid in D |

TABLE 1-continued

Structure and Preparation Method.

| Compound Number | Structure | Prepared According to Example |
|---|---|---|
| 27 | 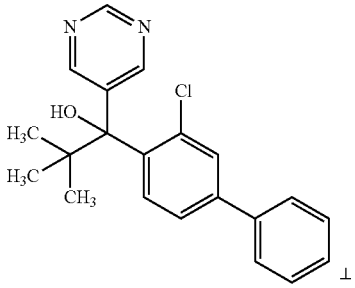 [SMILES: CC(C)(C)C(O)(c1cncnc1)c1ccc(-c2ccccc2)cc1F] | Prepared according to Example 1 using 4-bromo-2-chloro benzaldehyde in A and phenylboronic acid in D |
| 28 | 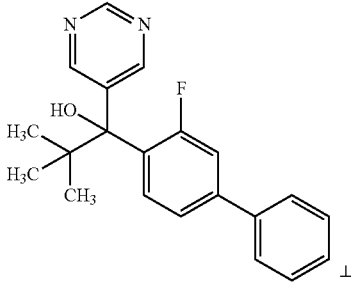 | Prepared according to Example 1 using 4-bromo-2-fluoro benzaldehyde in A and phenylboronic acid in D |
| 29 | 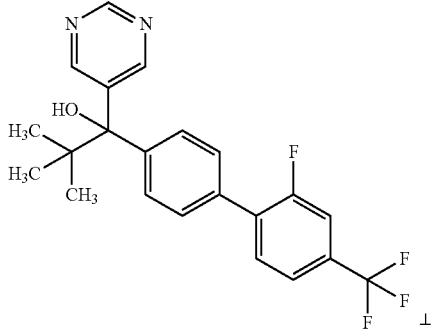 [SMILES: CC(C)(C)C(O)(c1ccc(-c2ccc(C(F)(F)F)cc2F)cc1)c1cncnc1] | Prepared according to Example 1 using (2-fluoro-4-(trifluoromethyl)phenyl)boronic acid in D |
| 30 | 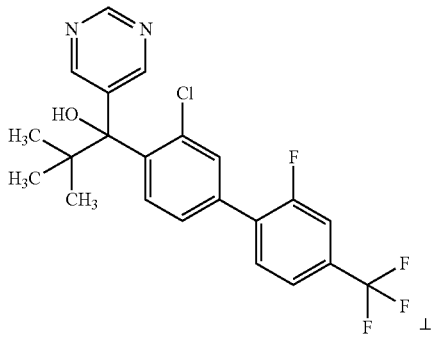 [SMILES: CC(C)(C)C(O)(c1cncnc1)c1ccc(-c2ccc(C(F)(F)F)cc2F)cc1Cl] | Prepared according to Example 1 using 4-bromo-2-chloro benzaldehyde in A and 2-fluoro-4-(trifluoromethyl)phenyl-boronic acid in D |

TABLE 1-continued

Structure and Preparation Method.

| Compound Number | Structure | Prepared According to Example |
|---|---|---|
| 31 | 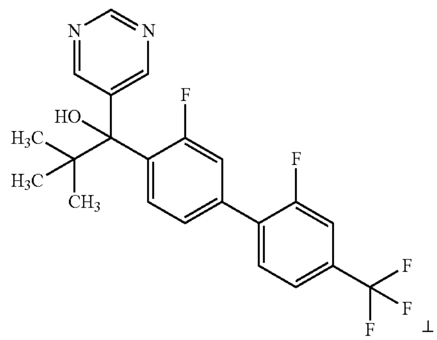 [SMILES: CC(C)(C)C(O)(c1cncnc1)c1ccc(-c2ccc(C(F)(F)F)cc2F)cc1F] | Prepared according to Example 1 using 4-bromo-2-fluoro benzaldehyde in A and 2-fluoro-4-(trifluoromethyl)phenyl)-boronic acid in D |
| 32 | 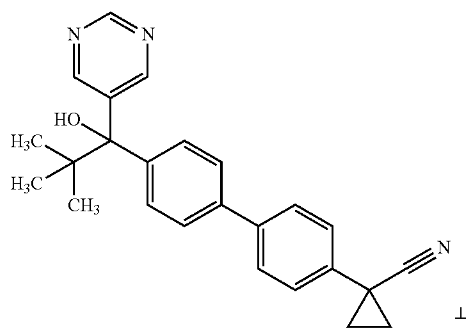 [SMILES: CC(C)(C)C(O)(c1ccc(-c2ccc(C3(C#N)CC3)cc2)cc1)c1cncnc1] | Prepared according to Example 1 using (4-(1-cyanocyclopropyl)phenyl)boronic acid in D |
| 33 | 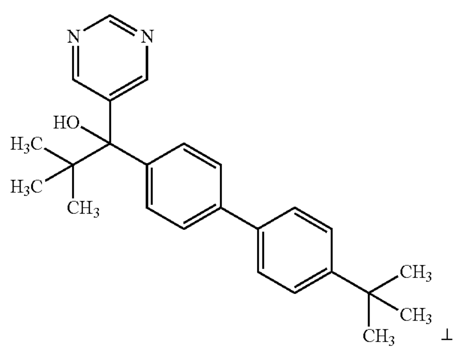 | Prepared according to Example 1 using (4-(tert-butyl)phenyl)-boronic acid in D |
| 34 | 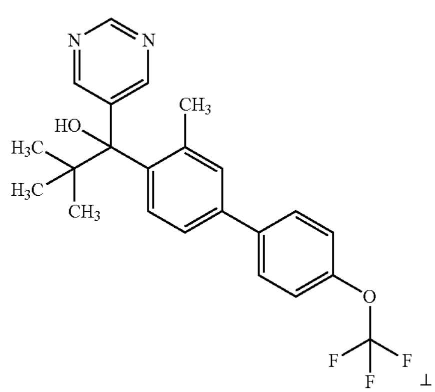 [SMILES: Cc1cc(-c2ccc(OC(F)(F)F)cc2)ccc1C(O)(c1cncnc1)C(C)(C)C] | Prepared according to Example 1 using 4-bromo-2-methyl benzaldehyde in A |

TABLE 1-continued

Structure and Preparation Method.

| Compound Number | Structure | Prepared According to Example |
|---|---|---|
| 35 | 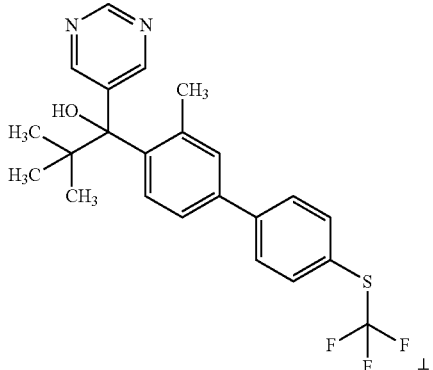 | Prepared according to Example 1 using 4-bromo-2-methyl benzaldehyde in A and 4,4,5,5-tetramethyl-2-(4-((trifluoromethyl)thio)phenyl)-1,3,2-dioxaborolane in D |
| 36 | 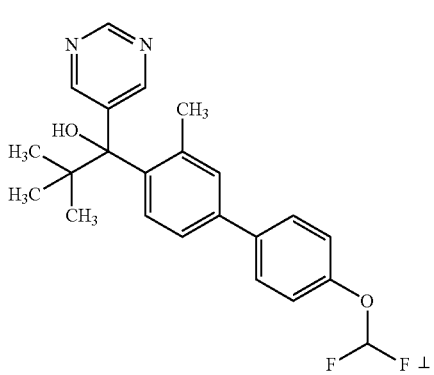 [SMILES: Cc1cc(-c2ccc(OC(F)F)cc2)ccc1C(O)(c1cncnc1)C(C)(C)C] | Prepared according to Example 1 using 4-bromo-2-methyl benzaldehyde in A and 2-(4-(difluoromethoxy)phenyl)-4,4,5,5-tetramethyl-1,3,2-dioxaborolane in D |
| 37 | 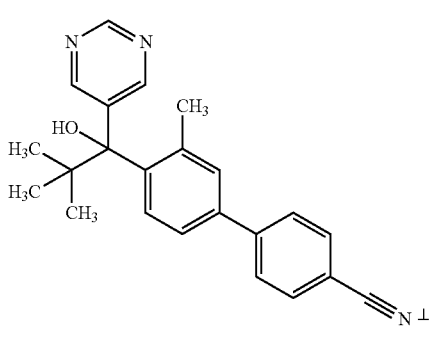 | Prepared according to Example 1 using 4-bromo-2-methyl benzaldehyde in A and (4-cyanophenyl)boronic acid in D |
| 38 | 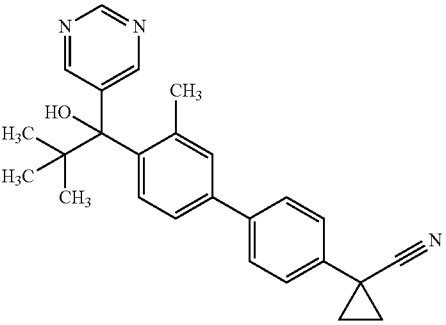 | Prepared according to Example 1 using 4-bromo-2-methyl benzaldehyde in A and (4-(1-cyanocyclopropyl)phenyl)boronic acid in D |

TABLE 1-continued

Structure and Preparation Method.

| Compound Number | Structure | Prepared According to Example |
|---|---|---|
| 39 | 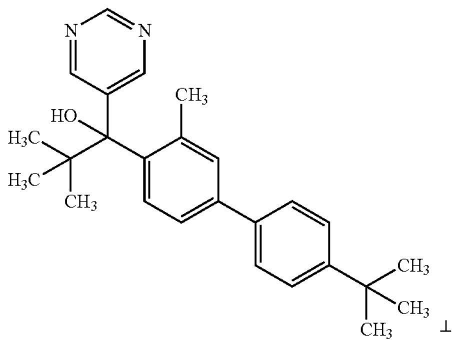 [SMILES: Cc1cc(-c2ccc(C(C)(C)C)cc2)ccc1C(O)(c1cncnc1)C(C)(C)C] | Prepared according to Example 1 using 4-bromo-2-methyl benzaldehyde in A and (4-(tert-butyl)phenyl)boronic acid in D |
| 40 | 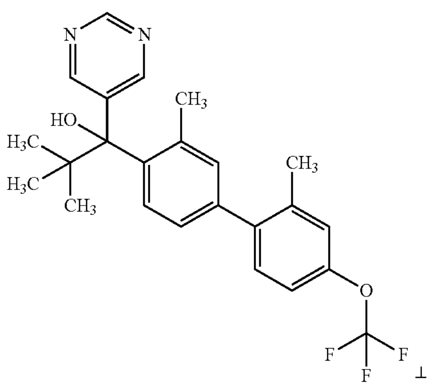 [SMILES: Cc1cc(OC(F)(F)F)ccc1-c1ccc(C(O)(c2cncnc2)C(C)(C)C)c(C)c1] | Prepared according to Example 1 using 4-bromo-2-methyl benzaldehyde in A and (2-methyl-4-(trifluoromethoxy)phenyl)boronic acid in D |
| 41 | 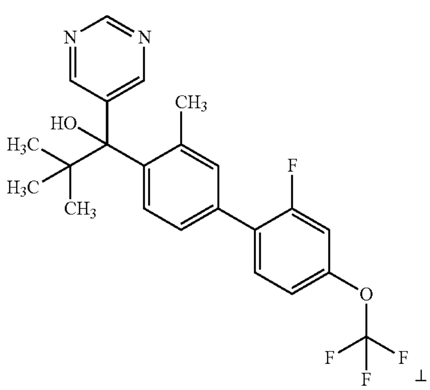 [SMILES: Cc1cc(-c2ccc(OC(F)(F)F)cc2F)ccc1C(O)(c1cncnc1)C(C)(C)C] | Prepared according to Example 1 using 4-bromo-2-methyl benzaldehyde in A and 2-(2-fluoro-4-(trifluoro-methoxy)-phenyl)-4,4,5,5-tetramethyl-1,3,2-dioxaborolane in D |
| 42 | 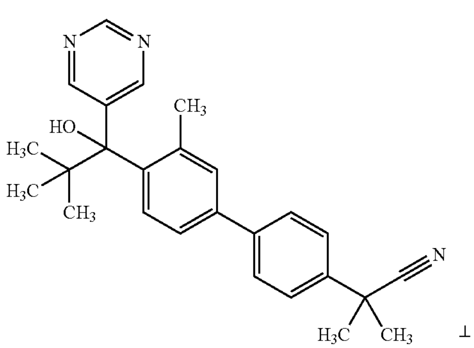 [SMILES: Cc1cc(-c2ccc(C(C)(C)C#N)cc2)ccc1C(O)(c1cncnc1)C(C)(C)C] | Prepared according to Example 1 using 4-bromo-2-methyl benzaldehyde in A and (4-(2-cyanopropan-2-yl)phenyl)-boronic acid in D |

TABLE 1-continued

Structure and Preparation Method.

| Compound Number | Structure | Prepared According to Example |
|---|---|---|
| 43 | 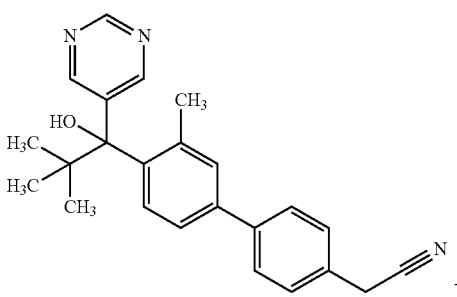 | Prepared according to Example 1 using 4-bromo-2-methyl benzaldehyde in A and (4-(cyanomethyl)phenyl) boronic acid in D |
| 44 | 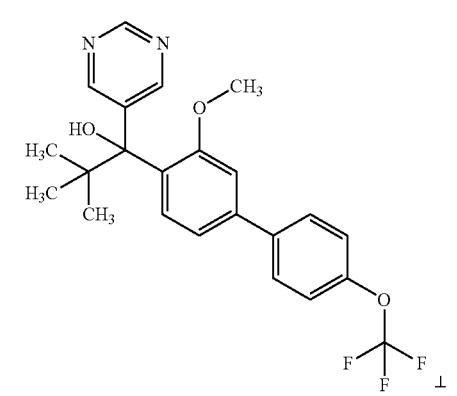 [SMILES: COc1cc(-c2ccc(OC(F)(F)F)cc2)ccc1C(O)(c1cncnc1)C(C)(C)C] | Prepared according to Example 1 using 4-bromo-2-methoxy benzaldehyde in A |
| 45 | 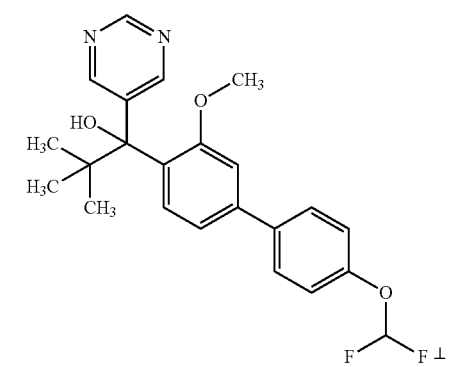 [SMILES: COc1cc(-c2ccc(OC(F)F)cc2)ccc1C(O)(c1cncnc1)C(C)(C)C] | Prepared according to Example 1 using 4-bromo-2-methoxy benzaldehyde in A and 2-(4-(difluoromethoxy)phenyl)-4,4,5,5-tetramethyl-1,3,2-dioxaborolane in D |
| 46 | 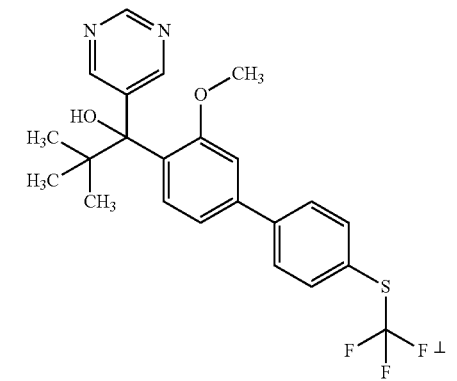 | Prepared according to Example 1 using 4-bromo-2-methoxy benzaldehyde in A and 4,4,5,5-tetramethyl-2-(4-((trifluoromethyl)thio)phenyl)-1,3,2-dioxaborolane in D |

TABLE 1-continued

Structure and Preparation Method.

| Compound Number | Structure | Prepared According to Example |
|---|---|---|
| 47 | 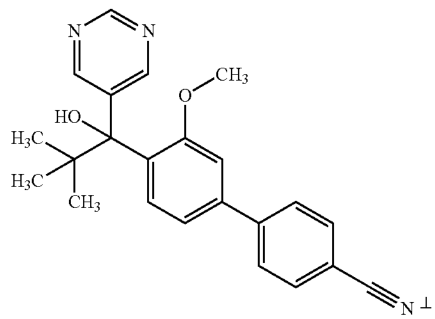 [SMILES: COc1cc(-c2ccc(C#N)cc2)ccc1C(O)(c1cncnc1)C(C)(C)C] | Prepared according to Example 1 using 4-bromo-2-methoxy benzaldehyde in A and (4-cyanophenyl)boronic acid in D |
| 48 | 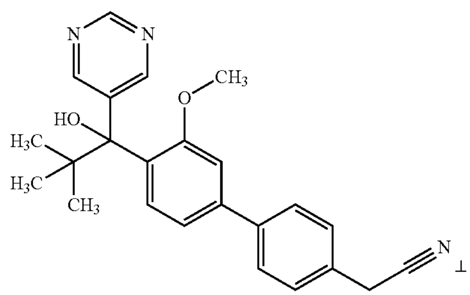 [SMILES: COc1cc(-c2ccc(CC#N)cc2)ccc1C(O)(c1cncnc1)C(C)(C)C] | Prepared according to Example 1 using 4-bromo-2-methoxy benzaldehyde in A and (4-(cyanomethyl)phenyl) boronic acid in D |
| 49 | 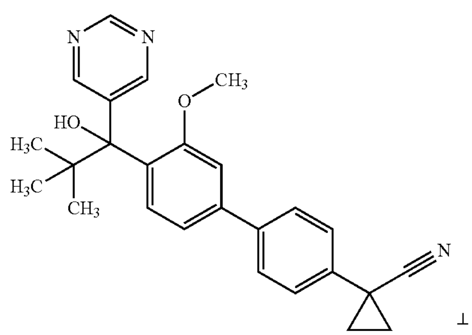 [SMILES: COc1cc(-c2ccc(C3(C#N)CC3)cc2)ccc1C(O)(c1cncnc1)C(C)(C)C] | Prepared according to Example 1 using 4-bromo-2-methoxy benzaldehyde in A and (4-(1-cyanocyclopropyl) phenyl)-boronic acid in D |
| 50 | 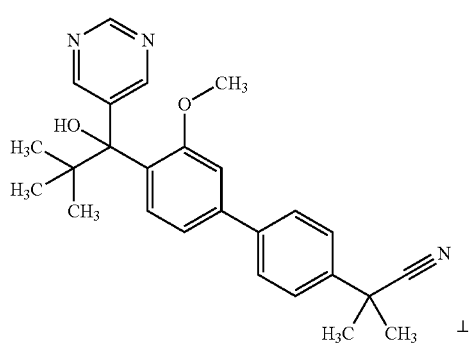 [SMILES: COc1cc(-c2ccc(C(C)(C)C#N)cc2)ccc1C(O)(c1cncnc1)C(C)(C)C] | Prepared according to Example 1 using 4-bromo-2-methoxy benzaldehyde in A and (4-(2-cyanopropan-2-yl)phenyl)-boronic acid in D |

TABLE 1-continued

Structure and Preparation Method.

| Compound Number | Structure | Prepared According to Example |
|---|---|---|
| 51 | 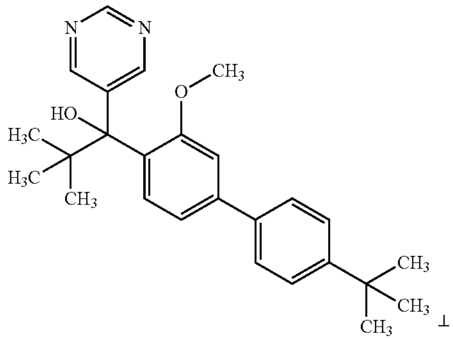 | Prepared according to Example 1 using 4-bromo-2-methoxy benzaldehyde in A and (4-(tert-butyl)phenyl)boronic acid in D |
| 52 | 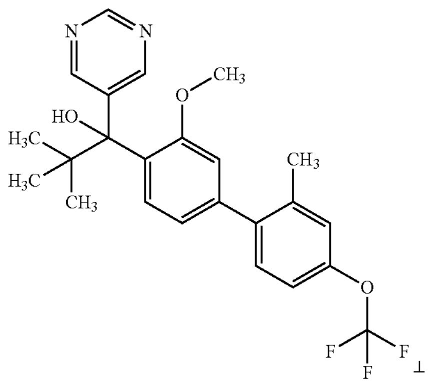 [SMILES: COc1cc(-c2ccc(OC(F)(F)F)cc2C)ccc1C(O)(c1cncnc1)C(C)(C)C] | Prepared according to Example 1 using 4-bromo-2-methoxy benzaldehyde in A and (2-methyl-4-(trifluoromethoxy)-phenyl)boronic acid in D |
| 53 | 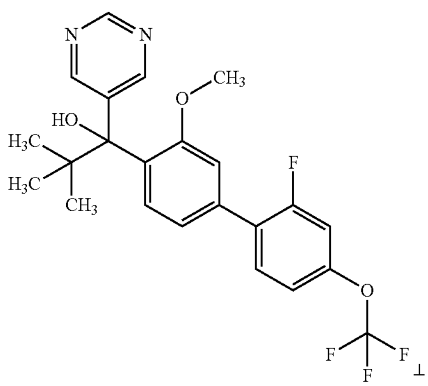 [SMILES: COc1cc(-c2ccc(OC(F)(F)F)cc2F)ccc1C(O)(c1cncnc1)C(C)(C)C] | Prepared according to Example 1 using 4-bromo-2-methoxy benzaldehyde in A and 2-(2-fluoro-4-(trifluoromethoxy)-phenyl)-4,4,5,5-tetramethyl-1,3,2-dioxaborolane in D |
| 54 | 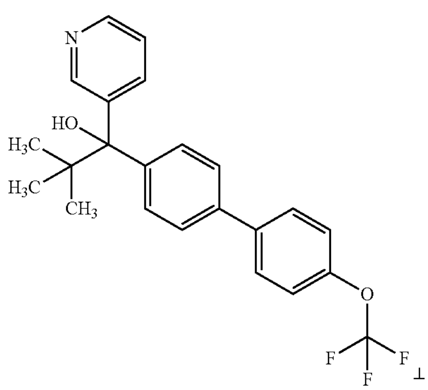 | Prepared according to Example 1 using 3-bromopyridine in A |

TABLE 1-continued

Structure and Preparation Method.

| Compound Number | Structure | Prepared According to Example |
|---|---|---|
| 55 | 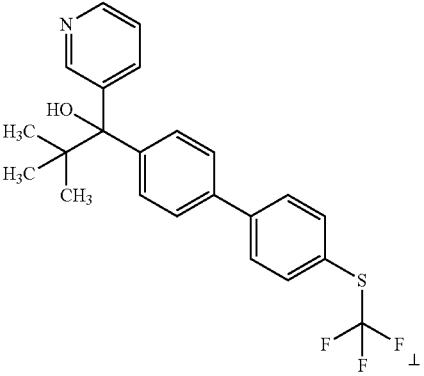 | Prepared according to Example 1 using 3-bromopyridine in A and 4,4,5,5-tetramethyl-2-(4-((trifluoromethyl)thio)phenyl)-1,3,2-dioxaborolane in D |
| 56 | 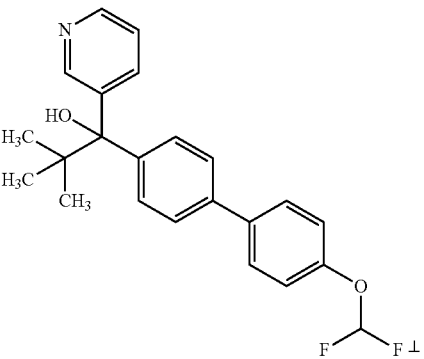 [SMILES: CC(C)(C)C(O)(c1ccc(-c2ccc(OC(F)F)cc2)cc1)c1cccnc1] | Prepared according to Example 1 using 3-bromopyridine in A and 2-(4(difluoromethoxy)-phenyl)-4,4,5,5-tetramethyl-1,3,2-dioxaborolane in D |
| 57 | 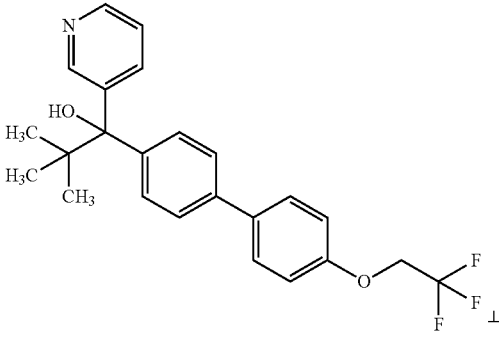 [SMILES: CC(C)(C)C(O)(c1ccc(-c2ccc(OCC(F)(F)F)cc2)cc1)c1cccnc1] | Prepared according to Example 1 3-bromopyridine in A and 4-(2,2,2-trifluoroethoxy)phenyl)-boronic acid in D |
| 58 | 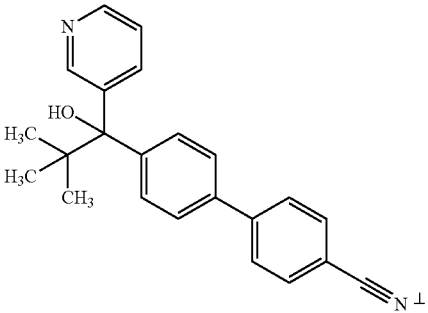 [SMILES: CC(C)(C)C(O)(c1ccc(-c2ccc(C#N)cc2)cc1)c1cccnc1] | Prepared according to Example 1 using 3-bromopyridine in A and (4-cyanophenyl)boronic acid in D |

TABLE 1-continued

Structure and Preparation Method.

| Compound Number | Structure | Prepared According to Example |
|---|---|---|
| 59 | 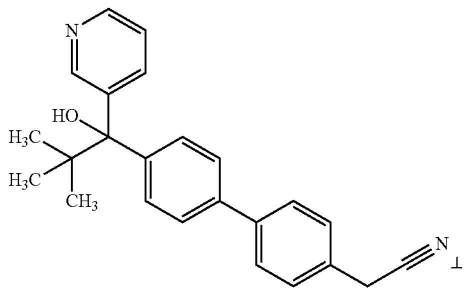 [SMILES: CC(C)(C)C(O)(c1ccc(-c2ccc(CC#N)cc2)cc1)c1cccnc1] | Prepared according to Example 1 using 3-bromopyridine in A and (4-(cyanomethyl)phenyl)-boronic acid in D |
| 60 | 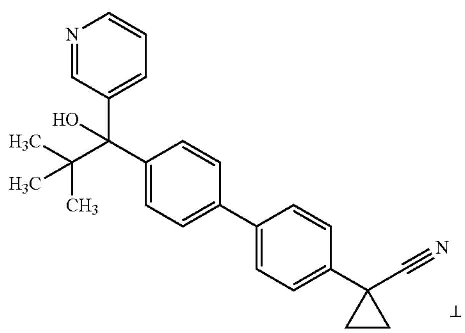 | Prepared according to Example 1 using 3-bromopyridine in A and (4-(1-cyanocyclopropyl)-phenyl)boronic acid in D |
| 61 | 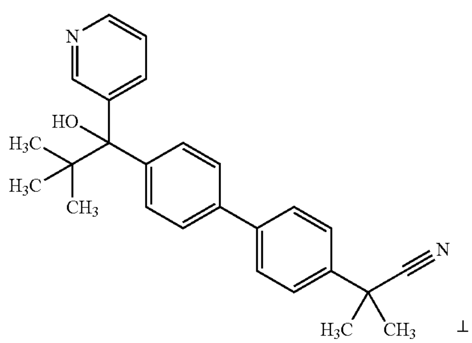 [SMILES: CC(C)(C#N)c1ccc(-c2ccc(C(O)(c3cccnc3)C(C)(C)C)cc2)cc1] | Prepared according to Example 1 using 3-bromopyridine in A and (4-(2-cyanopropan-2-yl)phenyl)boronic acid in D |
| 62 | 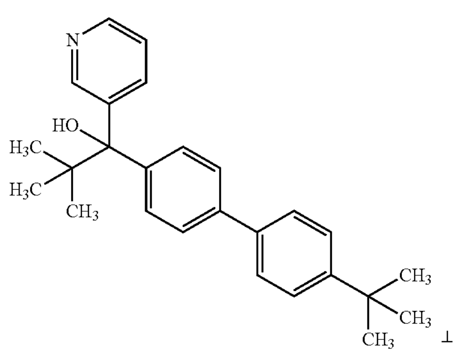 [SMILES: CC(C)(C)c1ccc(-c2ccc(C(O)(c3cccnc3)C(C)(C)C)cc2)cc1] | Prepared according to Example 1 using 3-bromopyridine in A and (4-(tert-butyl)phenyl)-boronic acid in D |

TABLE 1-continued

Structure and Preparation Method.

| Compound Number | Structure | Prepared According to Example |
|---|---|---|
| 63 | 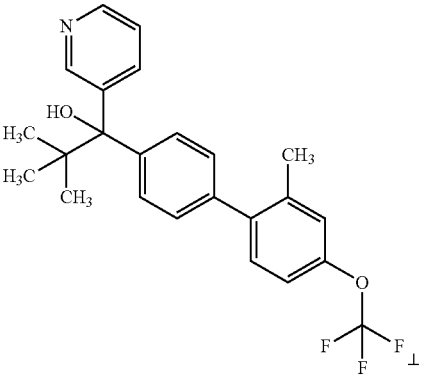 [SMILES: Cc1cc(OC(F)(F)F)ccc1-c1ccc(C(O)(c2cccnc2)C(C)(C)C)cc1] | Prepared according to Example 1 using 3-bromopyridine in A and (2-methyl-4-(trifluoromethoxy)phenyl)boronic acid in D |
| 64 | 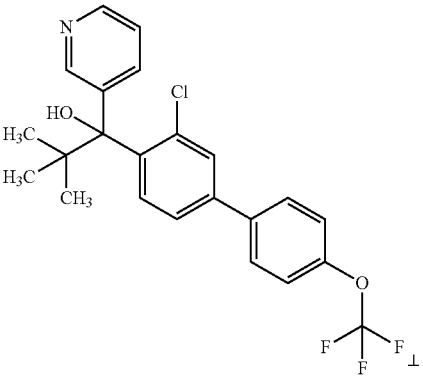 [SMILES: CC(C)(C)C(O)(c1cccnc1)c1ccc(-c2ccc(OC(F)(F)F)cc2)cc1Cl] | Prepared according to Example 1 using 3-bromopyridine and 4-bromo-2-chlorobenzaldehyde in A |
| 65 | 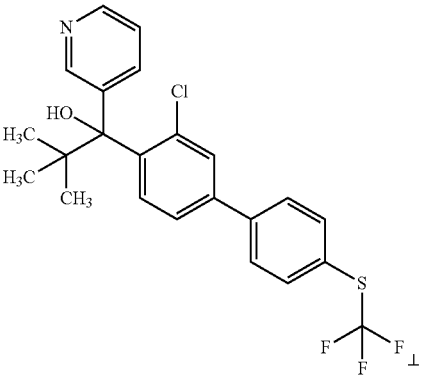 [SMILES: CC(C)(C)C(O)(c1cccnc1)c1ccc(-c2ccc(SC(F)(F)F)cc2)cc1Cl] | Prepared according to Example 1 using 3-bromopyridine and 4-bromo-2-chlorobenzaldehyde in A and 4,4,5,5-tetramethyl-2-(4-((trifluoromethyl)thio)phenyl)-1,3,2-dioxaborolane in D |
| 66 | 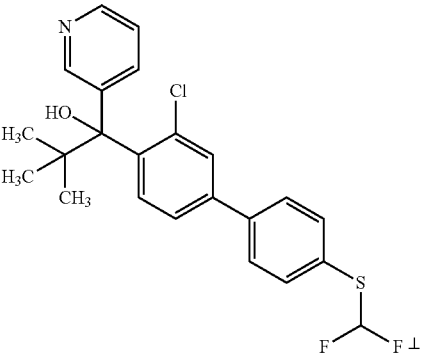 | Prepared according to Example 1 using 3-bromopyridine and 4-bromo-2-chlorobenzaldehyde in A and 2-(4-(difluoromethoxy)phenyl)-4,4,5,5-tetramethyl-1,3,2-dioxaborolane in D |

TABLE 1-continued

Structure and Preparation Method.

| Compound Number | Structure | Prepared According to Example |
|---|---|---|
| 67 | 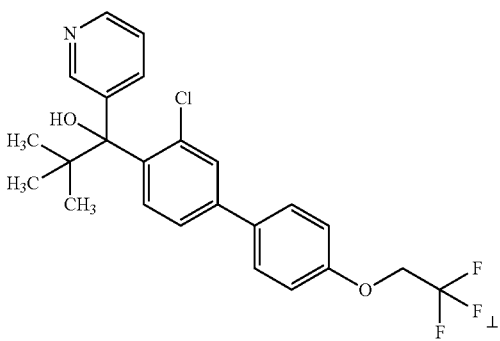 | Prepared according to Example 1 using 3-bromopyridine and 4-bromo-2-chlorobenzaldehyde in A and 4-(2,2,2-trifluoroethoxy)-phenyl)boronic acid in D |
| 68 | 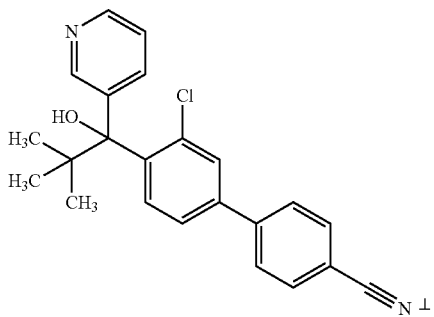 [SMILES: CC(C)(C)C(O)(c1cccnc1)c1ccc(-c2ccc(C#N)cc2)cc1Cl] | Prepared according to Example 1 using 3-bromopyridine and 4-bromo-2-chlorobenzaldehyde in A and (4-cyanophenyl)boronic acid in D |
| 69 | 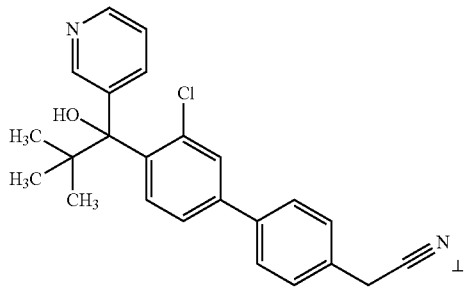 | Prepared according to Example 1 using 3-bromopyridine and 4-bromo-2-chlorobenzaldehyde in A and (4-(cyanomethyl)-phenyl)boronic acid in D |
| 70 | 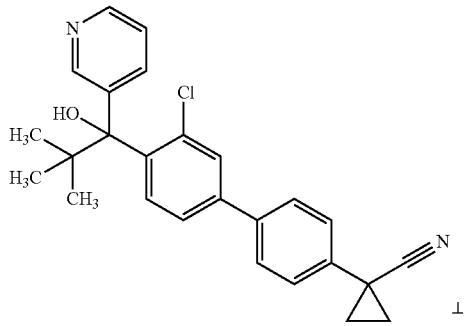 [SMILES: CC(C)(C)C(O)(c1cccnc1)c1ccc(-c2ccc(C3(C#N)CC3)cc2)cc1Cl] | Prepared according to Example 1 using 3-bromopyridine and 4-bromo-2-chlorobenzaldehyde in A and 4-(1-cyanocyclopropyl)-phenyl)boronic acid in D |

TABLE 1-continued

Structure and Preparation Method.

| Compound Number | Structure | Prepared According to Example |
|---|---|---|
| 71 | 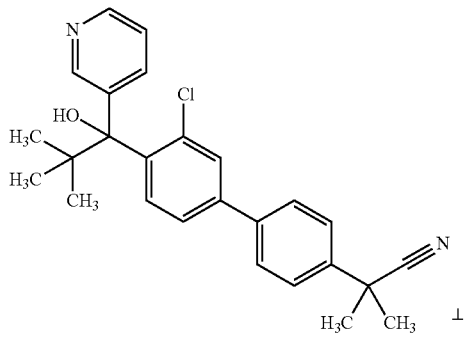 | Prepared according to Example 1 using 3-bromopyridine and 4-bromo-2-chlorobenzaldehyde in A and (4-(2-cyanopropan-2-yl)phenyl)boronic acid in D |
| 72 | 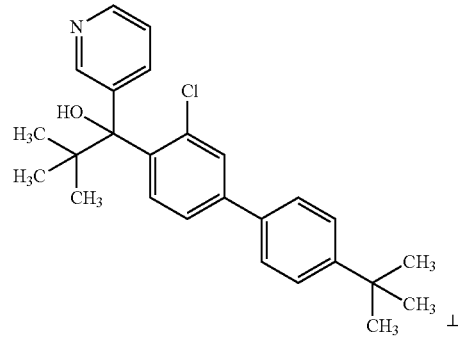 | Prepared according to Example 1 using 3-bromopyridine and 4-bromo-2-chlorobenzaldehyde in A and (4-(tert-butyl)phenyl)-boronic acid in D |
| 73 | 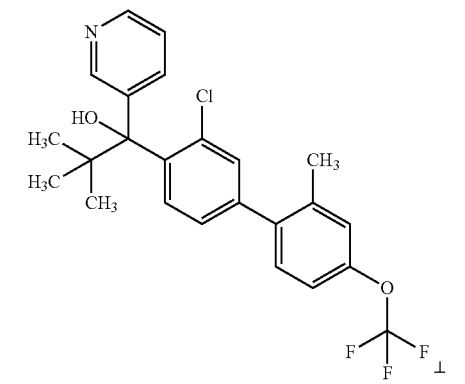 [SMILES: Cc1cc(OC(F)(F)F)ccc1-c1ccc(C(O)(c2cccnc2)C(C)(C)C)c(Cl)c1] | Prepared according to Example 1 using 3-bromopyridine and 4-bromo-2-chlorobenzaldehyde in A and (2-methyl-4-(trifluoromethoxy)phenyl)boronic acid in D |
| 74 | 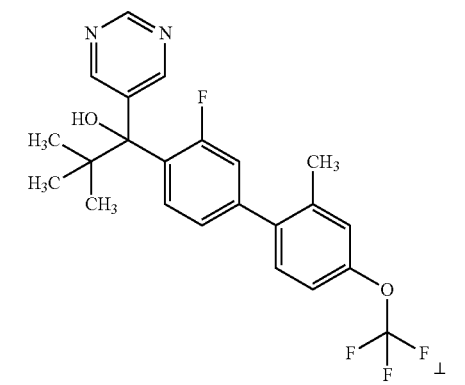 [SMILES: Cc1cc(OC(F)(F)F)ccc1-c1ccc(C(O)(c2cncnc2)C(C)(C)C)c(F)c1] | Prepared according to Example 1 using 4-bromo-2-fluoro benzaldehyde in A and (2-methyl-4-(trifluoromethoxy)-phenyl)boronic acid in D |

TABLE 1-continued

Structure and Preparation Method.

| Compound Number | Structure | Prepared According to Example |
|---|---|---|
| 75 | 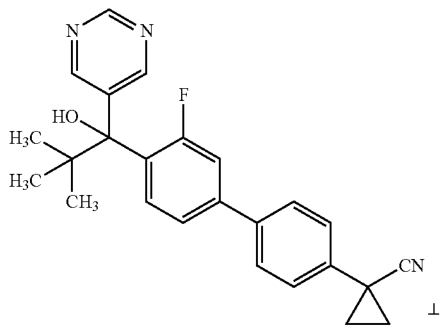 [SMILES: CC(C)(C)C(O)(c1cncnc1)c1ccc(-c2ccc(C3(C#N)CC3)cc2)cc1F] | Prepared according to Example 1 using 4-bromo-2-fluoro benzaldehyde in A and (4-(1-cyanocyclopropyl)-phenyl)boronic acid in D |
| 76 | 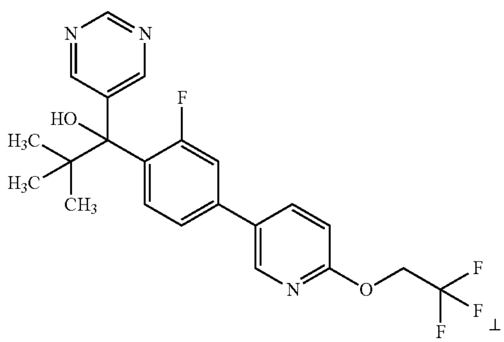 [SMILES: CC(C)(C)C(O)(c1cncnc1)c1ccc(-c2ccc(OCC(F)(F)F)nc2)cc1F] | Prepared according to Example 1 using 4-bromo-2-fluoro benzaldehyde in A and 5-(4,4,5,5-tetramethyl-1,3,2-dioxaborolan-2-yl)-2-(2,2,2-trifluoroethoxy)pyridine in D |
| 77 | 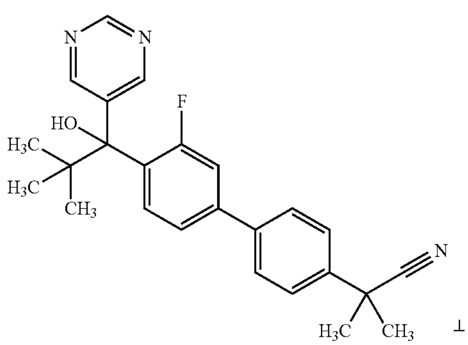 [SMILES: CC(C)(C#N)c1ccc(-c2ccc(C(O)(c3cncnc3)C(C)(C)C)c(F)c2)cc1] | Prepared according to Example 1 using 4-bromo-2-fluoro benzaldehyde in A and (4-(2-cyanopropan-2-yl)phenyl)boronic acid in D |
| 78 | 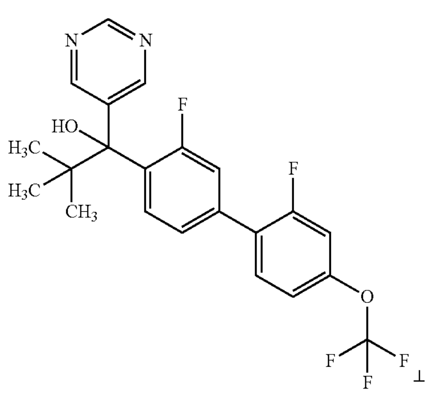 [SMILES: CC(C)(C)C(O)(c1cncnc1)c1ccc(-c2ccc(OC(F)(F)F)cc2F)cc1F] | Prepared according to Example 1 using 4-bromo-2-fluoro benzaldehyde in A and 2-(2-fluoro-4-(trifluoro-methoxy)phenyl)-4,4,5,5-tetramethyl-1,3,2-dioxaborolane in D |

TABLE 1-continued

Structure and Preparation Method.

| Compound Number | Structure | Prepared According to Example |
|---|---|---|
| 79 | 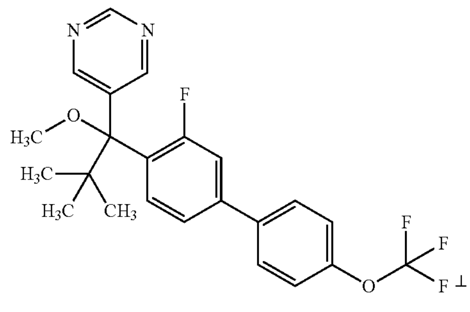 [SMILES: COC(c1cncnc1)(c1ccc(-c2ccc(OC(F)(F)F)cc2)cc1F)C(C)(C)C] | Prepared according to Example 2 |
| 80 | 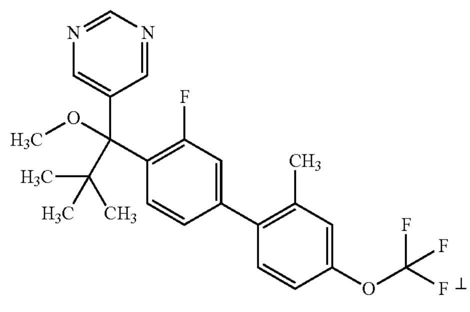 [SMILES: COC(c1cncnc1)(c1ccc(-c2ccc(OC(F)(F)F)cc2C)cc1F)C(C)(C)C] | Prepared according to Example 2 using (2-methyl-4-(trifluoromethoxy)phenyl)-boronic acid in B |
| 81 | 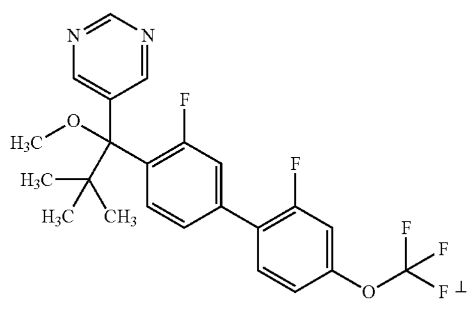 [SMILES: COC(c1cncnc1)(c1ccc(-c2ccc(OC(F)(F)F)cc2F)cc1F)C(C)(C)C] | Prepared according to Example 2 using 2-(2-fluoro-4-(trifluoromethoxy)phenyl)-4,4,5,5-tetramethyl-1,3,2-dioxaborolane in B |
| 82 | 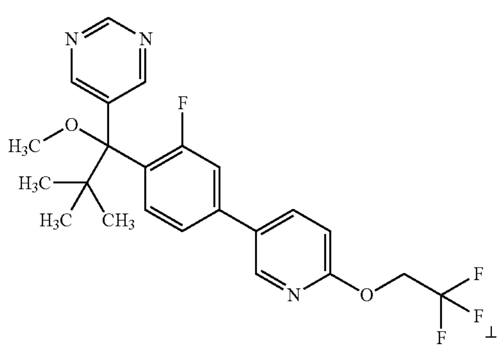 [SMILES: COC(c1cncnc1)(c1ccc(-c2ccc(OCC(F)(F)F)nc2)cc1F)C(C)(C)C] | Prepared according to Example 2 using 5-(4,4,5,5-tetramethyl-1,3,2-dioxa-borolan-2-yl)-2-(2,2,2-trifluoroethoxy)pyridine in B |

TABLE 1-continued

Structure and Preparation Method.

| Compound Number | Structure | Prepared According to Example |
|---|---|---|
| 83 | 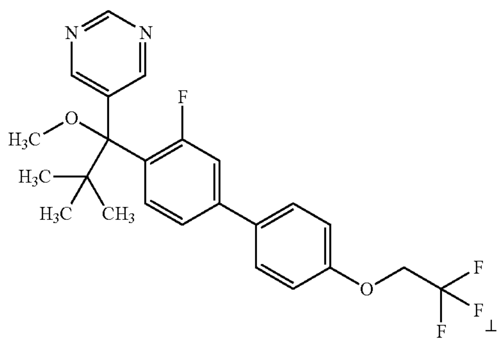 [SMILES: COC(c1cncnc1)(c1ccc(-c2ccc(OCC(F)(F)F)cc2)cc1F)C(C)(C)C] | Prepared according to Example 2 using 4-(2,2,2-trifluoroethoxy)phenyl)boronic acid in B |
| 84 | 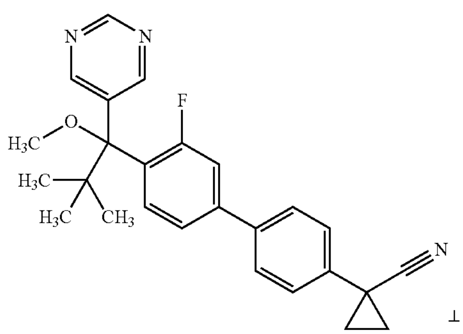 [SMILES: COC(c1cncnc1)(c1ccc(-c2ccc(C3(C#N)CC3)cc2)cc1F)C(C)(C)C] | Prepared according to Example 2 using (4-(1-cyanocyclopropyl)phenyl)boronic acid in B |
| 85 | 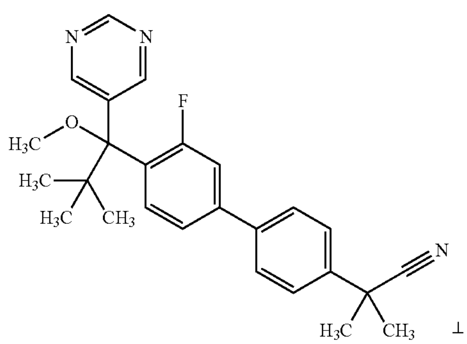 [SMILES: COC(c1cncnc1)(c1ccc(-c2ccc(C(C)(C)C#N)cc2)cc1F)C(C)(C)C] | Prepared according to Example 2 using (4-(2-cyanopropan-2-yl)phenyl)boronic acid in B |
| 86 | 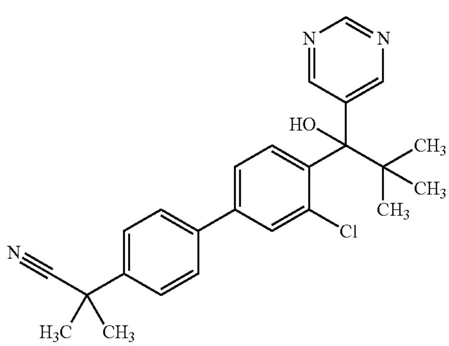 [SMILES: CC(C)(C#N)c1ccc(-c2ccc(C(O)(c3cncnc3)C(C)(C)C)c(Cl)c2)cc1] | Prepared according to Example 1 using 4-bromo-2-chlorobenzaldehyde in A and (4-(2-cyanopropan-2-yl)phenyl)boronic acid in D |

TABLE 1-continued

Structure and Preparation Method.

| Compound Number | Structure | Prepared According to Example |
|---|---|---|
| 87 | 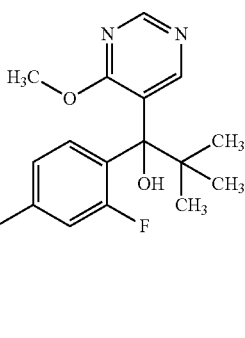 | Prepared according to Example 1 using 4-bromo-2-fluorobenzaldehyde and 5-bromo-4-methoxypyrimidine in A and 5-(4,4,5,5-tetramethyl-1,3,2-dioxaborolan-2-yl)-2-(2,2,2-trifluoroethoxy)pyridine in D |
| 88 | 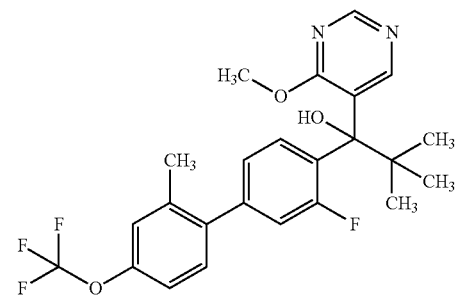 [SMILES: COc1ncncc1C(O)(c1ccc(-c2ccc(OC(F)(F)F)cc2C)cc1F)C(C)(C)C] | Prepared according to Example 1 using 4-bromo-2-fluorobenzaldehyde and 5-bromo-4-methoxypyrimidine in A and (2-methyl-4-(trifluoromethoxy)phenyl) boronic acid in D |
| 89 | 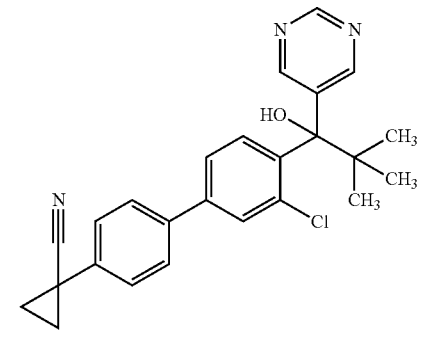 [SMILES: CC(C)(C)C(O)(c1cncnc1)c1ccc(-c2ccc(C3(C#N)CC3)cc2)cc1Cl] | Prepared according to Example 1 using 4-bromo-2-chlorobenzaldehyde in A and (4-(1-cyanocyclopropyl)phenyl) boronic acid in D |
| 91 | 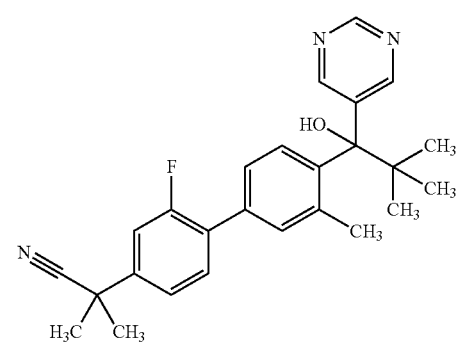 [SMILES: Cc1cc(-c2ccc(C(C)(C)C#N)cc2F)ccc1C(O)(c1cncnc1)C(C)(C)C] | Prepared according to Example 1 using 4-bromo-2-methylbenzaldehyde in A and 2-(3-fluoro-4-(4,4,5,5-tetramethyl-1,3,2-dioxaborolan-2-yl)phenyl)-2-methylpropanenitrile in D |

TABLE 1-continued

Structure and Preparation Method.

| Compound Number | Structure | Prepared According to Example |
|---|---|---|
| 92 | 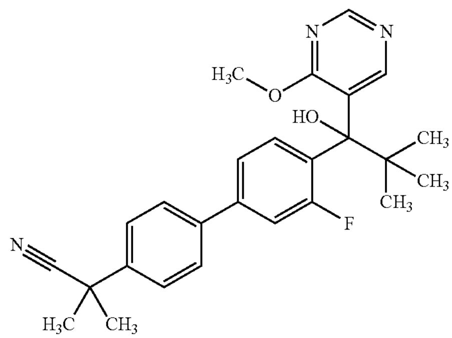 [SMILES: COc1ncncc1C(O)(c1ccc(-c2ccc(C(C)(C)C#N)cc2)cc1F)C(C)(C)C] | Prepared according to Example 1 using 4-bromo-2-fluorobenzaldehyde and 5-bromo-4-methoxypyrimidine in A and (4-(2-cyanopropan-2-yl)phenyl)boronic acid in D |
| 94 | 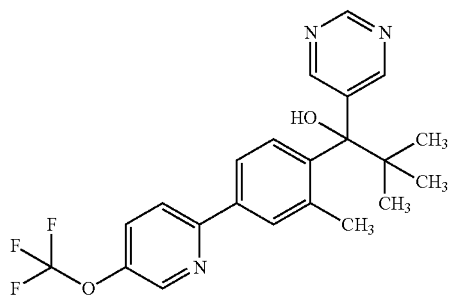 [SMILES: Cc1cc(-c2ccc(OC(F)(F)F)cn2)ccc1C(O)(c1cncnc1)C(C)(C)C] | Prepared according to Example 3 |
| 95 | 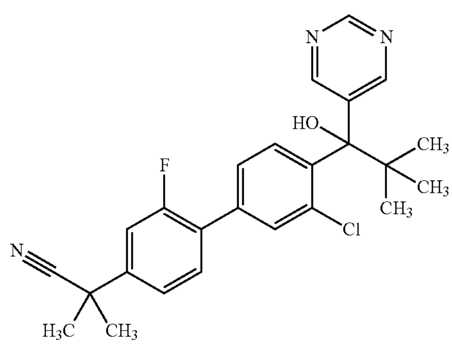 | Prepared according to Example 1 using 4-bromo-2-chlorobenzaldehyde in A and 2-(3-fluoro-4-(4,4,5,5-tetramethyl-1,3,2-dioxaborolan-2-yl)phenyl)-2-methylpropanenitrile in D |
| 96 | 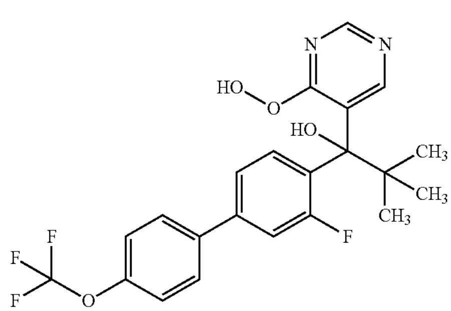 [SMILES: CC(C)(C)C(O)(c1ccc(-c2ccc(OC(F)(F)F)cc2)cc1F)c1cncnc1OO] | Prepared according to Example 1 using 4-bromo-2-fluorobenzaldehyde and 5-bromo-4-methoxypyrimidine in A and (4-(trifluoromethoxy)phenyl)boronic acid in D |

TABLE 1-continued

Structure and Preparation Method.

| Compound Number | Structure | Prepared According to Example |
|---|---|---|
| 97 | 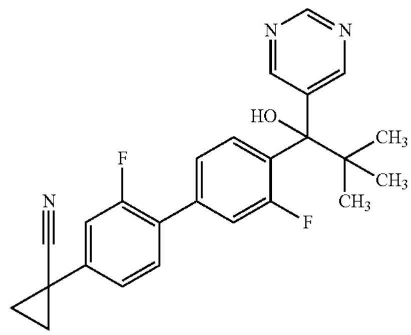 [SMILES: CC(C)(C)C(O)(c1cncnc1)c1ccc(-c2ccc(C3(C#N)CC3)cc2F)cc1F] | Prepared according to Example 1 using 4-bromo-2-fluorobenzaldehyde a in A and 1-(3-fluoro-4-(4,4,5,5-tetramethyl-1,3,2-dioxaborolan-2-yl)phenyl)cyclopropane-carbonitrile in D |
| 98 | 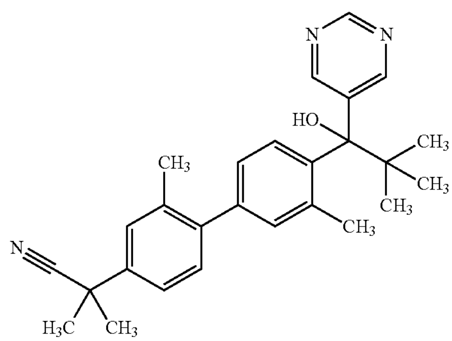 [SMILES: Cc1cc(C(C)(C)C#N)ccc1-c1ccc(C(O)(c2cncnc2)C(C)(C)C)c(C)c1] | Prepared according to Example 3 using 2-(4-bromo-3-methylphenyl)-2-methylpropanenitrile in B |
| 99 | 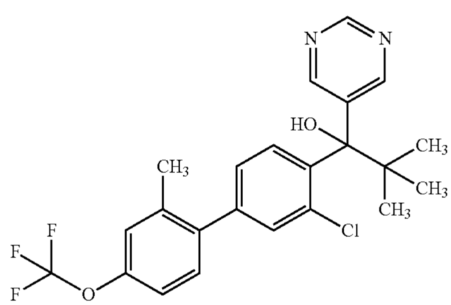 [SMILES: Cc1cc(OC(F)(F)F)ccc1-c1ccc(C(O)(c2cncnc2)C(C)(C)C)c(Cl)c1] | Prepared according to Example 1 using 4-bromo-2-chlorobenzaldehyde in A and (2-methyl-4-(trifluoromethoxy)phenyl)boronic acid in D |
| 100 | 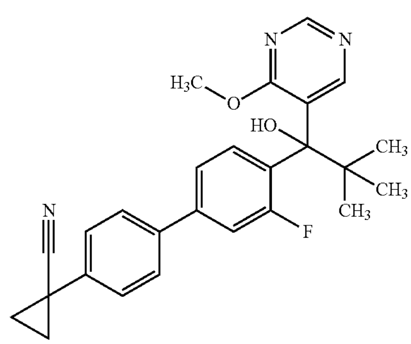 [SMILES: COc1ncncc1C(O)(c1ccc(-c2ccc(C3(C#N)CC3)cc2)cc1F)C(C)(C)C] | Prepared according to Example 1 using 4-bromo-2-fluorobenzaldehyde and 5-bromo-4-methoxypyrimidine in A and (4-(1-cyanocyclopropyl)phenyl)boronic acid in D |

TABLE 1-continued

Structure and Preparation Method.

| Compound Number | Structure | Prepared According to Example |
|---|---|---|
| 101 | 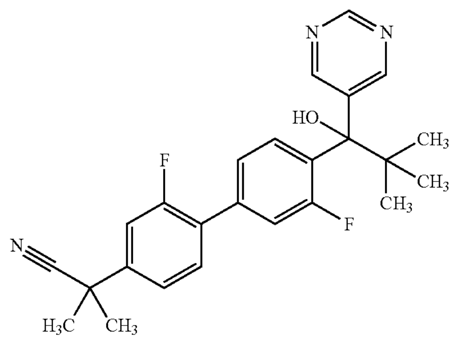 [SMILES: CC(C)(C#N)c1ccc(-c2ccc(C(O)(c3cncnc3)C(C)(C)C)c(F)c2)c(F)c1] | Prepared according to Example 1 using 4-bromo-2-fluorobenzaldehyde a in A and 2-(3-fluoro-4-(4,4,5,5-tetramethyl-1,3,2-dioxaborolan-2-yl)phenyl)-2-methylpropanenitrile in D |
| 102 | 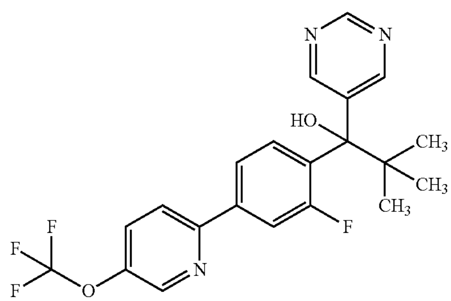 [SMILES: CC(C)(C)C(O)(c1cncnc1)c1ccc(-c2ccc(OC(F)(F)F)cn2)cc1F] | Prepared according to Example 3 using the appropiate bromide prepared in Example 1 |
| 103 | 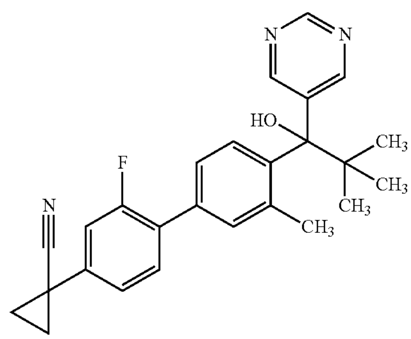 [SMILES: Cc1cc(-c2ccc(C3(C#N)CC3)cc2F)ccc1C(O)(c1cncnc1)C(C)(C)C] | Prepared according to Example 1 using 4-bromo-2-methylbenzaldehyde in A and 1-(3-fluoro-4-(4,4,5,5-tetramethyl-1,3,2-dioxaborolan-2-yl)phenyl)cyclopropane-carbonitrile in D |
| 104 | 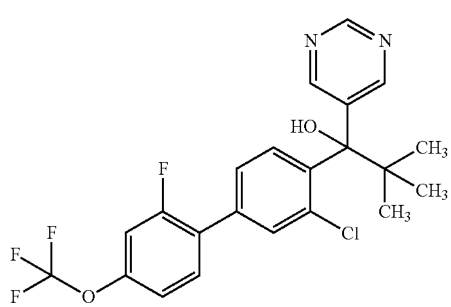 [SMILES: CC(C)(C)C(O)(c1cncnc1)c1ccc(-c2ccc(OC(F)(F)F)cc2F)cc1Cl] | Prepared according to Example 1 using 4-bromo-2-chlorobenzaldehyde in A and 2-(2-fluoro-4-(trifluoromethoxy)phenyl)-4,4,5,5-tetramethyl-1,3,2-dioxaborolane acid in D |

TABLE 1-continued

Structure and Preparation Method.

| Compound Number | Structure | Prepared According to Example |
|---|---|---|
| 105 | 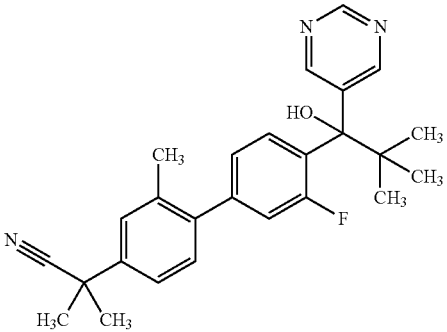 | Prepared according to Example 3 using the appropiate bromide prepared in Example 1 and 2-(4-bromo-3-methylphenyl)-2-methylpropanenitrile in B |
| 106 | 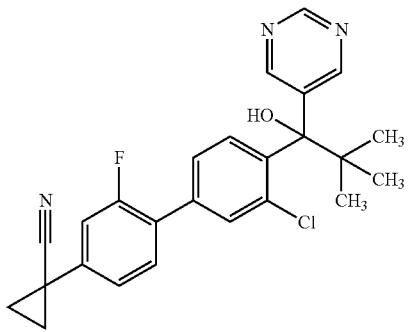 [SMILES: CC(C)(C)C(O)(c1cncnc1)c1ccc(-c2ccc(C3(C#N)CC3)cc2F)cc1Cl] | Prepared according to Example 1 using 4-bromo-2-chlorobenzaldehyde in A and 1-(3-fluoro-4-(4,4,5,5-tetramethyl-1,3,2-dioxaborolan-2-yl)phenyl)cyclopropane-carbonitrile in D |
| 108 | 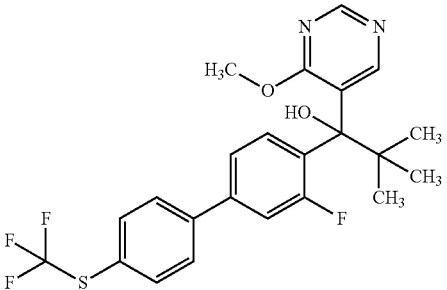 [SMILES: COc1ncncc1C(O)(c1ccc(-c2ccc(SC(F)(F)F)cc2)cc1F)C(C)(C)C] | Prepared according to Example 1 using 4-bromo-2-fluorobenzaldehyde and 5-bromo-4-methoxypyrimidine in A and (4-((trifluoromethyl)thio)phenyl)boronic acid in D |
| 109 | 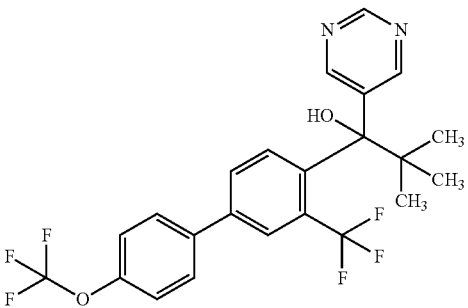 [SMILES: CC(C)(C)C(O)(c1cncnc1)c1ccc(-c2ccc(OC(F)(F)F)cc2)cc1C(F)(F)F] | Prepared according to Example 4 |

TABLE 1-continued

Structure and Preparation Method.

| Compound Number | Structure | Prepared According to Example |
|---|---|---|
| 110 | 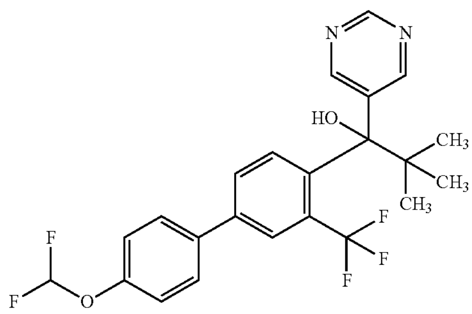 [SMILES: CC(C)(C)C(O)(c1cncnc1)c1ccc(-c2ccc(OC(F)F)cc2)cc1C(F)(F)F] | Prepared according to Example 4 using 2-(4-(difluoromethoxy)phenyl)-4,4,5,5-tetramethyl-1,3,2-dioxaborolane in C |
| 111 | 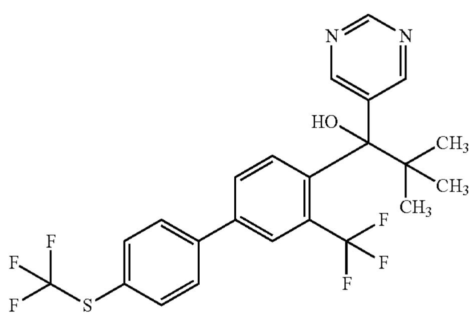 [SMILES: CC(C)(C)C(O)(c1cncnc1)c1ccc(-c2ccc(SC(F)(F)F)cc2)cc1C(F)(F)F] | Prepared according to Example 4 using (4-((trifluoromethyl)thio)phenyl)boronic acid in C |
| 112 | 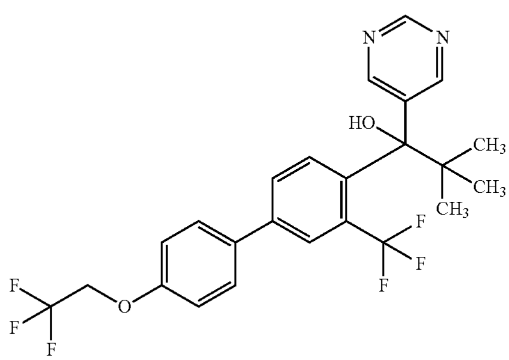 [SMILES: CC(C)(C)C(O)(c1cncnc1)c1ccc(-c2ccc(OCC(F)(F)F)cc2)cc1C(F)(F)F] | Prepared according to Example 4 using (4-(2,2,2-trifluoroethoxy)phenyl)boronic acid in C |
| 113 | 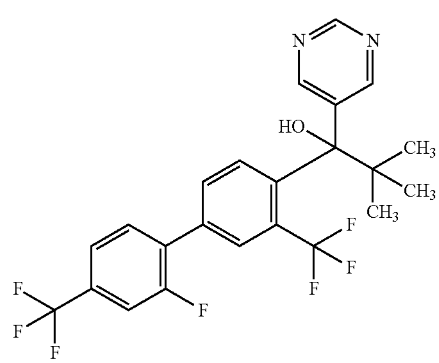 [SMILES: CC(C)(C)C(O)(c1cncnc1)c1ccc(-c2ccc(C(F)(F)F)cc2F)cc1C(F)(F)F] | Prepared according to Example 4 using (2-fluoro-4-(trifluoromethyl)phenyl)boronic acid in C |

TABLE 1-continued

Structure and Preparation Method.

| Compound Number | Structure | Prepared According to Example |
|---|---|---|
| 114 | 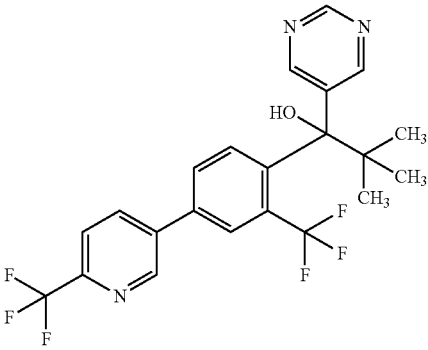 [SMILES: CC(C)(C)C(O)(c1cncnc1)c1ccc(-c2ccc(C(F)(F)F)nc2)cc1C(F)(F)F] | Prepared according to Example 4 using (6-(trifluoromethyl)pyridin-3-yl)boronic acid in C |
| 115 | 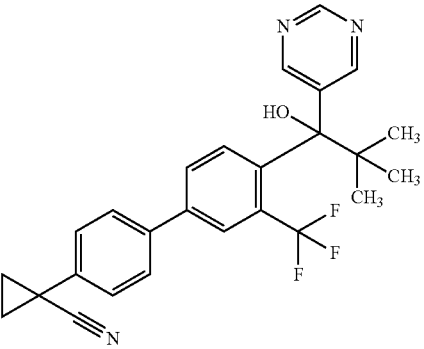 [SMILES: CC(C)(C)C(O)(c1cncnc1)c1ccc(-c2ccc(C3(C#N)CC3)cc2)cc1C(F)(F)F] | Prepared according to Example 4 using (4-(1-cyanocyclopropyl)phenyl)boronic acid in C |
| 116 | 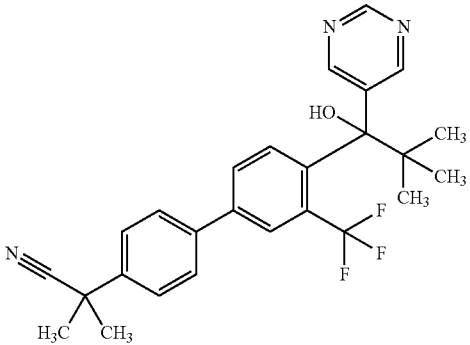 [SMILES: CC(C)(C#N)c1ccc(-c2ccc(C(O)(c3cncnc3)C(C)(C)C)c(C(F)(F)F)c2)cc1] | Prepared according to Example 4 using (4-(2-cyanopropan-2-yl)phenyl)boronic acid in C |
| 117 | 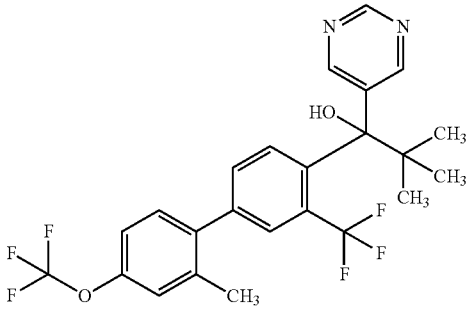 [SMILES: Cc1cc(OC(F)(F)F)ccc1-c1ccc(C(O)(c2cncnc2)C(C)(C)C)c(C(F)(F)F)c1] | Prepared according to Example 4 using (2-methyl-4-(trifluoromethoxy)phenyl)boronic acid in C |

TABLE 1-continued

Structure and Preparation Method.

| Compound Number | Structure | Prepared According to Example |
|---|---|---|
| 118 | 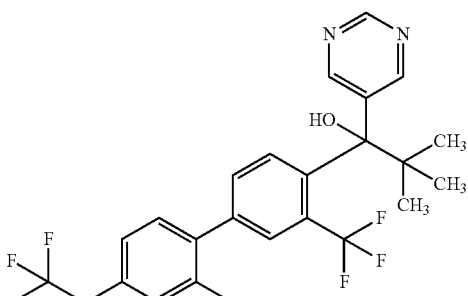 | Prepared according to Example 4 using 2-(2-fluoro-4-(trifluoromethoxy)phenyl)-4,4,5,5-tetramethyl-1,3,2-dioxaborolane in C |
| 119 | 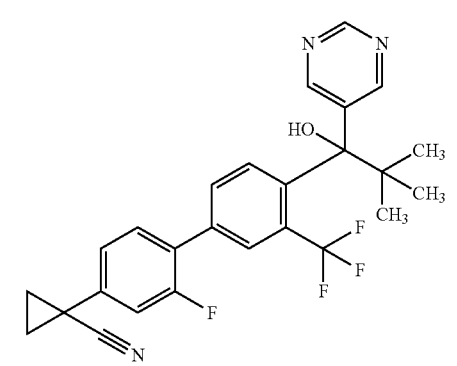 [SMILES: CC(C)(C)C(O)(c1cncnc1)c1ccc(-c2ccc(C3(C#N)CC3)cc2F)cc1C(F)(F)F] | Prepared according to Example 4 using 1-(3-fluoro-4-(4,4,5,5-tetramethyl-1,3,2-dioxaborolan-2-yl)phenyl)cyclopropane-carbonitrile in C |
| 120 | 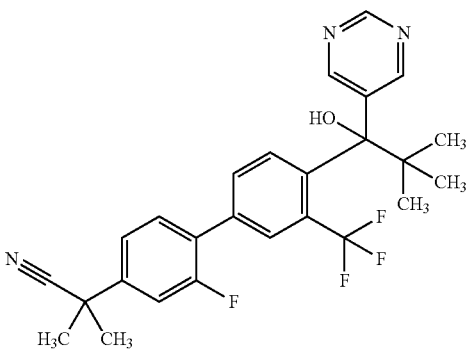 [SMILES: CC(C)(C#N)c1ccc(-c2ccc(C(O)(c3cncnc3)C(C)(C)C)c(C(F)(F)F)c2)c(F)c1] | Prepared according to Example 4 using 2-(3-fluoro-4-(4,4,5,5-tetramethyl-1,3,2-dioxaborolan-2-yl)phenyl)-2-methylpropanenitrile in C |
| 120 | 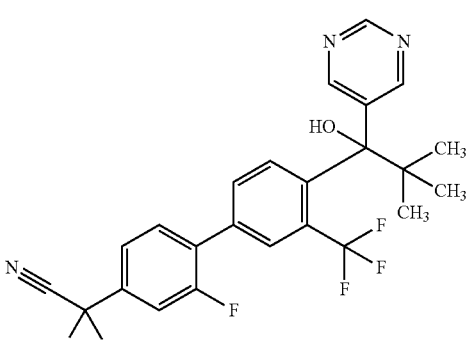 | Prepared according to Example 4 using 2-(3-fluoro-4-(4,4,5,5-tetramethyl-1,3,2-dioxaborolan-2-yl)phenyl)-2-methylpropanenitrile in C |

TABLE 2

| Compound Number | Mass Spec | NMR $^1$H, $^{13}$C, $^{19}$F |
|---|---|---|
| 1 | ESIMS m/z 403 ([M + H]$^+$) | $^1$H NMR (400 MHz, CDCl$_3$) δ 9.10 (s, 1H), 8.95 (s, 2H), 7.64-7.54 (m, 4H), 7.54-7.43 (m, 2H), 7.32-7.26 (m, 2H), 2.65 (s, 1H), 1.19 (s, 9H) $^{19}$F NMR (376 MHz, CDCl$_3$) δ −57.81 |
| 2 | ESIMS m/z 385 ([M + H]$^+$) | $^1$H NMR (400 MHz, CDCl$_3$) δ 9.07 (s, 1H), 8.93 (s, 2H), 7.64-7.48 (m, 6H), 7.19 (d, J = 8.7 Hz, 2H), 6.55 (t, J = 73.8 Hz, 1H), 2.56 (s, 1H), 1.20 (s, 9H) $^{19}$F NMR (376 MHz, CDCl$_3$) δ −80.78 |
| 3 | ESIMS m/z 344 ([M + H]$^+$) | $^1$H NMR (400 MHz, CDCl$_3$) δ 9.07 (s, 1H), 8.94 (s, 2H), 7.75-7.71 (m, 2H), 7.69-7.62 (m, 4H), 7.59-7.53 (m, 2H), 2.61 (s, 1H), 1.20 (s, 9H) $^{13}$C NMR (126 MHz, CDCl$_3$) δ 156.8, 156.4, 144.6, 144.4, 138.7, 138.1, 132.7, 128.9, 127.6, 126.6, 118.8, 111.2, 80.9, 39.5, 26.9 |
| 4 | ESIMS m/z 353 ([M + H]$^+$) | $^1$H NMR (400 MHz, CDCl$_3$) δ 9.08 (s, 1H), 8.94 (s, 2H), 7.62-7.58 (m, 2H), 7.53-7.47 (m, 4H), 7.43-7.39 (m, 2H), 2.58 (s, 1H), 1.19 (s, 9H) $^{13}$C NMR (101 MHz, CDCl$_3$) δ 156.6, 156.4, 143.2, 139.0, 138.8, 138.6, 133.7, 129.0, 128.7, 128.2, 126.4, 80.9, 39.4, 27.0 |
| 5 | ESIMS m/z 319 ([M + H]$^+$) | $^1$H NMR (400 MHz, CDCl$_3$) δ 9.08 (s, 1H), 8.94 (s, 2H), 7.62-7.53 (m, 6H), 7.47-7.41 (m, 2H), 7.39-7.33 (m, 1H), 2.64 (s, 1H), 1.20 (s, 9H) $^{13}$C NMR (126 MHz, CDCl$_3$) δ 156.5, 156.4, 142.8, 140.2, 140.1, 138.9, 128.8, 128.6, 127.5, 127.0, 126.5, 80.9, 39.4, 26.9 |
| 6 | ESIMS m/z 387 ([M + H]$^+$) | $^1$H NMR (400 MHz, CDCl$_3$) δ 9.09 (s, 1H), 8.95 (s, 2H), 7.71-7.61 (m, 6H), 7.59-7.51 (m, 2H), 2.57 (s, 1H), 1.21 (s, 9H) $^{19}$F NMR (376 MHz, CDCl$_3$) δ −62.46 |
| 7 | ESIMS m/z 388 ([M + H]$^+$) | $^1$H NMR (400 MHz, CDCl$_3$) δ 9.08 (s, 1H), 8.95 (s, 2H), 8.93 (d, J = 2.2 Hz, 1H), 8.03 (ddd, J = 8.1, 2.3, 0.8 Hz, 1H), 7.76 (dd, J = 8.2, 0.8 Hz, 1H), 7.71-7.65 (m, 2H), 7.60-7.55 (m, 2H), 2.59 (s, 1H), 1.21 (s, 9H) $^{19}$F NMR (376 MHz, CDCl$_3$) δ −67.74 |
| 8 | ESIMS m/z 437 ([M + H]$^+$) | $^1$H NMR (400 MHz, CDCl$_3$) δ 9.09 (s, 1H), 8.65 (s, 2H), 8.15 (dt, J = 8.3, 0.8 Hz, 1H), 7.61-7.54 (m, 2H), 7.53-7.48 (m, 2H), 7.31 (dp, J = 7.7, 1.0 Hz, 2H), 3.76 (s, 1H), 1.29 (s, 9H) $^{19}$F NMR (376 MHz, CDCl$_3$) δ −57.80 |
| 9 | ESIMS m/z 378 ([M + H]$^+$) | $^1$H NMR (400 MHz, CDCl$_3$) δ 9.09 (s, 1H), 8.66 (s, 2H), 8.22-8.17 (m, 1H), 7.79-7.74 (m, 2H), 7.70-7.65 (m, 2H), 7.59-7.53 (m, 2H), 3.72 (s, 1H), 1.29 (s, 9H) $^{13}$C NMR (126 MHz, CDCl$_3$) δ 156.9, 156.1, 142.78, 140.8, 140.3, 137.9, 134.6, 132.8, 131.3, 130.9, 127.6, 124.5, 118.5, 112.1, 81.0, 39.6, 27.2 |
| 10 | ESIMS m/z 419 ([M + H]$^+$) | $^1$H NMR (400 MHz, CDCl$_3$) δ 9.09 (s, 1H), 8.65 (s, 2H), 8.16-8.12 (m, 1H), 7.59-7.53 (m, 2H), 7.52-7.49 (m, 2H), 7.22 (d, J = 8.7 Hz, 2H), 6.56 (t, J = 73.6 Hz, 1H), 3.77 (s, 1H), 1.29 (s, 9H) $^{19}$F NMR (376 MHz, CDCl$_3$) δ −80.9 |
| 11 | ESIMS m/z 403 ([M + H]$^+$) | $^1$H NMR (400 MHz, CDCl$_3$) δ 9.09 (s, 1H), 8.94 (s, 2H), 7.65-7.60 (m, 2H), 7.55-7.40 (m, 5H), 7.21 (ddt, J = 7.8, 2.4, 1.2 Hz, 1H), 2.50 (s, 1H), 1.20 (s, 9H) $^{19}$F NMR (376 MHz, CDCl$_3$) δ −57.7 |
| 12 | ESIMS m/z 403 ([M + H]$^+$) | $^1$H NMR (400 MHz, CDCl$_3$) δ 9.08 (s, 1H), 8.94 (s, 2H), 7.63-7.59 (m, 2H), 7.46-7.33 (m, 6H), 2.48 (s, 1H), 1.20 (s, 9H) $^{19}$F NMR (376 MHz, CDCl$_3$) δ −57.1 |
| 13 | ESIMS m/z 349 ([M + H]$^+$) | $^1$H NMR (400 MHz, CDCl$_3$) δ 9.07 (s, 1H), 8.92 (s, 2H), 7.61-7.55 (m, 2H), 7.54-7.48 (m, 4H), 7.00-6.94 (m, 2H), 3.85 (s, 3H), 2.50 (s, 1H), 1.20 (s, 9H) $^{13}$C NMR (126 MHz, CDCl$_3$) δ 159.3, 156.7, 156.4, 142.2, 139.8, 138.9, 132.6, 128.6, 128.0, 126.1, 114.3, 80.9, 55.3, 39.4, 26.9 |
| 14 | ESIMS m/z 417 ([M + H]$^+$) | $^1$H NMR (400 MHz, CDCl$_3$) δ 9.07 (s, 1H), 8.93 (s, 2H), 7.62-7.57 (m, 2H), 7.56-7.49 (m, 4H), 7.04-6.99 (m, 2H), 4.39 (q, J = 8.1 Hz, 2H), 2.50 (s, 1H), 1.20 (s, 9H) $^{19}$F NMR (376 MHz, CDCl$_3$) δ −73.9 |

TABLE 2-continued

Analytical Data.

| Compound Number | Mass Spec | NMR $^1$H, $^{13}$C, $^{19}$F |
|---|---|---|
| 15 | ESIMS m/z 421 ([M + H]$^+$) | $^1$H NMR (400 MHz, CDCl$_3$) δ 9.09 (s, 1H), 8.85 (s, 2H), 7.89 (t, J = 8.5 Hz, 1H), 7.60-7.53 (m, 2H), 7.38 (dd, J = 8.3, 2.0 Hz, 1H), 7.32-7.27 (m, 2H), 7.16 (dd, J = 13.9, 2.0 Hz, 1H), 3.06 (d, J = 9.0 Hz, 1H), 1.26 (s, 9H) $^{19}$F NMR (376 MHz, CDCl$_3$) δ −57.81, −107.0 |
| 16 | ESIMS m/z 403 ([M + H]$^+$) | $^1$H NMR (400 MHz, CDCl$_3$) δ 9.09 (s, 1H), 8.84 (s, 2H), 7.87 (t, J = 8.5 Hz, 1H), 7.59-7.51 (m, 2H), 7.37 (dd, J = 8.3, 1.9 Hz, 1H), 7.23-7.19 (m, 2H), 7.16 (dd, J = 14.0, 2.0 Hz, 1H), 6.56 (t, J = 73.7 Hz, 1H), 3.04 (d, J = 9.3 Hz, 1H), 1.26 (s, 9H) $^{19}$F NMR (376 MHz, CDCl$_3$) δ −80.96, −107.2 |
| 17 | ESIMS m/z 362 ([M + H]$^+$) | $^1$H NMR (400 MHz, CDCl$_3$) δ 9.09 (s, 1H), 8.86 (s, 2H), 7.93 (t, J = 8.4 Hz, 1H), 7.77-7.72 (m, 2H), 7.69-7.62 (m, 2H), 7.42 (dd, J = 8.3, 2.0 Hz, 1H), 7.20 (dd, J = 13.6, 2.0 Hz, 1H), 3.01 (d, J = 8.3 Hz, 1H), 1.26 (s, 9H) $^{19}$F NMR (376 MHz, CDCl$_3$) δ −106.3 |
| 18 | ESIMS m/z 371 ([M + H]$^+$) | $^1$H NMR (400 MHz, CDCl$_3$) δ 9.09 (s, 1H), 8.84 (s, 2H), 7.87 (t, J = 8.5 Hz, 1H), 7.51-7.46 (m, 2H), 7.45-7.39 (m, 2H), 7.37 (dd, J = 8.3, 2.0 Hz, 1H), 7.16 (dd, J = 14.0, 2.0 Hz, 1H), 3.03 (d, J = 9.3 Hz, 1H), 1.26 (s, 9H) $^{19}$F NMR (376 MHz, CDCl$_3$) δ −107.1 |
| 19 | ESIMS m/z 419 ([M + H]$^+$) | $^1$H NMR (400 MHz, CDCl$_3$) δ 9.07 (s, 1H), 8.94 (s, 2H), 7.74-7.69 (m, 2H), 7.64-7.59 (m, 4H), 7.58-7.54 (m, 2H), 2.55 (s, 1H), 1.20 (s, 9H) $^{19}$F NMR (376 MHz, CDCl$_3$) δ −42.7 |
| 20 | ESIMS m/z 453 ([M + H]$^+$) | $^1$H NMR (400 MHz, CDCl$_3$) δ 9.09 (s, 1H), 8.65 (s, 2H), 8.20-8.13 (m, 1H), 7.77-7.72 (m, 2H), 7.63-7.58 (m, 2H), 7.57-7.53 (m, 2H), 3.74 (s, 1H), 1.29 (s, 9H) $^{19}$F NMR (376 MHz, CDCl$_3$) δ −42.5 |
| 21 | ESIMS m/z 437 ([M + H]$^+$) | $^1$H NMR (400 MHz, CDCl$_3$) δ 9.09 (s, 1H), 8.85 (s, 2H), 7.91 (t, J = 8.5 Hz, 1H), 7.77-7.66 (m, 2H), 7.63-7.55 (m, 2H), 7.41 (dd, J = 8.3, 2.0 Hz, 1H), 7.20 (dd, J = 13.8, 2.0 Hz, 1H), 3.05 (d, J = 8.7 Hz, 1H), 1.26 (s, 9H) $^{19}$F NMR (376 MHz, CDCl$_3$) δ −42.55, −106.8 |
| 22 | ESIMS m/z 388 ([M + H]$^+$) | $^1$H NMR (400 MHz, CDCl$_3$) δ 9.08 (s, 1H), 8.65 (s, 2H), 8.14 (dt, J = 8.5, 0.9 Hz, 1H), 7.53-7.47 (m, 4H), 7.46-7.41 (m, 2H), 3.77 (s, 1H), 1.29 (s, 9H) $^{13}$C NMR (126 MHz, CDCl$_3$) δ 156.8, 156.1, 141.1, 139.6, 138.1, 136.8, 134.5, 134.3, 131.0, 130.7, 129.2, 128.2, 124.2, 80.9, 39.5, 27.2 |
| 23 | ESIMS m/z 422 ([M + H]$^+$) | $^1$H NMR (400 MHz, CDCl$_3$) δ 9.10 (s, 1H), 8.93 (d, J = 2.2 Hz, 1H), 8.66 (s, 2H), 8.26-8.21 (m, 1H), 8.05-8.00 (m, 1H), 7.79 (dd, J = 8.2, 0.9 Hz, 1H), 7.61-7.55 (m, 2H), 3.71 (s, 1H), 1.30 (s, 9H) $^{19}$F NMR (376 MHz, CDCl$_3$) δ −67.8 |
| 24 | ESIMS m/z 406 ([M + H]$^+$) | $^1$H NMR (400 MHz, CDCl$_3$) δ 9.09 (s, 1H), 8.93 (d, J = 2.2 Hz, 1H), 8.87 (s, 2H), 8.04-7.96 (m, 2H), 7.78 (dd, J = 8.2, 0.8 Hz, 1H), 7.44 (dd, J = 8.3, 2.0 Hz, 1H), 7.21 (dd, J = 13.3, 1.9 Hz, 1H), 2.99 (dd, J = 7.9, 3.2 Hz, 1H), 1.27 (s, 9H) $^{19}$F NMR (376 MHz, CDCl$_3$) δ −67.8, −105.7 |
| 25 | ESIMS m/z 451 ([M + H]$^+$) | $^1$H NMR (400 MHz, CDCl$_3$) δ 9.08 (s, 1H), 8.65 (s, 2H), 8.12 (dd, J = 7.9, 0.9 Hz, 1H), 7.56-7.47 (m, 4H), 7.05-7.01 (m, 2H), 4.40 (q, J = 8.1 Hz, 2H), 3.78 (s, 1H), 1.28 (s, 9H) $^{19}$F NMR (376 MHz, CDCl$_3$) δ −73.9 |
| 26 | ESIMS m/z 435 ([M + H]$^+$) | $^1$H NMR (400 MHz, CDCl$_3$) δ 9.08 (s, 1H), 8.84 (s, 2H), 7.85 (t, J = 8.5 Hz, 1H), 7.57-7.46 (m, 2H), 7.36 (dd, J = 8.3, 2.0 Hz, 1H), 7.15 (dd, J = 14.2, 2.0 Hz, 1H), 7.06-6.99 (m, 2H), 4.40 (q, J = 8.1 Hz, 2H), 3.05 (d, J = 9.6 Hz, 1H), 1.25 (s, 9H) $^{19}$F NMR (376 MHz, CDCl$_3$) δ −73.90, −107.5 |
| 27 | ESIMS m/z 353 ([M + H]$^+$) | $^1$H NMR (400 MHz, CDCl$_3$) δ 9.10 (s, 1H), 8.66 (s, 2H), 8.15-8.12 (m, 1H), 7.59-7.53 (m, 4H), 7.49-7.44 (m, 2H), 7.42-7.39 (m, 1H), 3.80 (s, 1H), 1.29 (s, 9H) $^{13}$C NMR (126 MHz, CDCl$_3$) δ 156.6, 156.1, 142.4, 139.1, 138.4, 138.2, 134.2, 131.2, 130.5, 129.0, 128.3, 127.8, 126.9, 124.4, 80.9, 39.5, 27.2 |

TABLE 2-continued

Analytical Data.

| Compound Number | Mass Spec | NMR $^1$H, $^{13}$C, $^{19}$F |
|---|---|---|
| 28 | ESIMS m/z 337 ([M + H]$^+$) | $^1$H NMR (400 MHz, CDCl$_3$) δ 9.10 (s, 1H), 8.85 (s, 2H), 7.86 (t, J = 8.5 Hz, 1H), 7.59-7.53 (m, 2H), 7.49-7.35 (m, 5H), 7.20 (dd, J = 14.2, 1.9 Hz, 1H), 3.12-3.05 (m, 1H), 1.26 (s, 9H) $^{19}$F NMR (376 MHz, CDCl$_3$) δ −107.6 |
| 29 | ESIMS m/z 405 ([M + H]$^+$) | $^1$H NMR (400 MHz, CDCl$_3$) δ 9.08 (s, 1H), 8.94 (s, 2H), 7.67-7.62 (m, 2H), 7.59-7.47 (m, 4H), 7.45-7.40 (m, 1H), 2.53 (s, 1H), 1.21 (s, 9H) $^{19}$F NMR (376 MHz, CDCl$_3$) δ −62.7, −115.4 |
| 30 | ESIMS m/z 439 ([M + H]$^+$) | $^1$H NMR (400 MHz, CDCl$_3$) δ 9.09 (s, 1H), 9.07 (d, J = 5.6 Hz, 0H), 8.66 (s, 2H), 8.61 (d, J = 5.6 Hz, 1H), 8.20-8.16 (m, 1H), 7.57-7.43 (m, 6H), 3.76 (s, 1H), 1.30 (s, 9H) $^{19}$F NMR (376 MHz, CDCl$_3$) δ −62.8, −114.9 |
| 31 | ESIMS m/z 423 ([M + H]$^+$) | $^1$H NMR (400 MHz, CDCl$_3$) δ 9.09 (s, 1H), 8.86 (s, 2H), 7.93 (t, J = 8.5 Hz, 1H), 7.59-7.48 (m, 2H), 7.47-7.37 (m, 2H), 7.19 (dt, J = 13.6, 1.6 Hz, 1H), 3.02 (d, J = 8.7 Hz, 1H), 1.27 (s, 9H) $^{19}$F NMR (376 MHz, CDCl$_3$) δ −62.8, −106.8, −114.9 |
| 32 | ESIMS m/z 384 ([M + H]$^+$) | $^1$H NMR (400 MHz, CDCl$_3$) δ 9.06 (s, 1H), 8.93 (s, 2H), 7.63-7.58 (m, 2H), 7.59-7.50 (m, 4H), 7.39-7.33 (m, 2H), 2.57 (d, J = 0.9 Hz, 1H), 1.80-1.72 (m, 2H), 1.49-1.41 (m, 2H), 1.20 (s, 9H) $^{13}$C NMR (126 MHz, CDCl$_3$) δ 156.7, 156.4, 143.2, 139.6, 139.2, 138.8, 135.3, 128.7, 127.4, 126.4, 126.2, 122.4, 80.9, 39.4, 29.7, 26.9, 18.3, 13.6 |
| 33 | ESIMS m/z 375 ([M + H]$^+$) | $^1$H NMR (400 MHz, CDCl$_3$) δ 9.06 (s, 1H), 8.93 (s, 2H), 7.61-7.44 (m, 8H), 2.64 (s, 1H), 1.36 (s, 9H), 1.19 (s, 9H) $^{13}$C NMR (126 MHz, CDCl$_3$) δ 156.6, 156.4, 150.6, 142.5, 140.0, 138.9, 137.2, 128.6, 126.6, 126.4, 125.8, 80.9, 39.4, 34.5, 31.3, 26.9 |
| 34 | ESIMS m/z 417 ([M + H]$^+$) | $^1$H NMR (400 MHz, CDCl$_3$) δ 9.07 (s, 1H), 8.65 (s, 2H), 7.99 (d, J = 8.3 Hz, 1H), 7.61-7.54 (m, 2H), 7.38 (d, J = 8.3 Hz, 1H), 7.33-7.26 (m, 3H), 2.41 (s, 1H), 2.01 (s, 3H), 1.27 (s, 9H) $^{19}$F NMR (376 MHz, CDCl$_3$) δ −57.8 |
| 35 | ESIMS m/z 433 ([M + H]$^+$) | $^1$H NMR (400 MHz, CDCl$_3$) δ 9.08 (s, 1H), 8.65 (s, 2H), 8.00 (d, J = 8.4 Hz, 1H), 7.72 (d, J = 8.3 Hz, 2H), 7.64-7.58 (m, 2H), 7.45-7.38 (m, 1H), 7.35 (d, J = 2.2 Hz, 1H), 2.37 (s, 1H), 2.02 (s, 3H), 1.28 (s, 9H) $^{19}$F NMR (376 MHz, CDCl$_3$) δ −42.7 |
| 36 | ESIMS m/z 399 ([M + H]$^+$) | $^1$H NMR (400 MHz, CDCl$_3$) δ 9.07 (s, 1H), 8.65 (s, 2H), 7.98 (d, J = 8.4 Hz, 1H), 7.59-7.51 (m, 2H), 7.38 (ddd, J = 8.2, 2.4, 0.6 Hz, 1H), 7.31 (d, J = 2.2 Hz, 1H), 7.23-7.16 (m, 2H), 6.55 (t, J = 73.8 Hz, 2H), 2.36 (s, 1H), 2.01 (s, 3H), 1.27 (s, 9H) $^{19}$F NMR (376 MHz, CDCl$_3$) δ −80.8 |
| 37 | ESIMS m/z 358 ([M + H]$^+$) | $^1$H NMR (400 MHz, CDCl$_3$) δ 9.07 (d, J = 0.9 Hz, 1H), 8.65 (s, 2H), 8.01 (d, J = 8.4 Hz, 1H), 7.76-7.71 (m, 2H), 7.70-7.66 (m, 2H), 7.42 (dd, J = 8.4, 2.3 Hz, 1H), 7.35 (d, J = 2.2 Hz, 1H), 2.43 (s, 1H), 2.03 (s, 3H), 1.27 (s, 9H) $^{13}$C NMR (126 MHz, CDCl$_3$) δ 156.7, 156.1, 144.5, 141.9, 140.3, 138.6, 137.4, 132.9, 132.6, 129.1, 127.5, 123.0, 118.8, 111.2, 81.2, 65.8, 39.8, 27.3, 23.0, 15.3 |
| 38 | ESIMS m/z 398 ([M + H]$^+$) | $^1$H NMR (400 MHz, CDCl$_3$) δ 9.06 (s, 1H), 8.64 (s, 2H), 7.98 (d, J = 8.4 Hz, 1H), 7.59-7.52 (m, 2H), 7.41-7.34 (m, 3H), 7.33-7.31 (m, 1H), 2.41 (s, 1H), 2.00 (s, 3H), 1.80-1.73 (m, 2H), 1.48-1.39 (m, 2H), 1.27 (s, 9H) $^{13}$C NMR (126 MHz, CDCl$_3$) δ 156.6, 156.1, 140.8, 139.8, 139.7, 139.4, 137.5, 135.4, 132.7, 128.9, 127.4, 126.2, 122.8, 122.5, 81.2, 39.8, 27.4, 23.0, 18.3, 13.6 |
| 39 | ESIMS m/z 389 ([M + H]$^+$) | $^1$H NMR (400 MHz, CDCl$_3$) δ 9.06 (s, 1H), 8.65 (s, 2H), 7.97 (d, J = 8.3 Hz, 1H), 7.54-7.48 (m, 2H), 7.50-7.43 (m, 2H), 7.41 (dd, J = 8.4, 2.2 Hz, 1H), 7.34 (d, J = 2.2 Hz, 1H), 2.40 (s, 1H), 1.99 (s, 3H), 1.36 (s, 9H), 1.27 (s, 9H) $^{13}$C NMR (126 MHz, CDCl$_3$) δ 156.6, 156.1, 50.6, 140.6, 140.1, 139.5, 137.7, 137.1, 132.7, 128.8, 126.6, 125.8, 122.7, 81.2, 39.8, 34.6, 31.3, 22.9. |

TABLE 2-continued

Analytical Data.

| Compound Number | Mass Spec | NMR $^1$H, $^{13}$C, $^{19}$F |
|---|---|---|
| 40 | ESIMS m/z 431 ([M + H]$^+$) | $^1$H NMR (400 MHz, CDCl$_3$) δ 9.07 (s, 1H), 8.66 (s, 2H), 7.96 (d, J = 8.2 Hz, 1H), 7.21 (d, J = 8.2 Hz, 1H), 7.15-7.04 (m, 4H), 2.40 (s, 1H), 2.28 (s, 3H), 1.97 (s, 3H), 1.28 (s, 9H) $^{19}$F NMR (376 MHz, CDCl$_3$) δ −57.7 |
| 41 | ESIMS m/z 435 ([M + H]$^+$) | $^1$H NMR (400 MHz, CDCl$_3$) δ 9.08 (s, 1H), 8.66 (s, 2H), 8.00 (d, J = 8.4 Hz, 1H), 7.44 (t, J = 8.5 Hz, 1H), 7.36 (d, J = 8.3 Hz, 1H), 7.28 (d, J = 2.0 Hz, 1H), 7.13-7.03 (m, 2H), 2.38 (s, 1H), 2.00 (s, 3H), 1.28 (s, 9H) $^{19}$F NMR (376 MHz, CDCl$_3$) δ −57.98, −113.4 |
| 42 | ESIMS m/z 400 ([M + H]$^+$) | $^1$H NMR (400 MHz, CDCl$_3$) δ 9.06 (s, 1H), 8.65 (s, 2H), 7.99 (d, J = 8.3 Hz, 1H), 7.62-7.57 (m, 2H), 7.57-7.50 (m, 2H), 7.44-7.39 (m, 1H), 7.36-7.32 (m, 1H), 2.47 (s, 1H), 2.01 (s, 3H), 1.77 (s, 6H), 1.27 (s, 9H) $^{13}$C NMR (126 MHz, CDCl$_3$) δ 156.6, 156.1, 140.8, 140.7, 139.8, 139.7, 139.6, 137.6, 132.8, 128.9, 127.4, 125.6, 124.4, 122.8, 81.2, 39.8, 36.9, 29.1, 27.4, 23.0 |
| 43 | ESIMS m/z 372 ([M + H]$^+$) | $^1$H NMR (400 MHz, CDCl$_3$) δ 9.07 (s, 1H), 8.65 (s, 2H), 7.99 (d, J = 8.4 Hz, 1H), 7.63-7.56 (m, 2H), 7.41 (dd, J = 8.0, 0.7 Hz, 3H), 7.37-7.32 (m, 1H), 3.80 (s, 2H), 2.39 (s, 1H), 2.01 (s, 3H), 1.27 (s, 9H) $^{13}$C NMR (126 MHz, CDCl$_3$) δ 156.6, 156.1, 140.9, 139.9, 139.9, 139.7, 137.5, 132.7, 129.1, 128.9, 128.4, 127.6, 122.8, 117.7, 81.2, 39.8, 27.4, 23.4, 23.0 |
| 44 | ESIMS m/z 433 ([M + H]$^+$) | $^1$H NMR (400 MHz, CDCl$_3$) δ 9.05 (s, 1H), 8.69 (s, 2H), 7.91 (d, J = 8.2 Hz, 1H), 7.61-7.53 (m, 2H), 7.30 (ddt, J = 7.7, 2.0, 1.0 Hz, 2H), 7.20 (dd, J = 8.2, 1.9 Hz, 1H), 7.02 (s, 1H), 4.96 (s, 1H), 3.57 (s, 3H), 1.25 (s, 9H) $^{19}$F NMR (376 MHz, CDCl$_3$) δ −57.8 |
| 45 | ESIMS m/z 415 ([M + H]$^+$) | $^1$H NMR (400 MHz, CDCl$_3$) δ 9.04 (s, 1H), 8.68 (s, 2H), 7.89 (d, J = 8.2 Hz, 1H), 7.59-7.48 (m, 2H), 7.23-7.17 (m, 3H), 7.02 (d, J = 1.9 Hz, 1H), 6.56 (t, J = 73.7 Hz, 1H), 4.98 (s, 1H), 3.58 (s, 3H), 1.25 (s, 9H) $^{19}$F NMR (376 MHz, CDCl$_3$) δ −80.9 |
| 46 | ESIMS m/z 449 ([M + H]$^+$) | $^1$H NMR (400 MHz, CDCl$_3$) δ 9.04 (s, 1H), 8.68 (s, 2H), 7.92 (d, J = 8.2 Hz, 1H), 7.76-7.71 (m, 2H), 7.62-7.56 (m, 2H), 7.23 (dd, J = 8.2, 1.9 Hz, 1H), 7.05 (d, J = 1.8 Hz, 1H), 4.96 (s, 1H), 3.59 (s, 3H), 1.25 (s, 9H) $^{19}$F NMR (376 MHz, CDCl$_3$) δ −42.6 |
| 47 | ESIMS m/z 374 ([M + H]$^+$) | $^1$H NMR (400 MHz, CDCl$_3$) δ 9.04 (s, 1H), 8.68 (s, 2H), 7.94 (d, J = 8.2 Hz, 1H), 7.77-7.71 (m, 2H), 7.69-7.63 (m, 2H), 7.24 (dd, J = 8.2, 1.9 Hz, 1H), 7.05 (d, J = 1.8 Hz, 1H), 4.92 (s, 1H), 3.59 (s, 3H), 1.25 (s, 9H) $^{13}$C NMR (126 MHz, CDCl$_3$) δ 157.7, 156.6, 155.6, 144.5, 140.2, 139.7, 132.7, 129.5, 127.7, 119.1, 118.7, 111.7, 111.5, 80.3, 55.7, 38.8, 26.9 |
| 48 | ESIMS m/z 388 ([M + H]$^+$) | $^1$H NMR (400 MHz, CDCl$_3$) δ 9.04 (s, 1H), 8.69 (s, 2H), 7.90 (d, J = 8.2 Hz, 1H), 7.62-7.54 (m, 2H), 7.47-7.35 (m, 2H), 7.22 (dd, J = 8.2, 1.9 Hz, 1H), 7.04 (d, J = 1.8 Hz, 1H), 4.98 (s, 1H), 3.81 (s, 2H), 3.58 (s, 3H), 1.25 (s, 9H) $^{13}$C NMR (126 MHz, CDCl$_3$) δ 157.52, 156.5, 155.7, 141.2, 139.9, 131.7, 129.4, 129.2, 128.5, 127.7, 118.9, 117.7, 111.7, 80.3, 55.6, 38.8, 26.9, 23.4 |
| 49 | ESIMS m/z 414 ([M + H]$^+$) | $^1$H NMR (400 MHz, CDCl$_3$) δ 9.04 (s, 1H), 8.68 (s, 2H), 7.90 (d, J = 8.2 Hz, 1H), 7.58-7.51 (m, 2H), 7.40-7.34 (m, 2H), 7.20 (dd, J = 8.2, 1.8 Hz, 1H), 7.03 (d, J = 1.8 Hz, 1H), 4.98 (s, 1H), 3.58 (s, 3H), 1.81-1.74 (m, 2H), 1.48-1.43 (m, 2H), 1.25 (s, 9H) $^{13}$C NMR (126 MHz, CDCl$_3$) δ 157.5, 156.5, 155.7, 141.2, 139.9, 139.5, 135.7, 131.6, 129.2, 127.5, 126.2, 122.3, 118.8, 111.7, 80.3, 55.6, 38.8, 26.9, 18.4, 13.6 |

TABLE 2-continued

Analytical Data.

| Compound Number | Mass Spec | NMR $^1$H, $^{13}$C, $^{19}$F |
|---|---|---|
| 50 | ESIMS m/z 416 ([M + H]$^+$) | $^1$H NMR (400 MHz, CDCl$_3$) δ 9.04 (s, 1H), 8.69 (s, 2H), 7.90 (d, J = 8.2 Hz, 1H), 7.61-7.52 (m, 4H), 7.22 (dd, J = 8.2, 1.9 Hz, 1H), 7.05 (d, J = 1.8 Hz, 1H), 4.98 (s, 1H), 3.58 (s, 3H), 1.77 (s, 6H), 1.25 (s, 9H) $^{13}$C NMR (126 MHz, CDCl$_3$) δ 157.5, 156.5, 155.7, 141.3, 141.0, 139.9, 139.7, 131.6, 129.2, 127.5, 125.7, 124.4, 118.9, 111.7, 80.3, 55.6, 38.8, 36.9, 29.1, 26.9 |
| 51 | ESIMS m/z 405 ([M + H]$^+$) | $^1$H NMR (400 MHz, CDCl$_3$) δ 9.03 (s, 1H), 8.69 (s, 2H), 7.87 (d, J = 8.2 Hz, 1H), 7.53-7.43 (m, 4H), 7.22 (dd, J = 8.2, 1.8 Hz, 1H), 7.06 (d, J = 1.8 Hz, 1H), 5.02 (s, 1H), 3.56 (s, 3H), 1.36 (s, 9H), 1.25 (s, 9H) $^{13}$C NMR (126 MHz, CDCl$_3$) δ 157.4, 156.5, 155.7, 150.9, 142.2, 140.0, 137.2, 130.9, 129.0, 126.7, 125.8, 118.8, 111.7, 80.3, 55.5, 38.8, 34.6, 31.3, 26.9 |
| 52 | ESIMS m/z 447 ([M + H]$^+$) | $^1$H NMR (400 MHz, CDCl$_3$) δ 9.04 (s, 1H), 8.69 (s, 2H), 7.88 (d, J = 8.1 Hz, 1H), 7.22 (d, J = 8.3 Hz, 1H), 7.14-7.07 (m, 2H), 6.94 (dd, J = 8.1, 1.8 Hz, 1H), 6.78 (d, J = 1.7 Hz, 1H), 4.99 (s, 1H), 3.51 (s, 3H), 2.28 (s, 3H), 1.26 (s, 9H) $^{19}$F NMR (376 MHz, CDCl$_3$) δ −57.7 |
| 53 | ESIMS m/z 451 ([M + H]$^+$) | $^1$H NMR (400 MHz, CDCl$_3$) δ 9.04 (s, 1H), 8.69 (s, 2H), 7.92 (d, J = 8.3 Hz, 1H), 7.46 (t, J = 8.5 Hz, 1H), 7.16 (dt, J = 8.3, 1.6 Hz, 1H), 7.10 (dddd, J = 17.4, 10.7, 2.4, 1.2 Hz, 2H), 7.02 (t, J = 1.6 Hz, 1H), 4.97 (s, 1H), 3.55 (s, 3H), 1.25 (s, 9H) $^{19}$F NMR (376 MHz, CDCl$_3$) δ −57.98, −113.2 |
| 54 | ESIMS m/z 402 ([M + H]$^+$) | $^1$H NMR (400 MHz, CDCl$_3$) δ 8.84 (dd, J = 2.4, 0.8 Hz, 1H), 8.48 (dd, J = 4.8, 1.6 Hz, 1H), 7.89 (ddd, J = 8.1, 2.4, 1.6 Hz, 1H), 7.64-7.55 (m, 4H), 7.51-7.46 (m, 2H), 7.30-7.22 (m, 3H), 2.42 (s, 1H), 1.20 (s, 9H) $^{19}$F NMR (376 MHz, CDCl$_3$) δ −57.8 |
| 55 | ESIMS m/z 419 ([M + H]$^+$) | $^1$H NMR (400 MHz, CDCl$_3$) δ 8.86-8.81 (m, 1H), 8.47 (dd, J = 4.7, 1.6 Hz, 1H), 7.87 (ddd, J = 8.1, 2.5, 1.6 Hz, 1H), 7.71 (d, J = 8.3 Hz, 2H), 7.65-7.60 (m, 4H), 7.55-7.50 (m, 2H), 7.23 (ddd, J = 8.2, 4.8, 0.8 Hz, 1H), 2.44 (s, 1H), 1.21 (s, 9H) $^{19}$F NMR (376 MHz, CDCl$_3$) δ −42.7 |
| 56 | ESIMS m/z 384 ([M + H]$^+$) | $^1$H NMR (400 MHz, CDCl$_3$) δ 8.82 (dd, J = 2.5, 0.9 Hz, 1H), 8.46 (dd, J = 4.7, 1.6 Hz, 1H), 7.88-7.84 (m, 1H), 7.62-7.53 (m, 4H), 7.51-7.44 (m, 2H), 7.22 (ddd, J = 8.1, 4.7, 0.9 Hz, 1H), 7.20-7.15 (m, 2H), 6.54 (t, J = 73.9 Hz, 1H), 2.43 (s, 1H), 1.20 (s, 9H) $^{19}$F NMR (376 MHz, CDCl$_3$) δ −80.7 |
| 57 | ESIMS m/z 416 ([M + H]$^+$) | $^1$H NMR (400 MHz, CDCl$_3$) δ 8.85-8.81 (m, 1H), 8.47 (dd, J = 4.8, 1.6 Hz, 1H), 7.87 (ddd, J = 8.1, 2.6, 1.8 Hz, 1H), 7.59 (d, J = 8.2 Hz, 2H), 7.56-.51 (m, 2H), 7.50-7.45 (m, 2H), 7.25-7.20 (m, 1H), 7.03-6.97 (m, 2H), 4.39 (q, J = 8.1 Hz, 2H), 2.40 (s, 1H), 1.20 (s, 9H) $^{19}$F NMR (376 MHz, CDCl$_3$) δ −73.9 |
| 58 | ESIMS m/z 343 ([M + H]$^+$) | $^1$H NMR (400 MHz, CDCl$_3$) δ 8.82 (dd, J = 2.5, 0.9 Hz, 1H), 8.46 (dd, J = 4.7, 1.6 Hz, 1H), 7.88 (ddd, J = 8.2, 2.5, 1.7 Hz, 1H), 7.71 (d, J = 2.1 Hz, 1H), 7.69-7.61 (m, 4H), 7.55-7.49 (m, 2H), 7.23 (ddd, J = 8.2, 4.8, 0.9 Hz, 1H), 2.51 (s, 1H), 1.20 (s, 9H) $^{13}$C NMR (126 MHz, CDCl$_3$) δ 149.6, 147.8, 145.6, 144.9, 141.1, 137.6, 135.9, 132.6, 129.2, 127.6, 126.3, 122.4, 118.9, 110.9, 81.8, 39.4, 27.2 |
| 59 | ESIMS m/z 357 ([M + H]$^+$) | $^1$H NMR (400 MHz, CDCl$_3$) δ 8.86-8.80 (m, 1H), 8.46 (dd, J = 4.7, 1.7 Hz, 1H), 7.87 (ddd, J = 8.1, 2.4, 1.5 Hz, 1H), 7.64-7.55 (m, 4H), 7.55-7.49 (m, 2H), 7.42-7.37 (m, 2H), 7.22 (dd, J = 8.2, 4.7 Hz, 1H), 3.79 (s, 2H), 2.49 (s, 1H), 1.20 (s, 9H) $^{13}$C NMR (126 MHz, CDCl$_3$) δ 149.6, 147.7, 144.5, 141.2, 140.3, 138.6, 135.9, 128.9, 128.4, 127.7, 126.1, 122.3, 117.8, 81.8, 39.4, 27.2, 23.3 |
| 60 | ESIMS m/z 383 ([M + H]$^+$) | $^1$H NMR (400 MHz, CDCl$_3$) δ 8.85-8.79 (m, 1H), 8.45 (dd, J = 4.8, 1.6 Hz, 1H), 7.87 (ddd, J = 8.1, 2.4, 1.6 Hz, 1H), 7.63-7.58 (m, 2H), 7.57-7.53 (m, 2H), 7.52-7.45 (m, 2H), 7.37-7.32 (m, 2H), 7.22 (ddd, J = 8.1, 4.7, 0.8 Hz, 1H), 2.53 (s, 1H), 1.78-1.71 (m, 2H), 1.46-1.40 (m, 2H), 1.20 (s, 9H) |

TABLE 2-continued

Analytical Data.

| Compound Number | Mass Spec | NMR $^1$H, $^{13}$C, $^{19}$F |
|---|---|---|
| | | $^{13}$C NMR (126 MHz, CDCl$_3$) δ 149.6, 147.7, 144.4, 141.2, 139.8, 138.6, 135.9, 135.1, 130.7, 128.9, 127.4, 126.1, 126.0, 122.5, 122.3, 81.8, 39.4, 27.2, 18.3, 13.6 |
| 61 | ESIMS m/z 385 ([M + H]$^+$) | $^1$H NMR (400 MHz, CDCl$_3$) δ 8.82 (dd, J = 2.5, 1.2 Hz, 1H), 8.45 (dd, J = 4.8, 1.9 Hz, 1H), 7.88 (ddd, J = 8.2, 2.5, 1.6 Hz, 1H), 7.60 (tt, J = 5.9, 2.0 Hz, 4H), 7.56-7.48 (m, 4H), 7.25-7.20 (m, 1H), 1.76 (s, 6H), 1.20 (s, 9H) $^{13}$C NMR (126 MHz, CDCl$_3$) δ 149.6, 147.6, 144.4, 141.2, 140.5, 139.9, 138.7, 135.9, 128.9, 127.4, 126.1, 125.6, 124.5, 122.3, 81.8, 39.3, 36.9, 29.1, 27.2 |
| 62 | ESIMS m/z 374 ([M + H]$^+$) | $^1$H NMR (400 MHz, CDCl$_3$) δ 8.83 (d, J = 2.4 Hz, 1H), 8.46 (dd, J = 4.7, 1.6 Hz, 1H), 7.87 (ddd, J = 8.2, 2.4, 1.5 Hz, 1H), 7.63-7.56 (m, 2H), 7.55-7.49 (m, 4H), 7.48-7.43 (m, 2H), 7.22 (ddd, J = 8.2, 4.8, 0.9 Hz, 1H), 2.47 (s, 1H), 1.36 (s, 9H), 1.20 (s, 9H) $^{13}$C NMR (126 MHz, CDCl$_3$) δ 150.4, 149.5, 147.5, 143.8, 141.3, 139.5, 137.5, 136.0, 128.8, 126.3, 125.7, 122.2, 81.9, 39.4, 34.5, 31.3, 27.2 |
| 63 | ESIMS m/z 416 ([M + H]$^+$) | $^1$H NMR (400 MHz, CDCl$_3$) δ 8.85-8.78 (m, 1H), 8.46 (dd, J = 4.8, 1.6 Hz, 1H), 7.92 (ddd, J = 8.1, 2.4, 1.5 Hz, 1H), 7.63-7.55 (m, 2H), 7.26-7.18 (m, 4H), 7.13-7.05 (m, 2H), 2.49 (s, 1H), 2.26 (s, 3H), 1.21 (s, 9H) $^{19}$F NMR (376 MHz, CDCl$_3$) δ −57.7 |
| 64 | ESIMS m/z 436 ([M + H]$^+$) | $^1$H NMR (400 MHz, CDCl$_3$) δ 8.49-8.46 (m, 2H), 8.20-8.15 (m, 1H), 7.65 (ddd, J = 8.1, 2.5, 1.7 Hz, 1H), 7.60-7.55 (m, 2H), 7.51-7.45 (m, 2H), 7.33-7.28 (m, 2H), 7.21 (ddd, J = 8.1, 4.8, 0.8 Hz, 1H), 3.86 (s, 1H), 1.28 (s, 9H) $^{19}$F NMR (376 MHz, CDCl$_3$) δ −57.8 |
| 65 | ESIMS m/z 452 ([M + H]$^+$) | $^1$H NMR (400 MHz, CDCl$_3$) δ 8.47 (dd, J = 4.7, 1.7 Hz, 2H), 8.21-8.16 (m, 1H), 7.76-7.71 (m, 2H), 7.65 (ddd, J = 8.0, 2.4, 1.6 Hz, 1H), 7.63-7.57 (m, 2H), 7.56-7.49 (m, 2H), 7.21 (ddd, J = 8.0, 4.8, 0.8 Hz, 1H), 3.85 (s, 1H), 1.28 (s, 9H) $^{19}$F NMR (376 MHz, CDCl$_3$) δ −42.5 |
| 66 | ESIMS m/z 418 ([M + H]$^+$) | $^1$H NMR (400 MHz, CDCl$_3$) δ 8.49-8.45 (m, 2H), 8.18-8.11 (m, 1H), 7.65 (ddd, J = 8.0, 2.4, 1.6 Hz, 1H), 7.57-7.53 (m, 2H), 7.51-7.45 (m, 2H), 7.22-7.18 (m, 3H), 6.56 (t, J = 73.7 Hz, 1H), 3.86 (s, 1H), 1.28 (s, 9H) $^{19}$F NMR (376 MHz, CDCl$_3$) δ −80.9. |
| 67 | ESIMS m/z 450 ([M + H]$^+$) | $^1$H NMR (400 MHz, CDCl$_3$) δ 8.50-8.43 (m, 2H), 8.14 (d, J = 9.0 Hz, 1H), 7.64 (ddd, J = 8.0, 2.4, 1.6 Hz, 1H), 7.55-7.50 (m, 2H), 7.49-7.43 (m, 2H), 7.20 (ddd, J = 8.1, 4.8, 0.8 Hz, 1H), 7.05-6.99 (m, 2H), 4.40 (q, J = 8.1 Hz, 2H), 3.88 (s, 1H), 1.27 (s, 9H) $^{19}$F NMR (376 MHz, CDCl$_3$) δ −73.9 |
| 68 | ESIMS m/z 377 ([M + H]$^+$) | $^1$H NMR (400 MHz, CDCl$_3$) δ 8.50-8.43 (m, 2H), 8.21 (d, J = 8.9 Hz, 1H), 7.78-7.73 (m, 2H), 7.69-7.62 (m, 3H), 7.53 (dq, J = 4.1, 2.2 Hz, 2H), 7.21 (ddd, J = 8.1, 4.8, 0.9 Hz, 1H), 3.84 (s, 1H), 1.28 (s, 9H) $^{13}$C NMR (101 MHz, CDCl$_3$) δ 149.4, 147.8, 143.0, 142.1, 140.0, 139.6, 135.6, 134.9, 132.8, 131.1, 130.9, 127.6, 124.2, 121.8, 118.6, 111.9, 82.1, 65.8, 39.5, 27.5, 15.3 |
| 69 | ESIMS m/z 391 ([M + H]$^+$) | $^1$H NMR (400 MHz, CDCl$_3$) δ 8.51-8.44 (m, 2H), 8.20-8.13 (m, 1H), 7.65 (ddd, J = 8.0, 2.4, 1.6 Hz, 1H), 7.61-7.54 (m, 2H), 7.54-7.44 (m, 2H), 7.46-7.33 (m, 2H), 7.21 (ddd, J = 8.0, 4.7, 0.9 Hz, 1H), 3.86 (s, 1H), 3.81 (s, 2H), 1.28 (s, 9H) $^{13}$C NMR (101 MHz, CDCl$_3$) δ 149.4, 147.7, 141.0, 140.7, 140.2, 138.6, 135.6, 134.6, 130.9, 130.7, 129.8, 128.6, 127.6, 124.0, 121.8, 82.2, 39.4, 27.5, 23.4 |
| 70 | ESIMS m/z 417 ([M + H]$^+$) | $^1$H NMR (400 MHz, CDCl$_3$) δ 8.50-8.44 (m, 2H), 8.16 (d, J = 8.9 Hz, 1H), 7.64 (ddd, J = 8.0, 2.5, 1.6 Hz, 1H), 7.57-7.52 (m, 2H), 7.50 (dq, J = 4.8, 2.1 Hz, 2H), 7.40-7.33 (m, 2H), 7.20 (ddd, J = 8.1, 4.8, 0.9 Hz, 1H), 3.87 (s, 1H), 1.81-1.75 (m, 2H), 1.49-1.43 (m, 2H), 1.28 (s, 9H) |

TABLE 2-continued

Analytical Data.

| Compound Number | Mass Spec | NMR $^1$H, $^{13}$C, $^{19}$F |
|---|---|---|
| | | $^{13}$C NMR (101 MHz, CDCl$_3$) δ 149.5, 147.7, 140.9, 140.7, 140.2, 138.0, 136.0, 135.6, 134.6, 130.9, 130.6, 127.4, 126.3, 123.9, 122.3, 121.8, 82.1, 39.4, 30.3, 27.5, 18.4, 15.3, 13.6 |
| 71 | ESIMS m/z 419 ([M + H]$^+$) | $^1$H NMR (400 MHz, CDCl$_3$) δ 8.50-8.45 (m, 2H), 8.17 (d, J = 8.9 Hz, 1H), 7.68-7.63 (m, 1H), 7.61-7.54 (m, 4H), 7.51 (h, J = 2.1 Hz, 2H), 7.21 (ddd, J = 8.0, 4.8, 0.9 Hz, 1H), 3.88 (s, 1H), 1.77 (s, 6H), 1.28 (s, 9H)<br>$^{13}$C NMR (101 MHz, CDCl$_3$) δ 149.5, 147.7, 141.4, 140.9, 140.8, 140.3, 138.2, 135.6, 134.6, 130.9, 130.6, 127.4, 125.8, 124.3, 124.0, 121.8, 82.1, 65.8, 39.4, 37.0, 29.1, 27.5 |
| 72 | ESIMS m/z 408 ([M + H]$^+$) | $^1$H NMR (400 MHz, CDCl$_3$) δ 8.51-8.48 (m, 1H), 8.47 (dd, J = 4.8, 1.6 Hz, 1H), 8.16-8.11 (m, 1H), 7.67-7.61 (m, 1H), 7.54-7.45 (m, 6H), 7.20 (ddd, J = 8.1, 4.8, 0.9 Hz, 1H), 3.91 (s, 1H), 1.36 (s, 9H), 1.28 (s, 9H)<br>$^{13}$C NMR (101 MHz, CDCl$_3$) δ 151.3, 149.4, 147.5, 141.7, 140.4, 140.2, 135.7, 134.4, 130.9, 130.5, 126.6, 125.9, 123.9, 121.8, 82.1, 65.8, 39.4, 34.6, 31.3, 27.5 |
| 73 | ESIMS m/z 450 ([M + H]$^+$) | $^1$H NMR (400 MHz, CDCl$_3$) δ 8.47 (dd, J = 4.8, 1.6 Hz, 1H), 8.45 (dd, J = 2.3, 0.9 Hz, 1H), 8.14 (dt, J = 8.4, 0.8 Hz, 1H), 7.69 (ddd, J = 8.1, 2.5, 1.6 Hz, 1H), 7.25-7.19 (m, 4H), 7.15-7.07 (m, 2H), 3.90 (s, 1H), 2.30 (s, 3H), 1.28 (s, 9H)<br>$^{19}$F NMR (376 MHz, CDCl$_3$) δ −57.7 |
| 74 | ESIMS m/z 435 ([M + H]$^+$) | $^1$H NMR (400 MHz, CDCl$_3$) δ 9.09 (s, 1H), 8.85 (s, 2H), 7.86 (t, J = 8.5 Hz, 1H), 7.21 (d, J = 8.3 Hz, 1H), 7.16-7.08 (m, 3H), 6.92 (dd, J = 13.6, 1.9 Hz, 1H), 3.08 (d, J = 9.6 Hz, 1H), 2.28 (s, 3H), 1.27 (s, 9H)<br>$^{19}$F NMR (376 MHz, CDCl$_3$) δ −57.7, −107.6 |
| 75 | ESIMS m/z 402 ([M + H]$^+$) | $^1$H NMR (400 MHz, CDCl$_3$) δ 9.08 (s, 1H), 8.84 (s, 2H), 7.87 (t, J = 8.5 Hz, 1H), 7.57-7.51 (m, 2H), 7.42-7.32 (m, 3H), 7.17 (dd, J = 14.0, 2.0 Hz, 1H), 3.04 (d, J = 9.5 Hz, 1H), 1.82-1.75 (m, 2H), 1.49-1.39 (m, 2H), 1.26 (s, 9H)<br>$^{19}$F NMR (376 MHz, CDCl$_3$) δ −107.2 |
| 76 | ESIMS m/z 436 ([M + H]$^+$) | $^1$H NMR (400 MHz, CDCl$_3$) δ 9.09 (s, 1H), 8.85 (s, 2H), 8.34 (dd, J = 2.5, 0.7 Hz, 1H), 7.90 (t, J = 8.5 Hz, 1H), 7.82 (dd, J = 8.6, 2.5 Hz, 1H), 7.35 (dd, J = 8.3, 2.0 Hz, 1H), 7.13 (dd, J = 13.8, 2.0 Hz, 1H), 6.95 (dd, J = 8.6, 0.7 Hz, 1H), 4.81 (q, J = 8.5 Hz, 2H), 3.02 (d, J = 8.9 Hz, 1H), 1.26 (s, 9H)<br>$^{19}$F NMR (376 MHz, CDCl$_3$) δ −73.80, −106.7 |
| 77 | ESIMS m/z 404 ([M + H]$^+$) | $^1$H NMR (400 MHz, CDCl$_3$) δ 9.09 (s, 1H), 8.85 (s, 2H), 7.88 (t, J = 8.5 Hz, 1H), 7.62-7.54 (m, 4H), 7.40 (dd, J = 8.3, 2.0 Hz, 1H), 7.19 (dd, J = 14.0, 1.9 Hz, 1H), 3.05 (d, J = 9.4 Hz, 1H), 1.77 (s, 6H), 1.26 (s, 9H)<br>$^{19}$F NMR (376 MHz, CDCl$_3$) δ −107.2 |
| 78 | ESIMS m/z 439 ([M + H]$^+$) | $^1$H NMR (400 MHz, CDCl$_3$) δ 9.09 (s, 1H), 8.85 (s, 2H), 7.90 (t, J = 8.5 Hz, 1H), 7.45 (t, J = 8.5 Hz, 1H), 7.35 (dt, J = 8.3, 1.7 Hz, 1H), 7.20-7.04 (m, 3H), 3.05 (d, J = 9.0 Hz, 1H), 1.26 (s, 9H)<br>$^{19}$F NMR (376 MHz, CDCl$_3$) δ −57.9, −107.1, −113.2 |
| 79 | ESIMS m/z 435 ([M + H]$^+$) | $^1$H NMR (400 MHz, CDCl$_3$) δ 9.11 (s, 1H), 8.85 (s, 2H), 7.79 (t, J = 8.2 Hz, 1H), 7.64-7.57 (m, 2H), 7.45-7.42 (m, 1H), 7.31 (dt, J = 7.7, 1.0 Hz, 2H), 7.22 (dd, J = 13.0, 1.9 Hz, 1H), 3.10 (s, 3H), 1.19 (s, 9H)<br>$^{19}$F NMR (376 MHz, CDCl$_3$) δ −57.8, −98.6 |
| 80 | ESIMS m/z 449 ([M + H]$^+$) | $^1$H NMR (400 MHz, CDCl$_3$) δ 9.12 (s, 1H), 8.86 (d, J = 1.0 Hz, 2H), 7.76 (t, J = 8.2 Hz, 1H), 7.26 (d, J = 8.2 Hz, 1H), 7.18-7.10 (m, 3H), 6.97 (dd, J = 12.6, 1.9 Hz, 1H), 3.11 (s, 3H), 2.31 (s, 3H), 1.20 (s, 9H)<br>$^{19}$F NMR (376 MHz, CDCl$_3$) δ −57.7, −99.1 |
| 81 | ESIMS m/z 453 ([M + H]$^+$) | $^1$H NMR (400 MHz, CDCl$_3$) δ 9.11 (s, 1H), 8.85 (d, J = 1.1 Hz, 2H), 7.79 (t, J = 8.2 Hz, 1H), 7.50 (t, J = 8.5 Hz, 1H), 7.41 (dt, J = 8.3, 1.7 Hz, 1H), 7.21 (dt, J = 12.9, 1.6 Hz, 1H), 7.16-7.07 (m, 2H), 3.10 (s, 3H), 1.19 (s, 9H)<br>$^{19}$F NMR (376 MHz, CDCl$_3$) δ −57.9, −98.7, −113.0 |

TABLE 2-continued

Analytical Data.

| Compound Number | Mass Spec | NMR $^1$H, $^{13}$C, $^{19}$F |
|---|---|---|
| 82 | ESIMS m/z 450 ([M + H]$^+$) | $^1$H NMR (400 MHz, CDCl$_3$) δ 9.11 (s, 1H), 8.85 (d, J = 1.0 Hz, 2H), 8.39 (dd, J = 2.5, 0.8 Hz, 1H), 7.87 (dd, J = 8.6, 2.6 Hz, 1H), 7.81 (d, J = 8.2 Hz, 1H), 7.44-7.37 (m, 1H), 7.19 (dd, J = 12.9, 1.9 Hz, 1H), 6.97 (dd, J = 8.6, 0.8 Hz, 1H), 4.82 (q, J = 8.5 Hz, 2H), 3.10 (s, 3H), 1.19 (s, 9H) $^{19}$F NMR (376 MHz, CDCl$_3$) δ −73.8, −98.3 |
| 83 | ESIMS m/z 449 ([M + H]$^+$) | $^1$H NMR (400 MHz, CDCl$_3$) δ 9.11 (s, 1H), 8.84 (d, J = 0.9 Hz, 2H), 7.76 (t, J = 8.3 Hz, 1H), 7.60-7.54 (m, 2H), 7.42 (dd, J = 8.3, 2.0 Hz, 1H), 7.20 (dd, J = 13.2, 2.0 Hz, 1H), 7.08-7.00 (m, 2H), 4.41 (q, J = 8.1 Hz, 2H), 3.10 (s, 3H), 1.19 (s, 9H) $^{19}$F NMR (376 MHz, CDCl$_3$) δ −73.9, −98.9 |
| 84 | ESIMS m/z 416 ([M + H]$^+$) | $^1$H NMR (400 MHz, CDCl$_3$) δ 9.11 (s, 1H), 8.84 (d, J = 1.0 Hz, 2H), 7.79 (d, J = 8.2 Hz, 1H), 7.62-7.55 (m, 2H), 7.44 (dd, J = 8.3, 2.0 Hz, 1H), 7.41-7.35 (m, 2H), 7.22 (dd, J = 13.1, 1.9 Hz, 1H), 3.10 (s, 3H), 1.81-1.76 (m, 2H), 1.49-1.44 (m, 2H), 1.19 (s, 9H) $^{19}$F NMR (376 MHz, CDCl$_3$) δ −98.7 |
| 85 | ESIMS m/z 418 ([M + H]$^+$) | $^1$H NMR (400 MHz, CDCl$_3$) δ 9.11 (s, 1H), 8.85 (d, J = 1.0 Hz, 2H), 7.79 (t, J = 8.3 Hz, 1H), 7.66-7.60 (m, 2H), 7.61-7.55 (m, 2H), 7.46 (dd, J = 8.3, 1.9 Hz, 1H), 7.24 (dd, J = 13.0, 1.9 Hz, 1H), 3.11 (s, 3H), 1.78 (s, 6H), 1.20 (s, 9H) $^{19}$F NMR (376 MHz, CDCl$_3$) δ −98.7. |
| 86 | ESIMS m/z 420 ([M + H]$^+$) | $^1$H NMR (400 MHz, CDCl$_3$) δ 9.08 (s, 1H), 8.65 (s, 2H), 8.15 (d, J = 9.0 Hz, 1H), 7.58 (d, J = 1.3 Hz, 4H), 7.55-7.51 (m, 2H), 3.80 (s, 1H), 1.77 (s, 6H), 1.29 (s, 9H). $^{13}$C NMR (126 MHz, CDCl$_3$) δ 156.80, 156.14, 141.59, 141.43, 139.59, 138.13, 138.02, 134.33, 131.16, 130.69, 127.48, 125.86, 124.32, 124.29, 81.00, 39.52, 37.02, 29.12, 27.26. |
| 87 | ESIMS m/z 452 ([M + H]$^+$) | $^1$H NMR (400 MHz, CDCl$_3$) δ 9.07 (s, 1H), 8.70 (s, 1H), 8.35 (d, J = 2.5 Hz, 1H), 7.87-7.78 (m, 2H), 7.33 (dd, J = 8.3, 1.9 Hz, 1H), 7.02 (dd, J = 12.9, 1.9 Hz, 1H), 6.94 (d, J = 8.6 Hz, 1H), 4.80 (q, J = 8.5 Hz, 2H), 4.38 (s, 1H), 3.79 (s, 3H), 1.26 (s, 9H). $^{19}$F NMR (376 MHz, CDCl$_3$) δ −73.81, −106.99. |
| 88 | ESIMS m/z 465 ([M + H]$^+$) | $^1$H NMR (400 MHz, CDCl$_3$) δ 9.06 (s, 1H), 8.70 (s, 1H), 7.78 (t, J = 8.4 Hz, 1H), 7.22 (d, J = 8.3 Hz, 1H), 7.13-7.06 (m, 3H), 6.79 (dd, J = 12.7, 1.8 Hz, 1H), 4.33 (s, 1H), 3.79 (s, 3H), 2.25 (s, 3H), 1.27 (s, 9H). $^{19}$F NMR (376 MHz, CDCl$_3$) δ −57.70, −107.85. |
| 89 | ESIMS m/z 418 ([M + H]$^+$) | $^1$H NMR (400 MHz, CDCl$_3$) δ 9.08 (s, 1H), 8.65 (s, 2H), 8.14 (d, J = 9.0 Hz, 1H), 7.57-7.50 (m, 4H), 7.40-7.36 (m, 2H), 3.79 (s, 1H), 1.81-1.75 (m, 2H), 1.49-1.42 (m, 2H), 1.29 (s, 9H). $^{13}$C NMR (126 MHz, CDCl$_3$) δ 156.80, 156.13, 141.37, 139.58, 138.12, 137.80, 136.28, 134.33, 131.08, 130.70, 127.43, 126.33, 124.26, 122.30, 81.00, 39.52, 27.26, 18.50, 13.66. |
| 91 | ESIMS m/z 418 ([M + H]$^+$) | $^1$H NMR (400 MHz, CDCl$_3$) δ 9.06 (s, 1H), 8.65 (s, 2H), 7.99 (d, J = 8.4 Hz, 1H), 7.45 (t, J = 8.1 Hz, 1H), 7.38 (d, J = 8.4 Hz, 1H), 7.34 (dd, J = 8.1, 2.0 Hz, 1H), 7.29 (d, J = 1.9 Hz, 1H), 7.28-7.24 (m, 1H), 2.47 (s, 1H), 1.99 (s, 3H), 1.76 (s, 6H), 1.27 (s, 9H). $^{19}$F NMR (376 MHz, CDCl$_3$) δ −115.91. |
| 92 | ESIMS m/z 434 ([M + H]$^+$) | $^1$H NMR (400 MHz, CDCl$_3$) δ 9.07 (s, 1H), 8.70 (s, 1H), 7.80 (t, J = 8.4 Hz, 1H), 7.60 (d, J = 8.5 Hz, 2H), 7.54 (d, J = 8.5 Hz, 2H), 7.39 (dd, J = 8.3, 1.9 Hz, 1H), 7.07 (dd, J = 13.1, 1.9 Hz, 1H), 4.37 (s, 1H), 3.78 (s, 3H), 1.76 (s, 6H), 1.26 (s, 9H). $^{19}$F NMR (376 MHz, CDCl$_3$) δ −107.46. |
| 94 | ESIMS m/z 418 ([M + H]$^+$) | $^1$H NMR (400 MHz, CDCl$_3$) δ 9.06 (d, J = 2.1 Hz, 1H), 8.64 (d, J = 1.8 Hz, 2H), 8.60 (d, J = 2.7 Hz, 1H), 8.02 (d, J = 8.4 Hz, 1H), 7.81-7.73 (m, 3H), 7.65-7.61 (m, 1H), 2.47 (s, 1H), 2.04 (s, 3H), 1.27 (s, 9H). $^{19}$F NMR (376 MHz, CDCl$_3$) δ −58.15. |

TABLE 2-continued

Analytical Data.

| Compound Number | Mass Spec | NMR $^1$H, $^{13}$C, $^{19}$F |
|---|---|---|
| 95 | ESIMS m/z 438 ([M + H]$^+$) | $^1$H NMR (400 MHz, CDCl$_3$) δ 9.09 (s, 1H), 8.66 (s, 2H), 8.15 (d, J = 8.9 Hz, 1H), 7.54-7.50 (m, 2H), 7.46 (t, J = 8.0 Hz, 1H), 7.37 (dd, J = 8.1, 2.0 Hz, 1H), 7.29 (dd, J = 11.8, 2.0 Hz, 1H), 3.77 (s, 1H), 1.77 (s, 6H), 1.29 (s, 9H). $^{19}$F NMR (376 MHz, CDCl$_3$) δ −115.61. |
| 96 | ESIMS m/z 451 ([M + H]$^+$) | $^1$H NMR (400 MHz, CDCl$_3$) δ 9.07 (s, 1H), 8.70 (s, 1H), 7.80 (t, J = 8.4 Hz, 1H), 7.62-7.56 (m, 2H), 7.36 (dd, J = 8.3, 1.9 Hz, 1H), 7.28 (d, J = 8.3 Hz, 2H), 7.05 (dd, J = 13.0, 1.9 Hz, 1H), 4.37 (s, 1H), 3.78 (s, 3H), 1.26 (s, 9H). $^{19}$F NMR (376 MHz, CDCl$_3$) δ −57.83, −107.31. |
| 97 | ESIMS m/z 420 ([M + H]$^+$) | $^1$H NMR (400 MHz, CDCl$_3$) δ 9.07 (s, 1H), 8.84 (s, 2H), 7.89 (d, J = 8.5 Hz, 1H), 7.41 (t, J = 8.1 Hz, 1H), 7.36 (dt, J = 8.3, 1.7 Hz, 1H), 7.19-7.15 (m, 1H), 7.14 (t, J = 1.6 Hz, 1H), 7.07 (dd, J = 11.7, 2.0 Hz, 1H), 3.12 (d, J = 8.4 Hz, 1H), 1.83-1.78 (m, 2H), 1.48-1.44 (m, 2H), 1.25 (s, 9H). $^{19}$F NMR (376 MHz, CDCl$_3$) δ −107.19, −116.02. |
| 98 | ESIMS m/z 414 ([M + H]$^+$) | $^1$H NMR (400 MHz, CDCl$_3$) δ 9.06 (s, 1H), 8.66 (s, 2H), 7.96 (d, J = 8.3 Hz, 1H), 7.37 (d, J = 2.1 Hz, 1H), 7.32 (dd, J = 8.0, 2.2 Hz, 1H), 7.22 (d, J = 8.0 Hz, 1H), 7.14 (dd, J = 8.3, 2.1 Hz, 1H), 7.07 (d, J = 2.0 Hz, 1H), 2.47 (s, 1H), 2.31 (s, 3H), 1.97 (s, 3H), 1.76 (s, 6H), 1.28 (s, 9H). $^{13}$C NMR (126 MHz, CDCl$_3$) δ 156.59, 156.14, 140.86, 140.52, 140.41, 140.23, 139.12, 137.62, 136.02, 134.91, 130.14, 128.17, 127.18, 124.98, 124.58, 122.40, 81.22, 39.77, 36.89, 29.15, 27.38, 24.84, 22.86, 20.68. |
| 99 | ESIMS m/z 451 ([M + H]$^+$) | $^1$H NMR (400 MHz, CDCl$_3$) δ 9.10 (s, 1H), 8.66 (s, 2H), 8.12 (d, J = 8.1 Hz, 1H), 7.28 (d, J = 0.6 Hz, 2H), 7.21 (d, J = 8.3 Hz, 1H), 7.15-7.09 (m, 2H), 3.80 (s, 1H), 2.29 (s, 3H), 1.30 (s, 9H). $^{19}$F NMR (376 MHz, CDCl$_3$) δ −57.69. |
| 100 | ESIMS m/z 432 ([M + H]$^+$) | $^1$H NMR (400 MHz, CDCl$_3$) δ 9.07 (s, 1H), 8.69 (s, 1H), 7.79 (t, J = 8.4 Hz, 1H), 7.60-7.54 (m, 2H), 7.36 (td, J = 7.2, 6.3, 1.8 Hz, 3H), 7.06 (dd, J = 13.1, 1.9 Hz, 1H), 4.37 (s, 1H), 3.78 (s, 3H), 1.81-1.73 (m, 2H), 1.47-1.38 (m, 2H), 1.26 (s, 9H). $^{19}$F NMR (376 MHz, CDCl$_3$) δ −107.44. |
| 101 | ESIMS m/z 422 ([M + H]$^+$) | $^1$H NMR (400 MHz, CDCl$_3$) δ 9.09 (s, 1H), 8.85 (s, 2H), 7.89 (t, J = 8.5 Hz, 1H), 7.46 (t, J = 8.1 Hz, 1H), 7.37 (ddd, J = 8.2, 4.7, 1.8 Hz, 2H), 7.29 (d, J = 2.0 Hz, 1H), 7.18 (dt, J = 13.8, 1.6 Hz, 1H), 3.05 (d, J = 9.2 Hz, 1H), 1.76 (s, 6H), 1.26 (s, 9H). $^{19}$F NMR (376 MHz, CDCl$_3$) δ −107.26, −115.66. |
| 102 | ESIMS m/z 422 ([M + H]$^+$) | $^1$H NMR (400 MHz, CDCl$_3$) δ 9.08 (s, 1H), 8.86 (s, 2H), 8.61 (d, J = 2.6 Hz, 1H), 7.92 (t, J = 8.4 Hz, 1H), 7.83-7.71 (m, 2H), 7.69-7.59 (m, 2H), 3.04 (d, J = 8.8 Hz, 1H), 1.26 (s, 9H). $^{19}$F NMR (376 MHz, CDCl$_3$) δ −58.14, −106.71. |
| 103 | ESIMS m/z 416 ([M + H]$^+$) | $^1$H NMR (400 MHz, CDCl$_3$) δ 9.06 (s, 1H), 8.65 (s, 2H), 7.98 (d, J = 8.4 Hz, 1H), 7.41 (t, J = 8.1 Hz, 1H), 7.37 (d, J = 8.4 Hz, 1H), 7.28 (d, J = 1.8 Hz, 1H), 7.17 (dd, J = 8.1, 2.0 Hz, 1H), 7.06 (dd, J = 11.5, 1.9 Hz, 1H), 2.45 (s, 1H), 1.99 (s, 3H), 1.83-1.76 (m, 2H), 1.48-1.44 (m, 2H), 1.27 (s, 9H). $^{19}$F NMR (376 MHz, CDCl$_3$) δ −116.25. |
| 104 | ESIMS m/z 455 ([M + H]$^+$) | $^1$H NMR (400 MHz, CDCl$_3$) δ 9.09 (s, 1H), 8.65 (s, 2H), 8.16 (d, J = 8.9 Hz, 1H), 7.50 (tq, J = 4.0, 1.9 Hz, 2H), 7.45 (t, J = 8.5 Hz, 1H), 7.15-7.05 (m, 2H), 3.77 (s, 1H), 1.29 (s, 9H). $^{19}$F NMR (376 MHz, CDCl$_3$) δ −57.97, −113.10. |
| 105 | ESIMS m/z 418 ([M + H]$^+$) | $^1$H NMR (400 MHz, CDCl$_3$) δ 9.09 (s, 1H), 8.85 (s, 2H), 7.86 (t, J = 8.5 Hz, 1H), 7.38 (d, J = 2.1 Hz, 1H), 7.33 (dd, J = 8.0, 2.2 Hz, 1H), 7.22 (d, J = 8.0 Hz, 1H), 7.13 (dd, J = 8.2, 1.8 Hz, 1H), 6.94 (dd, J = 13.7, 1.8 Hz, 1H), 3.09 (d, J = 9.7 Hz, 1H), 2.30 (s, 3H), 1.76 (s, 6H), 1.27 (s, 9H). $^{19}$F NMR (376 MHz, CDCl$_3$) δ −107.77. |

TABLE 2-continued

Analytical Data.

| Compound Number | Mass Spec | NMR $^1$H, $^{13}$C, $^{19}$F |
|---|---|---|
| 106 | ESIMS m/z 436 ([M + H]$^+$) | $^1$H NMR (400 MHz, CDCl$_3$) δ 9.09 (s, 1H), 8.65 (s, 2H), 8.15 (d, J = 8.9 Hz, 1H), 7.51 (dt, J = 4.5, 1.6 Hz, 2H), 7.42 (t, J = 8.0 Hz, 1H), 7.20-7.16 (m, 1H), 7.09 (dd, J = 11.5, 2.0 Hz, 1H), 3.76 (s, 1H), 1.85-1.79 (m, 2H), 1.49-1.45 (m, 2H), 1.29 (s, 9H). $^{19}$F NMR (376 MHz, CDCl$_3$) δ −115.97. |
| 108 | ESIMS m/z 467 ([M + H]$^+$) | $^1$H NMR (400 MHz, CDCl$_3$) δ 9.08 (s, 1H), 8.70 (s, 1H), 7.82 (t, J = 8.4 Hz, 1H), 7.72 (d, J = 8.1 Hz, 2H), 7.65-7.60 (m, 2H), 7.41 (dd, J = 8.3, 1.9 Hz, 1H), 7.09 (dd, J = 13.0, 1.9 Hz, 1H), 4.37 (s, 1H), 3.78 (s, 3H), 1.26 (s, 9H). $^{19}$F NMR (376 MHz, CDCl$_3$) δ −42.67, −107.12. |
| 109 | ESIMS m/z 471 ([M + H]$^+$) | $^1$H NMR (400 MHz, CDCl$_3$) δ 9.08 (s, 1H), 8.73 (s, 2H), 8.08 (d, J = 8.4 Hz, 1H), 8.00 (q, J = 3.2 Hz, 1H), 7.73 (dd, J = 8.4, 2.2 Hz, 1H), 7.63-7.58 (m, 2H), 7.34 (dt, J = 7.7, 1.0 Hz, 2H), 2.70 (d, J = 1.0 Hz, 1H), 1.26 (s, 9H). $^{19}$F NMR (376 MHz, CDCl$_3$) δ −54.31, −57.80. |
| 110 | ESIMS m/z 453 ([M + H]$^+$) | $^1$H NMR (400 MHz, CDCl$_3$) δ 9.05 (s, 1H), 8.71 (s, 2H), 8.07 (d, J = 8.4 Hz, 1H), 8.00 (d, J = 2.1 Hz, 1H), 7.72 (dd, J = 8.4, 2.2 Hz, 1H), 7.62-7.56 (m, 2H), 7.26-7.22 (m, 2H), 6.57 (t, J = 73.6 Hz, 1H), 2.71 (d, J = 1.1 Hz, 1H), 1.26 (s, 9H). $^{19}$F NMR (376 MHz, CDCl$_3$) δ −54.28, −81.02. |
| 111 | ESIMS m/z 487 ([M + H]$^+$) | $^1$H NMR (400 MHz, CDCl$_3$) δ 9.06 (s, 1H), 8.72 (s, 2H), 8.10 (d, J = 8.4 Hz, 1H), 8.04 (d, J = 2.1 Hz, 1H), 7.77 (dd, J = 8.5, 2.2 Hz, 3H), 7.66-7.62 (m, 2H), 2.70 (d, J = 1.1 Hz, 1H), 1.26 (s, 9H). $^{19}$F NMR (376 MHz, CDCl$_3$) δ −42.49, −54.30. |
| 112 | ESIMS m/z 485 ([M + H]$^+$) | $^1$H NMR (400 MHz, CDCl$_3$) δ 9.06 (s, 1H), 8.71 (s, 2H), 8.06 (d, J = 8.4 Hz, 1H), 7.99 (d, J = 2.1 Hz, 1H), 7.72 (dd, J = 8.4, 2.2 Hz, 1H), 7.61-7.54 (m, 2H), 7.08-7.03 (m, 2H), 4.41 (q, J = 8.1 Hz, 2H), 2.69 (d, J = 1.1 Hz, 1H), 1.25 (s, 9H). $^{19}$F NMR (376 MHz, CDCl$_3$) δ −54.26, −73.88. |
| 113 | ESIMS m/z 473 ([M + H]$^+$) | $^1$H NMR (400 MHz, CDCl$_3$) δ 9.07 (s, 1H), 8.72 (s, 2H), 8.11 (d, J = 8.4 Hz, 1H), 8.00 (d, J = 1.9 Hz, 1H), 7.77 (dt, J = 8.4, 2.0 Hz, 1H), 7.62-7.53 (m, 2H), 7.48 (dd, J = 10.5, 1.7 Hz, 1H), 2.04 (s, 1H), 1.27 (s, 9H). $^{19}$F NMR (376 MHz, CDCl$_3$) δ −54.35, −62.83, −115.22. |
| 114 | ESIMS m/z 456 ([M + H]$^+$) | $^1$H NMR (400 MHz, CDCl$_3$) δ 9.07 (s, 1H), 8.96 (d, J = 2.2 Hz, 1H), 8.72 (s, 2H), 8.15 (d, J = 8.4 Hz, 1H), 8.09-8.05 (m, 1H), 8.04 (d, J = 2.1 Hz, 1H), 7.81 (ddd, J = 8.4, 5.8, 1.5 Hz, 2H), 2.76 (s, 1H), 1.27 (s, 9H). $^{19}$F NMR (376 MHz, CDCl$_3$) δ −54.38, −67.85. |
| 115 | ESIMS m/z 452 ([M + H]$^+$) | $^1$H NMR (400 MHz, CDCl$_3$) δ 9.05 (s, 1H), 8.71 (s, 2H), 8.07 (d, J = 8.5 Hz, 1H), 8.00 (d, J = 2.1 Hz, 1H), 7.74 (dd, J = 8.4, 2.2 Hz, 1H), 7.61-7.56 (m, 2H), 7.43-7.38 (m, 2H), 2.74 (d, J = 1.1 Hz, 1H), 1.82-1.75 (m, 2H), 1.50-1.44 (m, 2H), 1.26 (s, 9H). $^{19}$F NMR (376 MHz, CDCl$_3$) δ −54.27. |
| 116 | ESIMS m/z 454 ([M + H]$^+$) | $^1$H NMR (400 MHz, CDCl$_3$) δ 9.05 (s, 1H), 8.71 (s, 2H), 8.08 (d, J = 8.4 Hz, 1H), 8.02 (d, J = 2.1 Hz, 1H), 7.75 (dd, J = 8.4, 2.2 Hz, 1H), 7.64-7.57 (m, 4H), 2.72 (s, 1H), 1.78 (s, 6H), 1.26 (s, 9H). $^{19}$F NMR (376 MHz, CDCl$_3$) δ −54.27. |
| 117 | ESIMS m/z 485 ([M + H]$^+$) | $^1$H NMR (400 MHz, CDCl$_3$) δ 9.07 (s, 1H), 8.72 (s, 2H), 8.07 (d, J = 8.3 Hz, 1H), 7.76 (d, J = 2.0 Hz, 1H), 7.50 (dd, J = 8.3, 2.1 Hz, 1H), 7.24 (d, J = 8.2 Hz, 1H), 7.17-7.11 (m, 2H), 2.70 (d, J = 1.1 Hz, 1H), 2.29 (s, 3H), 1.27 (s, 9H). $^{19}$F NMR (376 MHz, CDCl$_3$) δ −54.24, −57.69. |
| 118 | ESIMS m/z 489 ([M + H]$^+$) | $^1$H NMR (400 MHz, CDCl$_3$) δ 9.06 (s, 1H), 8.72 (s, 2H), 8.09 (d, J = 8.5 Hz, 1H), 8.00-7.95 (m, 1H), 7.73 (dt, J = 8.4, 2.0 Hz, 1H), 7.49 (t, J = 8.5 Hz, 1H), 7.19-7.07 (m, 2H), 2.72 (d, J = 1.1 Hz, 1H), 1.26 (s, 9H). $^{19}$F NMR (376 MHz, CDCl$_3$) δ −54.33, −57.97, −113.40. |
| 119 | ESIMS m/z 470 ([M + H]$^+$) | $^1$H NMR (400 MHz, CDCl$_3$) δ 9.06 (s, 1H), 8.71 (s, 2H), 8.08 (d, J = 8.5 Hz, 1H), 7.99-7.92 (m, 1H), 7.74 (dt, J = 8.4, 1.9 Hz, 1H), 7.45 (t, J = 8.0 Hz, 1H), 7.21 (dd, 1 = 8.1, 2.0 Hz, 1H), 7.11 (dd, J = 11.5, 1.9 |

TABLE 2-continued

Analytical Data.

| Compound Number | Mass Spec | NMR $^1$H, $^{13}$C, $^{19}$F |
|---|---|---|
| | | Hz, 1H), 2.72 (d, J = 1.1 Hz, 1H), 1.85-1.80 (m, 2H), 1.50-1.45 (m, 2H), 1.26 (s, 9H). $^{19}$F NMR (376 MHz, CDCl$_3$) δ −54.31, −116.28. |
| 120 | ESIMS m/z 472 ([M + H]$^+$) | $^1$H NMR (400 MHz, CDCl$_3$) δ 9.06 (s, 1H), 8.72 (s, 2H), 8.09 (d, J = 8.4 Hz, 1H), 8.02-7.98 (m, 1H), 7.75 (dt, J = 8.4, 1.9 Hz, 1H), 7.49 (t, J = 8.0 Hz, 1H), 7.39 (dd, J = 8.1, 2.0 Hz, 1H), 7.31 (dd, J = 11.7, 1.9 Hz, 1H), 2.71 (d, J = 1.1 Hz, 1H), 1.77 (s, 6H), 1.26 (s, 9H). $^{19}$F NMR (376 MHz, CDCl$_3$) δ −54.08, −115.92. |

TABLE 3

Rating Scale For Disease Control in Wheat Leaf Blotch (SEPTTR) Assay.

| % Disease Control | Rating |
|---|---|
| 80-100 | A |
| 60-79 | B |
| 40-59 | C |
| <40 | D |
| Not tested | E |

TABLE 4

Biological Activity - Disease Control in Type A and Type B Assays.

| Compound Number | SI SEPTTR Type A Assay (50 ppm) | SI SEPTTR Type B Assay (100 g/ha) | | FI SEPTTR Type B Assay (100 g/ha) | |
|---|---|---|---|---|---|
| | 1DP | 3DC | 3DP | 3DC | 3DP |
| 1 | A | A | A | A | A |
| 2 | A | A | A | A | A |
| 3 | A | B | B | A | B |
| 4 | E | E | E | E | E |
| 5 | A | E | E | E | E |
| 6 | A | E | E | E | E |
| 7 | A | E | E | E | E |
| 8 | A | A | A | A | A |
| 9 | A | A | B | A | A |
| 10 | A | A | A | A | B |
| 11 | A | B | A | B | B |
| 12 | B | E | E | E | E |
| 13 | A | E | E | E | E |
| 14 | A | A | A | A | B |
| 15 | E | A | A | B | A |
| 16 | E | A | A | A | A |
| 17 | E | A | A | A | A |
| 18 | E | E | E | E | E |
| 19 | E | A | B | A | A |
| 20 | E | E | E | E | E |
| 21 | E | E | E | E | E |
| 22 | E | A | A | A | A |
| 23 | E | A | A | A | A |
| 24 | E | A | A | A | A |
| 25 | A | A | B | A | A |
| 26 | A | A | A | A | A |
| 27 | A | E | E | E | E |
| 28 | A | E | E | E | E |
| 29 | A | E | E | E | E |
| 30 | A | A | A | A | A |
| 31 | A | E | E | E | E |
| 32 | A | A | A | B | A |
| 33 | A | E | E | E | E |
| 34 | A | E | E | E | E |
| 35 | A | E | E | E | E |
| 36 | A | E | E | E | E |
| 37 | A | E | E | E | E |
| 38 | A | E | E | E | E |
| 39 | A | E | E | E | E |
| 40 | A | E | E | E | E |
| 41 | A | E | E | E | E |
| 42 | A | E | E | E | E |
| 43 | C | E | E | E | E |
| 44 | A | E | E | E | E |
| 45 | A | E | E | E | E |
| 46 | A | E | E | E | E |
| 47 | A | E | E | E | E |
| 48 | A | E | E | E | E |
| 49 | A | E | E | E | E |
| 50 | A | E | E | E | E |
| 51 | A | E | E | E | E |
| 52 | B | E | E | E | E |
| 53 | A | E | E | E | E |
| 54 | A | E | E | E | E |
| 55 | A | E | E | E | E |
| 56 | A | E | E | E | E |
| 57 | A | E | E | E | E |
| 58 | A | E | E | E | E |
| 59 | A | E | E | E | E |
| 60 | A | E | E | E | E |
| 61 | A | E | E | E | E |
| 62 | A | E | E | E | E |
| 63 | A | E | E | E | E |
| 64 | E | E | E | A | A |
| 65 | E | E | E | A | A |
| 66 | E | E | E | D | A |
| 67 | E | E | E | A | A |
| 68 | E | E | E | B | A |
| 69 | E | E | E | C | A |
| 70 | E | E | E | A | A |
| 71 | E | E | E | A | A |
| 72 | E | E | E | B | A |
| 73 | E | E | E | C | A |
| 74 | E | E | E | A | A |
| 75 | E | E | E | A | A |
| 76 | E | E | E | A | B |
| 77 | E | E | E | A | A |
| 78 | E | E | E | A | A |
| 79 | E | E | E | A | A |
| 80 | E | E | E | A | A |
| 81 | E | E | E | A | A |
| 82 | E | E | E | A | A |
| 83 | E | E | E | A | A |
| 84 | E | E | E | A | A |
| 85 | E | E | E | A | A |

TABLE 4-continued

Biological Activity - Disease Control in Type A and Type B Assays.

| Compound Number | SI SEPTTR Type A Assay (50 ppm) 1DP | SI SEPTTR Type B Assay (100 g/ha) 3DC | SI SEPTTR Type B Assay (100 g/ha) 3DP | FI SEPTTR Type B Assay (100 g/ha) 3DC | FI SEPTTR Type B Assay (100 g/ha) 3DP |
|---|---|---|---|---|---|
| 86 | E | E | E | B | A |
| 87 | E | E | E | A | A |
| 88 | E | E | E | A | A |
| 89 | E | E | E | B | A |
| 91 | E | E | E | A | A |
| 92 | E | E | E | A | A |
| 94 | E | E | E | A | A |
| 95 | E | E | E | A | A |
| 96 | E | E | E | A | A |
| 97 | E | E | E | A | A |
| 98 | E | E | E | E | E |
| 99 | E | E | E | A | A |
| 100 | E | E | E | A | A |
| 101 | E | E | E | A | A |
| 102 | E | E | E | A | A |
| 103 | E | E | E | A | A |
| 104 | E | E | E | A | A |
| 105 | E | E | E | A | A |
| 106 | E | E | E | B | A |
| 108 | E | E | E | E | E |
| 109 | E | E | E | E | E |
| 110 | E | E | E | E | E |
| 111 | E | E | E | E | E |
| 112 | E | E | E | E | E |
| 113 | E | E | E | E | E |
| 115 | E | E | E | E | E |
| 116 | E | E | E | E | E |
| 117 | E | E | E | E | E |
| 118 | E | E | E | E | E |
| 119 | E | E | E | E | E |
| 120 | E | E | E | E | E |

\* SI—SEPTTR standard laboratory isolate
\* FI—SEPTTR field isolate
\*SEPTTR—Wheat Leaf Blotch (*Septo cospora beticola*), Early Blight of Tomato (*Alternaria solani*), and Net Blotch of Barley (*Pyrenophora teres*).

16. The composition according to claim 15 wherein the fungal pathogen is one of Leaf Blotch of Wheat (*Septoria tritici*), Wheat Brown Rust (*Puccinia triticina*), and Rust of Soybean (*Phakopsora pachyrhizi*).

17. A method for the control and/or prevention of a fungal disease affecting a plant, the method including the step of: applying a fungicidally effective amount of at least one of the compounds according to claim 1 to at least one of the following; a plant, an area adjacent to the plant, a portion soil adapted to support growth of the plant, a root of the plant, a seed of a plant, and at least a portion of foliage of a plant.

* * * * *